(12) United States Patent
Allerton et al.

(10) Patent No.: US 6,756,373 B1
(45) Date of Patent: Jun. 29, 2004

(54) PHARMACEUTICALLY ACTIVE COMPOUNDS

(75) Inventors: Charlotte Moira Norfor Allerton, Sandwich (GB); Christopher Gordon Barber, Sandwich (GB); Graham Nigel Maw, Sandwich (GB); David James Rawson, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/684,228

(22) Filed: Oct. 6, 2000

Related U.S. Application Data
(60) Provisional application No. 60/231,411, filed on Sep. 8, 2000.

(30) Foreign Application Priority Data

Oct. 11, 1999 (GB) ............................................. 9924041
Jul. 28, 2000 (GB) ............................................. 0018660

(51) Int. Cl.[7] .................. C07D 487/04; A61K 31/519; A61P 15/12; A61P 15/10

(52) U.S. Cl. .............................. 514/234.2; 514/262.1; 544/118; 544/262; 546/275.4; 546/276.1

(58) Field of Search ................................ 544/118, 256, 544/262; 546/1, 290, 329, 275.4, 276.1; 548/364.7, 366.7; 514/234.2, 262.1

(56) References Cited

U.S. PATENT DOCUMENTS

| | | | |
|---|---|---|---|
| 4,663,326 A | 5/1987 | Hamilton | 514/258 |
| 4,666,908 A | 5/1987 | Hamilton | 514/229 |
| 4,871,843 A | 10/1989 | Roger et al. | 540/575 |
| 5,250,534 A | 10/1993 | Bell et al. | 514/258 |
| 5,272,147 A | 12/1993 | Bell et al. | 514/234 |
| 5,294,612 A * | 3/1994 | Bacon et al. | 514/234.2 |
| 5,346,901 A | 9/1994 | Bell et al. | 514/258 |
| 5,426,107 A | 6/1995 | Bell et al. | 514/234 |
| 5,719,283 A | 2/1998 | Bell et al. | 544/262 |
| 5,734,053 A | 3/1998 | Terrett | 544/277 |

(List continued on next page.)

FOREIGN PATENT DOCUMENTS

| | | | |
|---|---|---|---|
| EP | 201188 * | 12/1986 | |
| EP | 0201188 | 12/1986 | C07D/487/04 |
| EP | 0463756 | 1/1992 | C07D/487/04 |
| EP | 0526004 | 2/1993 | C07D/487/04 |
| EP | 0349239 | 3/1994 | C07D/487/04 |
| EP | 0352960 | 10/1994 | C07D/473/30 |
| EP | 0636626 | 2/1995 | C07D/487/04 |
| EP | 0812845 | 12/1997 | C07D/487/04 |
| EP | 0916675 | 5/1999 | C07D/487/04 |
| EP | 0995750 | 4/2000 | C07D/487/04 |
| JP | 08253484 | 1/1996 | C07D/487/04 |
| WO | WO 9306104 | 4/1993 | C07D/487/04 |
| WO | WO 9307149 | 4/1993 | C07D/487/04 |
| WO | WO 9312095 | 6/1993 | C07D/239/91 |
| WO | WO 9315062 | 8/1993 | C07D/241/04 |
| WO | WO 9400453 | 1/1994 | C07D/473/30 |
| WO | WO 9405661 | 3/1994 | C07D/471/04 |
| WO | WO 9428902 | 12/1994 | A61K/31/505 |
| WO | 9616644 * | 6/1996 | |
| WO | WO 9616644 | 6/1996 | A61K/31/00 |
| WO | WO 9616657 | 6/1996 | A61K/31/505 |
| WO | WO 9628429 | 9/1996 | C07D/239/70 |
| WO | WO 9628448 | 9/1996 | C07D/487/04 |
| WO | WO 9849166 | 11/1998 | C07D/487/04 |
| WO | WO 9911259 | 3/1999 | A61K/31/40 |
| WO | WO 9954333 | 10/1999 | C07D/487/04 |
| WO | WO 9964004 | 12/1999 | A61K/31/505 |
| WO | WO 0024745 | 5/2000 | C07D/487/04 |
| WO | WO 0312095 | 2/2003 | C12N/9/42 |

OTHER PUBLICATIONS

Dumaitre J. Med. Chem., 1996, 39, 1635–1644.
Herriet W. Hamilton, et al., J. Med. Chem, 1987, 30, 91–96.
Micheal Czarniecki, et al., Annual Reports in Medicinal Chemistry, 31, 61–70.
Andreas Terfort, et al., J. Chem. Soc. Perkin Trans 1, 1996, pp. 1467–1479.
Henry R. Henze, et al., J. Am. Chem. Soc., Feb., 1939, pp. 433–435.
J. Med. Chem, 1996, 39, 1635–1644.

*Primary Examiner*—Mark L Berch
(74) *Attorney, Agent, or Firm*—Peter C. Richardson; Gregg C. Benson; Martha G. Munchhof

(57) ABSTRACT

There is provided a compound of formula I:

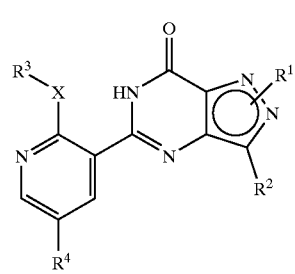

wherein
  X represents O or $NR^5$
  $R^4$ represents H, halo, cyano, nitro, halo(loweralkyl), $OR^6$, $OC(O)R^7$, $C(O)R^8$, $C(O)OR^9$, $C(O)NR^{10}R^{11}$, $NR^{12}R^{13}$, $NR^{16}Y(O)R^{17}$, $N[Y(O)R^{17}]_2$, $SOR^{18}$, $SO_2R^{19}$, C(O)AZ, lower alkyl, lower alkenyl, lower alkynyl, Het, alkylHet, aryl, alkylaryl (which latter seven groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)
which are useful in the curative and prophylactic treatment of a medical condition for which inhibition of a cyclic guanosine 3',5'-monophosphate phosphodiesterase (e.g., cGMP PDE5) is desired.

18 Claims, No Drawings

U.S. PATENT DOCUMENTS

| | | | |
|---|---|---|---|
| 5,736,548 A | 4/1998 | Bacon et al. | 514/258 |
| 5,798,375 A | 8/1998 | Tsujita et al. | 514/369 |
| 5,849,741 A | 12/1998 | Watanabe et al. | 514/248 |
| 5,859,006 A | 1/1999 | Daugan | 514/249 |
| 5,955,611 A | 9/1999 | Dunn et al. | 544/262 |
| 5,981,527 A | 11/1999 | Daugan et al. | 514/250 |
| 6,025,494 A | 2/2000 | Daugan | 546/64 |
| 6,042,847 A | 3/2000 | Kerc et al. | 424/472 |
| 6,127,542 A | 10/2000 | Daugan | 546/64 |
| 6,140,329 A | 10/2000 | Daugan | 514/250 |
| 6,143,746 A | 11/2000 | Daugan et al. | 514/249 |
| 6,159,997 A | 12/2000 | Tsujita et al. | 514/369 |
| 6,218,392 B1 | 4/2001 | Watanabe et al. | 514/248 |
| 6,251,904 B1 * | 6/2001 | Bunnage et al. | 544/262 |
| 6,407,259 B1 * | 6/2002 | Harris et al. | 548/364.1 |
| 6,512,002 B2 * | 1/2003 | Lee et al. | 514/427 |
| 2002/0013327 A1 * | 1/2002 | Lee et al. | 514/256 |
| 2002/0038024 A1 * | 3/2002 | Allerton et al. | 544/262 |
| 2002/0091129 A1 * | 7/2002 | Boolell | 514/252.16 |
| 2002/0165237 A1 * | 11/2002 | Fryburg et al. | 514/252.16 |
| 2002/0173502 A1 * | 11/2002 | Allerton | 544/262 |
| 2003/0018037 A1 * | 1/2003 | Lempriere et al. | 514/262.1 |
| 2003/0064990 A1 * | 4/2003 | Denton et al. | 514/262.1 |

* cited by examiner

PHARMACEUTICALLY ACTIVE COMPOUNDS

This application is filed claiming priority from co-pending Provisional Application No. 60/231,411, filed Sep. 8, 2000.

FIELD OF THE INVENTION

This invention relates to pharmaceutically useful compounds, in particular compounds which are useful in the inhibition of cyclic guanosine 3',5'-monophosphate phosphodiesterases (cGMP PDEs), such as type 5 cyclic guanosine 3',5'-monophosphate phosphodiesterases (cGMP PDE5). The compounds therefore have utility in a variety of therapeutic areas, including male erectile dysfunction (MED).

PRIOR ART

EP-A-0636626 relates to a class of pyrazolo[3,4-d]-pyrimidone compounds and their use as inhibitors of cGMP specific PDE. A series of 6-phenylpyrazolo[3,4-d]pyrimidinones, their synthesis and their cyclic GMP phosphodiesterase inhibitory activity are described in *J. Med. Chem.*, 1996, 39, 1635–1644. International patent application WO 96/16657 discloses the use of certain pyrazolo[3,4-d]pyrimidinone compounds (amongst others) in the treatment of MED.

EP-A-0526004 describes certain pyrazolo[4,3-d]pyrimidinone compounds as antianginal agents. International patent application WO 94/28902 discloses the use of certain pyrazolo[3,4-d]pyrimidinone compounds (amongst others) in the treatment of MED.

DISCLOSURE OF THE INVENTION

According to the present invention, there is provided a compound of general formula I:

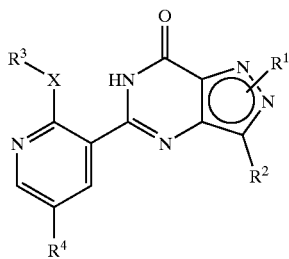

or a pharmaceutically or veterinarily acceptable salt and/or solvate thereof,
wherein X represents O or $NR^5$ $R^1$ represents H, lower alkyl, Het, alkylHet, aryl or alkylaryl (which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^2$ represents H, halo, cyano, nitro, $OR^6$, $OC(O)R^7$, $C(O)R^8$, $C(O)OR^9$, $C(O)NR^{10}R^{11}$, $NR^{12}R^{13}$, $SO_2NR^{14}R^{15}$, lower alkyl, Het, alkylHet, aryl or alkylaryl (which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^3$ represents H, lower alkyl, alkylHet or alkylaryl (which latter three groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^4$ represents H, halo, cyano, nitro, halo(loweralkyl), $OR^6$, $OC(O)R^7$, $C(O)R^8$, $C(O)OR^9$, $C(O)NR^{10}R^{11}$, $NR^{12}R^{13}$, $NR^{16}Y(O)R^{17}$, $N[Y(O)R^{17}]_2$, $SOR^{18}$, $SO_2R^{19}$, $C(O)AZ$, lower alkyl, lower alkenyl, lower alkynyl, Het, alkylHet, aryl, alkylaryl (which latter seven groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

Y represents C or S(O)

A represents lower alkylene

Z represents $OR^6$, halo, Het or aryl (which latter two groups are both optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^{10}$ and $R^{11}$ independently represent H or lower alkyl (which latter group is optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10a}R^{11a}$, $NR^{10}R^{11}$, $SO_2NR^{14}R^{15}$ and $NR^{20}S(O)_2R^{21}$ or Het or aryl optionally substituted with one or more of said latter thirteen groups) or one of $R^{10}$ and $R^{11}$ may be lower alkoxy, amino or Het, which latter two groups are both optionally substituted with lower alkyl $R^{10a}$ and $R^{11a}$ independently represent $R^{10}$ and $R^{11}$ as defined above, except that they do not represent groups that include lower alkyl, Het or aryl, when these three groups are substituted and/or terminated (as appropriate) by one or more substituents that include one or more $C(O)NR^{10a}R^{11a}$ and/or $NR^{12}R^{13}$ groups $R^{12}$ and $R^{13}$ independently represent H or lower alkyl (which latter group is optionally substituted and/or terminated with one or more substituents selected from $OR^6$, $C(O)OR^9$, $C(O)NR^{22}R^{23}$ and $NR^{24}R^{25}$), one of $R^{12}$ or $R^{13}$ may be C(O)-lower alkyl or C(O)Het (in which Het is optionally substituted with lower alkyl), or $R^{12}$ and $R^{13}$ together represent $C_{3-7}$ alkylene (which alkylene group is optionally unsaturated, optionally substituted by one or more lower alkyl groups and/or optionally interrupted by O or $NR^{26}$)

$R^{14}$ and $R^{15}$ independently represent H or lower alkyl or $R^{14}$ and $R^{15}$, together with the nitrogen atom to which they are bound, form a heterocyclic ring $R^{16}$ and $R^{17}$ independently represent H or lower alkyl (which latter group is optionally substituted and/or terminated with one or more substituents selected from $OR^6$, $C(O)OR^9$, $C(O)NR^{22}R^{23}$ and $NR^{24}R^{25}$) or one of $R^{16}$ and $R^{17}$ may be Het or aryl, which latter two groups are both optionally substituted with lower alkyl $R^5$, $R^6$, $R^7$, $R^8$, $R^9$, $R^{18}$, $R^{19}$, $R^{20}$, $R^{22}$, $R^{23}$, $R^{24}$ and $R^{25}$ independently represent H or lower alkyl $R^{18}$ and $R^{19}$ independently represent lower alkyl $R^{21}$ represents lower alkyl or aryl $R^{26}$ represents H, lower alkyl, aryl, $C(O)R^{27}$ or $S(O)_2R^{28}$ $R^{27}$ represents H, lower alkyl or aryl $R^{28}$ represents lower alkyl or aryl Het represents an optionally substituted four- to twelve-membered heterocyclic group, which group contains one or more heteroatoms selected from nitrogen, oxygen, sulphur and mixtures thereof which compounds are referred to together hereinafter as "the compounds of the invention".

The term "aryl", when used herein, includes six- to ten-membered carbocyclic aromatic groups, such as phenyl and naphthyl, which groups are optionally substituted with one or more substituents selected from aryl (which group may not be substituted by any further aryl groups), lower alkyl, Het, halo, cyano, nitro, $OR^6$, $OC(O)R^7$, $C(O)R^8$, $C(O)OR^9$, $C(O)NR^{10a}R^{11a}$, $NR^{12a}R^{13a}$ (wherein $R^{12a}$ and $R^{13a}$ independently represent $R^{12}$ and $R^{13}$ as hereinbefore defined, except that: (i) they do not represent C(O)Het in which Het is substituted by one or more substituents that include one or more $C(O)NR^{10a}R^{11a}$ and/or $NR^{12a}R^{13a}$ groups; or (ii) they do not together represent $C_{3-7}$ alkylene interrupted by $NR^{26}$) and $SO_2NR^{14}R^{15}$.

The term "Het", when used herein, includes four- to twelve-membered, preferably four- to ten-membered, ring systems, which rings contain one or more heteroatoms selected from nitrogen, oxygen, sulfor and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below), $OR^6$, $OC(O)R^7$, $C(O)R^8$, $C(O)OR^9$, $C(O)NR^{10a}R^{11a}$, $NR^{12a}R^{13a}$ and $SO_2NR^{14}R^{15}$. The term thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, pyrazolyl imidazopyridinyl and piperazinyl. Substitution at Het may be at a carbon atom of the Het ring or, where appropriate, at one or more of the heteroatoms.

"Het" groups may also be in the form of an N-oxide.

The heterocyclic ring that $R^{14}$ and $R^{15}$ (together with the nitrogen atom to which they are bound) may represent may be any heterocyclic ring that contains at least one nitrogen atom, and which ring forms a stable structure when attached to the remainder of the molecule via the essential nitrogen atom (which, for the avoidance of doubt, is the atom to which $R^{14}$ and $R^{15}$ are attached). In this respect, heterocyclic rings that $R^{14}$ and $R^{15}$ (together with the nitrogen atom to which they are bound) may represent include four- to twelve-membered, preferably four- to ten-membered, ring systems, which rings contain at least one nitrogen atom and optionally contain one or more further heteroatoms selected from nitrogen, oxygen and/or sulfur, and which rings may contain one or more double bonds or be non-aromatic, partly aromatic or wholly aromatic in character. The term thus includes groups such as azetidinyl, pyrrolidinyl, imidazolyl, indolyl, isoazoyl, oxazoyl, triazolyl, tetrazolyl, morpholinyl, piperidinyl, pyrazolyl and piperazinyl.

The term "lower alkyl" (which includes the alkyl part of alkylHet and alkylaryl groups), when used herein, means $C_{1-6}$ alkyl and includes methyl, ethyl, propyl, butyl, pentyl and hexyl groups. Unless otherwise specified, alkyl groups may, when there is a sufficient number of carbon atoms, be linear or branched, be saturated or unsaturated, be cyclic, acyclic or part cyclic/acyclic, and/or be substituted by one or more halo atoms. Preferred lower alkyl groups for use herein are $C_{1-3}$ alkyl groups. Alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ may represent, and with which $R^1$, $R^2$, $R^3$, $R^4$, $R^{10}$, $R^{11}$, $R^{12}$, $R^{13}$, $R^{16}$, $R^{17}$, aryl, alkylaryl, alkylHet and Het may be substituted, may, when there is a sufficient number of carbon atoms, be linear or branched, be saturated or unsaturated, be cyclic, acyclic or part cyclic/acyclic, be interrupted by one or more of oxygen, sulfur and optionally alkylated or optionally acylated nitrogen and/or be substituted by one or more halo atom. The terms "lower alkenyl" and "lower alkynyl", when used herein, include $C_{2-6}$ groups having one or more double or triple carbon-carbon bonds, respectively. Otherwise, the terms "lower alkenyl" and "lower alkynyl" are defined in the same way as the term "lower alkyl". Similarly, the term "lower alkylene", when used herein, includes $C_{2-6}$ groups which can be bonded at two places on the group and is otherwise defined in the same way as "lower alkyl". The term "acyl" includes C(O)-lower alkyl.

The terms "alkylHet" and "alkylaryl" include $C_{1-6}$ alkylHet and $C_{1-6}$ alkylaryl.

The alkyl groups (e.g. the $C_{1-6}$ alkyl groups) of alkylHet and alkylaryl may, when there is a sufficient number of carbon atoms, be linear or branched, be saturated or unsaturated, and/or be interrupted by oxygen. When used in this context, the terms "Het" and "aryl" are as defined hereinbefore. Substituted alkylHet and alkylaryl may have substituents on the ring and/or on the alkyl chain.

Halo groups with which the above-mentioned groups may be substituted or terminated include fluoro, chloro, bromo and iodo.

Compounds of general formula (I) can be represented by formulae IA and IB:

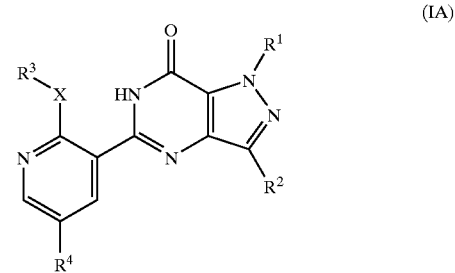

(IA)

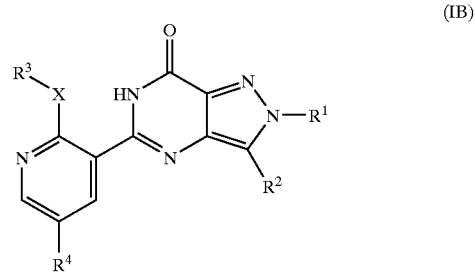

(IB)

wherein $R^1$, $R^2$, $R^3$, $R^4$ and X are as defined hereinbefore.

The pharmaceutically or veterinarily acceptable salts of the compounds of the invention which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J. to Pharm, Sci., 66, 1–19, 1977.

The pharmaceutically acceptable solvates of the compounds of the invention include the hydrates thereof.

Also included within the scope of the compound and various salts of the invention are polymorphs thereof.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereolsomeric salts formed by reaction of the corresponding racemate with a suitable optically active acid or base, as appropriate.

All stereoisomers are included within the scope of the invention.

A preferred group of compounds according to a further aspect of the invention, are compounds of formulae I, IA and IB as hereinbefore defined, wherein:

$R^1$ represents H, lower alkyl, Het, alkylHet, or alkylaryl (which latter four groups are all optionally substituted and/or terminated with one or more substituents selected from cyano, lower alkyl, $OR^6$, $C(O)OR^9$ or $NR^{12}R^{13}$);

$R^2$ represents H, halo, lower alkyl, Het or aryl (which latter three groups are all optionally substituted and/or terminated with one or more substituents as defined hereinbefore, and preferably with $NR^{12}R^{13}$ or $SO_2NR^{14}R^{15}$);

$R^3$ represents $C_1$–$C_4$ alkyl or $C_3$–$C_4$ cycloalkyl which are optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$);

$R^4$ represents halo, cyano, nitro, $C(O)R^8$, $C(O)OR^9$, $C(O)NR^{10}R^{11}$, $NR^{12}R^{13}$, $N[Y(O)R^{17}]_2$, $NR^{16}Y(O)R^{17}$, $SOR^{18}$, $SO_2R^{19}$, C(O)AZ, lower alkyl, lower alkynyl, Het or aryl, which latter three groups are all optionally substituted and/or terminated with one or more substituents as defined hereinbefore;

and wherein Y, A, Z, $R^{10}$, $R^{11}$, $R^{12}$, $R^{13}$, $R^{14}$, $R^{15}$, $R^{16}$, $R^{17}$, $R^5$, $R^6$, $R^7$, $R^8$, $R^9$, $R^{18}$, $R^{19}$ and Het are as herein before defined.

Further preferred compounds herein are those in which $R^1$ represents optionally substituted lower alkyl, more preferably lower alkyl, lower alkoxy-terminated lower alkyl, $NR^{12}R^{13}$-terminated lower alkyl, or N-morpholino- terminated lower alkyl. Alternatively, $R^1$ may represent a 4-piperidinyl or a 3-azetidinyl group, optionally substituted at the nitrogen atom of the piperidinyl group with lower alkyl or $C(O)OR^9$.

In such further preferred compounds of the invention, $R^2$ represents $C(O)NR^{10}R^{11}$, $NR^{12}R^{13}$, lower alkyl optionally interrupted by one or more of O, S or N, optionally substituted at N by lower alkyl or acyl, or optionally substituted aryl or Het. More preferably, when $R^2$ is interrupted lower alkyl, the interrupting atoms are one or more of O and lower alkylated-N and when $R^2$ is aryl, it is optionally substituted phenyl or pyridyl.

Particularly preferred compounds of the invention are those in which $R^2$ represents $C(O)NR^{10}R^{11}$, $NR^{12}R^{13}$, $C_{1-4}$ alkyl optionally interrupted by O or N, optionally substituted at N by lower alkyl, optionally substituted phenyl, or optionally substituted pyridin-2-yl, pyridin-3-yl, pyrimidin-5-yl, pyrazin-2-yl, pyrazol-4-yl, oxadiazol-2-yl, furan-2-yl, furan-3-yl, tetrahydrofuran-2-yl and imidazo[1,2-a]pyridin-6-yl.

In the further and particularly preferred compounds of the invention, $R^3$ may represent lower alkyl or cycloalkyl. Also, X is preferably O.

Such further and particularly preferred compounds of the invention have $R^4$ representing halo, lower alkyl, lower alkynyl, optionally substituted Het, optionally substituted aryl, $C(O)R^8$, $C(O)AZ$, $C(O)OR^9$, $C(O)NR^{10}R^{11}$, $NR^{12}R^{13}$ or $NR^{16}Y(O)R^{17}$. More preferred values for $R^4$ are $C(O)R^8$ (e.g. acetyl), halo (e.g. iodo), $SO_2R^{19}$ (wherein $R^{19}$ represents lower alkyl) and $C(O)NR^{10}R^{11}$ (e.g. where $R^{10}$ and $R^{11}$ independently represent H and lower alkyl and/or one of $R^{10}$ and $R^{11}$ is lower alkoxy) or NHB, wherein B represents H, $SO_2CH_3$ or C(O)Het.

Further preferred compounds of the invention include those in which $R^4$ represents iodo, lower alkyl, lower alkynyl (which latter two groups are substituted and/or terminated by $C(O)OR^9$ (wherein $R^9$ represents H or $C_{1-6}$ alkyl)), $N(H)Y(O)R^{17}$, $N[Y(O)R^{17}]_2$, optionally substituted Het or $NR^{12}R^{13}$ (wherein $R^{12}$ and $R^{13}$ together represent $C_{3-5}$ alkylene interrupted by O or N—S(O)$_2$-(optionally substituted aryl)).

Compounds of the invention that are more preferred still are include those in which $R^4$ represents $N(H)Y(O)R^{17}$ (wherein $R^{17}$ represents $C_{1-4}$ alkyl optionally substituted and/or terminated by C(O)OH or C(O)O-lower alkyl).

Preferred compounds of the invention include the compounds of Examples 1 to 87 described hereinafter (excluding the preparative examples). More preferred compounds include the compounds of Examples 1, 20, 22, 24, 32, 34, 44a, 44b, 44c, 63, 64, 65, 66, 67, and 85 and the compounds of Examples 5, 16, 17, 21, 26, 29, 47, 48, 49, 50, 50a, 51, 51a, 59, 68, 70, 71, 73, 74, 75, 77, 79, 80, 84, 86, 87, 89, 91, 92, 113, 114, 116, 118–128, 130–136, 138, 140, 143.

Highly preferred compounds herein include the following:

5-(2-Butoxy-5-iodo-3-pyridinyl)-3-ethyl-2-(2-methoxyethyl)-2,6-dihydro-7H-pyrazolo[4,3-d] pyrimidin-7-one;

5-(2-Butoxy-5-iodo-3-pyridinyl)-3-ethyl-1-(2-methoxyethyl)-1,6-dihydro-7H-pyrazolo[4,3-d] pyrimidin-7-one;

5-(5-Iodo-2-isobutoxy-3-pyridinyl)-2-methyl-3-propyl-2, 6-dihydro-7H-pyrazolo[4,3-a]pyrimidin-7-one;

5-(2-Butoxy-5-iodo-3-pyridinyl)-2-[2-(4-morpholinyl) ethyl]-3-ethyl-2,6-dihydro-7H-pyrazolo[4,3-d] pyrimidin-7-one;

tert-Butyl 4-[5-(2-butoxy-5-iodo-3-pyridinyl)-3-ethyl-7-oxo-6,7-dihydro -2H-pyrazolo[4,3-d]pyrimidin-2-yl]-1-piperidinecarboxylate;

tert-Butyl 3-[5-(2-butoxy-5-iodo-3-pyridinyl)-3-ethyl-7-oxo-6,7-dihydro-2H-pyrazolo[4,3-d]pyrimidin-2-yl]-1-azetidinecarboxylate;

5-(2-Propoxy-5-iodo-3-pyridinyl)-3-ethyl-7-oxo-6,7-dihydro-2H-pyrazolo-[4,3-d]pyrimidin-5-yl] nicotinate;

tert-Butyl [3-ethyl-5-(5-iodo-2-propoxy-3-pyridinyl)-7-oxo-6,7-dihydro-1H-pyrazolo[4,3-d]pyrimidin-1-yl] acetate;

tert-Butyl [3-ethyl-5-(5-iodo-2-propoxy-3-pyridinyl)-7-oxo-6,7-dihydro-2H-pyrazolo[4,3-d]pyrimidin-2-yl] acetate;

[3-Ethyl-5-(5-iodo-2-propoxy-3-pyridinyl)-7-oxo-6,7-dihydro-1H-pyrazolo[4,3-d]pyrimidin-1-yl]acetic acid;

[3-Ethyl-5-(5-iodo-2-propoxy-3-pyridinyl)-7-oxo-6,7-dihydro-2H-pyrazolo[4,3-d]pyrimidin-2-yl]acetic acid;

5-(2-Propoxy-5-iodo-3-pyridinyl)-1-methyl-3-propyl-1,6-dihydro-7H-pyrazolo[4,3-d]pyrimidin-7-one;

2-[2-(Dimethylamino)ethyl]-5-(2-ethoxy-5-iodo-3-pyridinyl)-3-ethyl-2,6-dihydro-7H-pyrazolo[4,3-d]pyrimidin-7-one;

6-Butoxy-5-[3-ethyl-2-(2-methoxyethyl)-7-oxo-6,7-dihydro-2H-pyrazolo[4,3-d]pyrimidin-5-yl]-N-methoxy-N-methylnicotinamide;

5-(5-Acetyl-2-butoxy-3-pyridinyl)-3-ethyl-2-(2-methoxyethyl)-2,6-dihydro-7H-pyrazolo[4,3-d]pyrimidin-7-one;

5-[5-Acetyl-2-(2-methoxy-1-methylethoxy)-3-pyridinyl]-3-ethyl-2-(2-methoxyethyl)-2,6-dihydro-7H-pyrazolo[4,3-d]pyrimidin-7-one;

5-(5-Acetyl-2-butoxy-3-pyridinyl)-3-ethyl-1-(2-methoxyethyl)-1,6-dihydro-7H-pyrazolo[4,3-d]pyrimidin-7-one;

6-Isobutoxy-N,N-dimethyl-5-(2-methyl-7-oxo-3-propyl-6,7-dihydro-2H-pyrazolo[4,3-a]pyrimidin-5-yl)nicotinamide;

5-(5-Glycoloyl-2-isobutoxy-3-pyridinyl)-2-methyl-3-propyl-2,6-dihydro-7H-pyrazolo[4,3-d]pyrimidin-7-one;

5-(5-Acetyl-2-butoxy-3-pyridinyl)-2-[2-(dimethoxyethyl)-ethyl]-3-ethyl-2,6-dihydro-7H-pyrazolo[4,3-d]pyrimidin-7-one;

5-(5-Acetyl-2-butoxy-3-pyridinyl)-2-[2-(4-morpholinyl)-ethyl]-3-ethyl-2,6-dihydro-7H-pyrazolo[4,3-d]pyrimidin-7-one;

5-(5-Acetyl-2-butoxy-3-pyridinyl)-2-[2-(4-piperidinyl)ethyl]-3-ethyl-2,6-dihydro-7H-pyrazolo[4,3-d]pyrimidin-7-one;

tert-Butyl 4-[2-(5-(5-acetyl-2-butoxy-3-pyridinyl)-3-ethyl-7-oxo-6,7-dihydro-2H-pyrazolo[4,3-d]pyrimidin-2-yl)ethyl]-1-piperidinecarboxylate;

5-(5-Acetyl-2-butoxy-3-pyridinyl)-3-ethyl-2-(1-methyl-4-piperidinyl)-2,6-dihydro-7H-pyrazolo[4,3-d]pyrimidin-7-one;

[5-(5-Acetyl-2-propoxy-3-pyridinyl)-3-ethyl-7-oxo-6,7-dihydro-1H-pyrazolo[4,3-d]pyrimidin-1-yl]acetic acid;

5-(1-Methyl-7-oxo-3-propyl-6,7-dihydro-1H-pyrazolo[4,3-d]pyrimidin-5-yl)-6-propoxynicotinonitrile;

1-Methyl-5-[2-propoxy-5-(1H-tetrazol-5-yl)-3-pyridinyl]-3-propyl-1,6-dihydro-7H-pyrazolo[4,3-d]pyrimidin-7-one;

5-[5-(3-Hydroxy-5-isoxazolyl)-2-propoxy-3-pyridinyl]-1-methyl-3-propyl-1,6-dihydro-7H-pyrazolo[4,3-a]pyrimidin-7-one;

5-(5-Amino-2-propoxy-3-pyridinyl)-1-methyl-3-propyl-1,6-dihydro-7H-pyrazolo[4,3-d]pyrimidin-7-one;

{[5-(1-Methyl-7-oxo-3-propyl-6,7-dihydro-1H-pyrazolo[4,3-d]pyrimidin-5-yl)-6-propoxy-3-pyridinyl]amino}acetic acid;

N-[5-(1-Methyl-7-oxo-3-propyl-6,7-dihydro-1H-pyrazolo[4,3-d]pyrimidin-5-yl)-6-propoxy-3-pyridinylmethanesulfonamide;

N-[5-(1-Methyl-7-oxo-3-propyl-6,7-dihydro-1H-pyrazolo[4,3-d]pyrimidin-5-yl)-6-propoxy-3-pyridinyl]-3-oxo-β-alanine;

({[5-(1-Methyl-7-oxo-3-propyl-6,7-dihydro-1H-pyrazolo[4,3-d]pyrimidin-5-yl)-6-propoxy-3-pyridinyl]amino}sulfonyl)acetic acid;

N-[5-(1-Methyl-7-oxo-3-propyl-6,7-dihydro-1H-pyrazolo[4,3-d]pyrimidin-5-yl)-6-propoxy-3-pyridinyl]alanine;

5-{2-[2-(Dimethylamino)ethyl]-3-ethyl-7-oxo-6,7-dihydro-2H-pyrazolo-[4,3-d]pyrimidin-5-yl}-6-ethoxynicotinic acid; and 5-{2-[2-(Dimethylamino)ethyl]-3-ethyl-7-oxo-6,7-dihydro-2H-pyrazolo-[4,3-d]pyrimidin-5-yl}-6-ethoxy-N-methoxy-N-methylnicotinamide.

An especially preferred group of compounds according to the present invention have the general formula (I) wherein:

X represents O or $NR^5$;

$R^1$ represents lower alkyl or alkylHet, which are optionally substituted and/or terminated with one or more substituents selected from lower alkyl, or $NR^{12}R^{13}$;

$R^2$ represents lower alkyl, Het or aryl which are optionally substituted and/or terminated with one or more substituents as defined hereinbefore;

$R^3$ represents $C_1$–$C_4$ alkyl or $C_3$–$C_4$ cycloalkyl which are optionally substituted and/or terminated with one or more $OR^6$ substitutents;

$R^4$ represents halo, cyano, $C(O)R^8$, $C(O)NR^{10}R^{11}$, $NR^{12}R^{13}$, $NR^{16}Y(O)R^{17}$, $SO_2R^{19}$ or aryl, wherein said aryl group is optionally substituted and/or terminated with one or more substituents as defined herienbefore;

and wherein Y, A, Z, $R^{10}$, $R^{11}$, $R^{12}$, $R^{13}$, $R^{16}$, $R^{17}$, $R^5$, $R^6$, $R^8$, $R^{19}$ and Het are as herein before defined.

The compounds of the invention may exhibit tautomerism. All tautomeric forms of the compounds of formulae I, IA and IB, and mixtures thereof, are included within the scope of the invention.

The compounds of the invention may contain one or more chiral centres and therefore can exist as stereoisomers, i.e. as enantiomers or diastereomers, as well as mixtures thereof. The individual stereoisomers of the compounds of formulae IA and IB, as well as any mixtures thereof, are included within the scope of the invention. Diasterebisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. All stereoisomers are included within the scope of the invention.

Also included within the scope of the invention are radiolabelled derivatives of compounds of formulae I, IA and IB which are suitable for biological studies.

The present invention additionally provides compounds of the general formulae (IA) and (IB) or a pharmaceutically or veterinarily acceptable salts and/or solvates thereof, wherein X represents O or $NR^5$ $R^1$ represents H, lower alkyl, Het, alkylHet, aryl or alkylaryl, which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$ $R^2$ represents H, halo, cyano, nitro, $OR^6$, $OC(O)R^7$, $C(O)R^8$, $C(O)OR^9$, $C(O)NR^{10}R^{11}$, $NR^{12}R^{13}$, $SO_2NR^{14}R^{15}$, lower alkyl, Het, alkylHet, aryl or alkylaryl, which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{13}R^{14}$ and $SO_2NR^{14}R^{15}$ $R^3$ represents H, lower alkyl, alkylHet or alkylaryl, which latter three groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$ $R^4$ represents H, halo, cyano, nitro, halo(loweralkyl), $OR^6$, $OC(O)R^7$, $C(O)R^8$, $C(O)OR^9$, $C(O)NR^{10}R^{11}$, $NR^{12}R^{13}$, $NR^{16}Y(O)R^{17}$, $SOR^{18}$, $SO_2R^{19}R^{20}$, $C(O)AZ$, lower alkyl, lower alkenyl, lower alkynyl, Het, alkylHet, aryl, alkylaryl, which latter seven groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$ Y represents C or S(O), wherein one of $R^{16}$ and $R^{17}$ is not present when Y is S(O)

A represents lower alkylene

Z represents $OR^6$, halo, Het or aryl, which latter two groups are both optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$ $R^5$, $R^6$, $R^7$, $R^8$, $R^9$, $R^{18}$, $R^{19}$ and $R^{20}$ independently represent H or lower alkyl $R^{10}$ and $R^{11}$ independently represent H or lower alkyl, which latter group is optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{10}R^{11}$ and $SO_2NR^{13}R^{15}$ or Het or aryl optionally substituted with one or more of said latter eleven groups or one of $R^{10}$ and $R^{11}$ may be lower alkoxy, amino or Het, which latter two groups are both optionally substituted with lower alkyl $R^{12}$ and $R^{13}$ independently represent H or lower alkyl or one of $R^{12}$ or $R^{13}$ may be C(O)-lower alkyl or C(O)Het in which Het is optionally substituted with lower alkyl $R^{14}$ and $R^{15}$ independently represent H or lower alkyl or $R^{14}$ and $R^{15}$, together with the nitrogen atom to which they are bound, form a heterocyclic ring $R^{16}$ and $R^{17}$ independently represent H or lower alkyl or one of $R^{16}$ and $R^{17}$ may be Het or aryl, which latter two groups are both optionally substituted with lower alkyl Het represents an optionally substituted four to twelve membered heterocyclic group, which may be aromatic or non-aromatic, which may contain one or more double bonds, which may be mono- or bi-cyclic and which contains one or more heteroatoms selected from N, S and O.

Preparation

According to a further aspect of the invention there is provided processes for the preparation of compounds of the invention, as illustrated below.

The following processes are illustrative of the general synthetic procedures which may be adopted in order to obtain the compounds of the invention:

1. Compounds of formulae I, IA and IB may be prepared by cyclisation of corresponding compounds of formulae II, IIA and IIB, respectively:

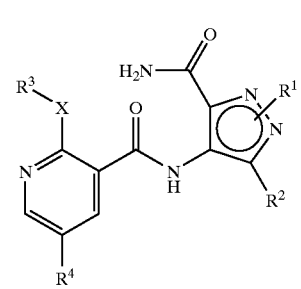

II

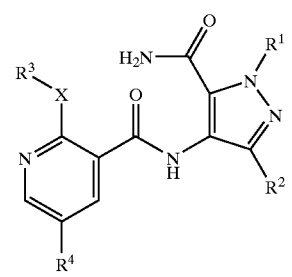

IIA

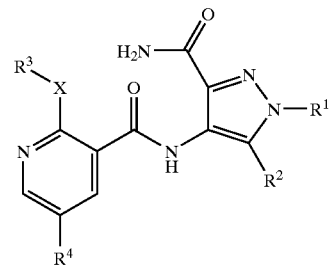

IIB wherein $R^1$, $R^2$, $R^3$, $R^4$ and X are as defined previously for compounds of formulae I, IA and IB.

This cyclisation may be accomplished under basic, neutral or acidic conditions using known methods for pyrimidone ring formation. Preferably, the cyclisation is performed under basic conditions using an alkali metal salt of an alcohol or amine, such as sodium ethoxide, potassium tert-butoxide, cesium carbonate or potassium bis(trimethylsilyl)amide, in the presence of a suitable alcoholic solvent, such as ethanol, for example at reflux temperature (or, if performed in a sealed vessel, at greater than reflux temperature). The skilled person will appreciate that, when X represents O and an alcohol is selected as solvent, an appropriate alcohol of formula $R^3OH$, or a sterically hindered alcohol, e.g. 3-methyl pentan-3-ol, may be used if it is intended to mitigate alkoxide exchange at the 2-position of the pyridin-3-yl.

Compounds of formulae II, IIA and IIB may be prepared by reaction of corresponding compounds of formulae III, IIIA and IIIB, respectively:

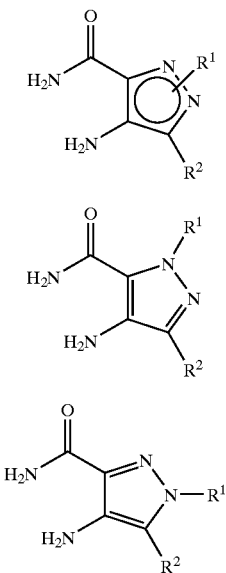

wherein $R^1$ and $R^2$ are as defined previously for compounds of formulae II, IIA and IIB, with a compound of formula IV or a carboxylic acid derivative thereof:

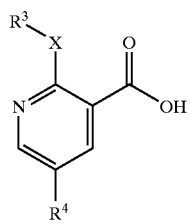

wherein $R^3$, $R^4$ and X are as defined previously for compounds of formula II, IIA and IIB.

This coupling reaction may be achieved by conventional amide bond forming techniques which are well known to those skilled in the art. For example, an acyl halide (e.g. chloride) derivative of a compound of formula IV may be reacted with a compound of formula II, IIIA or IIIB in the presence of an excess of a tertiary amine, such as triethylamine or pyridine, optionally in the presence of a suitable catalyst, such as 4-dimethylaminopyridine, in a suitable solvent such as dichloromethane or THF, at a temperature of about 0° C. to room temperature.

A variety of other amino acid coupling methodologies may be used to couple the compounds of formulae II, IIIA or IIIB with the compound of formula IV. For example, the acid of formula IV or a suitable salt thereof (e.g. sodium salt) may be activated with an appropriate activating reagent, e.g. a carbodiimide, such as 1,3-dicyclohexylcarbodiimide or 1-(3-dimethylaminopropyl)-3-ethylcarbodiimide hydrochloride optionally in the presence of 1-hydroxybenzotriazole hydrate and/or a catalyst such as 4-dimethylaminopyridine; a halotrisaminophosphonium salt such as bromo-tris(pyrrolidinyl)phosphonium hexafluorophosphate; a suitable pyridinium salt such as 2-chloro-1-methyl pyridinium chloride; or another suitable coupling agent such as O-(7-azabenzotriazol-1-yl)-N,N,N',N'-tetramethyluronium hexafluorophosphate (HATU). Either type of coupling reaction may be conducted in a suitable solvent such as dichloromethane, tetrahydrofuran or N,N-dimethylformamide, optionally in the presence of a tertiary amine such as N-methylmorpholine or N-ethyldiisopropylamine (for example when either the compound of formula III, IIIA or IIIB, or the activating agent is presented in the form of an acid addition salt), at from about 0° C. to about room temperature. Preferably, from about 1 to 2 molecular equivalents of the activating reagent and from 1 to 3 molecular equivalents of any tertiary amine present may be employed.

Alternatively, the carboxylic acid function of IV may be activated using an excess of a reagent such as N,N-carbonyldiimidazole in an appropriate solvent, e.g. ethyl acetate, dichloromethane or butan-2-one, at from about room temperature to about 80° C., followed by reaction of the intermediate imidazolide with either a compound of the formula II, IIIA or IIIB at from about 20° C. to about 90° C.

In a further variation, a compound of formula I, IA or IB, as defined previously, may be formed in a one-pot procedure by coupling a compound of formula III, IIIA or IIIB with the acyl chloride derivative of formula IV and by cyclising the resultant intermediate compound of formula II, IIA or IIB, using the methods as described previously. The one-pot procedure may further involve an in-situ coupling and cyclisation reaction to form a compound of formula I, IA or IB. Preferably, pyridine may serve as an acid scavenger and as the solvent for the in-situ coupling and cyclisation reaction.

According to preferred processes of the present invention, a compound of formula I, IA or IB, as defined previously, may be formed in a one-pot procedure as defined hereinbefore by coupling a compound of formula III, IIIA or IIIB with an acid derivative of formula IV and by cyclising the resultant intermediate compound of formula II, IIA or IIB, using the methods as described previously wherein the acid derivative of formula IV is formed from an ester of general formula (XXX) which itself is prepared either from a compound of general formula (XXXI) which is obtained from a compound of general formula (XXXII):

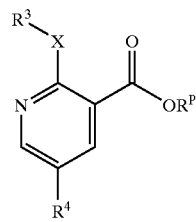

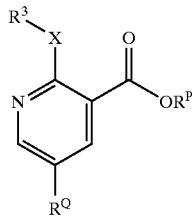

XXXII

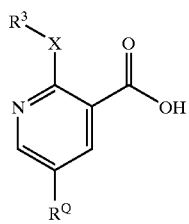

or wherein IV is formed directly from a compound of general formula (XXXII) wherein $R^P$ is $C_1$ to $C_6$ alkyl, preferably methyl or ethyl and wherein $R^Q$ is a halogen, selected from Cl, Br and I, and is preferably I. These preferred processes according to the present invention are exemplified herein in Preparations 37, 56, 57, 58, 59, 61 and Example 129 herein. It is to be understood that the direct formation of IV from (XXXII) is the most preferred route.

In the above preferred processes preferred compounds of formulae (IV), (XXX), (XXXI) and (XXXII) are used wherein $R^3$ is lower alkyl, preferably $C_2$ to $C_4$, X is O, $R^Q$ is a halogen, preferably Br or I, $R^P$ is a protecting group for an acid and is preferably a lower alkyl group such as methyl or ethyl or t-butyl, and $R^4$ is acyl, preferably acetyl.

Compounds of formulae II, IIA and IIB may alternatively be prepared by alkylation of corresponding compounds of formulae XXIII, XXIIIA or XXIIIB, respectively, as defined hereinafter, for example under conditions such as those described hereinafter in respect of the preparation of compounds of formulae I, IA and IB (see process 5).

2. Compounds of formulae I, IA and IB, in which $R^2$ represents $C(O)NR^{10}R^{11}$, and $R^{10}$ and $R^{11}$ are as defined previously for compounds of formulae I, IA and IB, may be prepared by reaction of corresponding compounds of formulae I, IA and IB, in which $R^2$ represents C(O)OH (or a carboxylic acid derivative thereof) with a compound of formula $HNR^{10}R^{11}$, in which $R^{10}$ and $R^{11}$ are as previously defined for compounds of formulae I, IA and IB.

This reaction may be accomplished using analogous amide bond forming techniques to those previously described for compounds of formulae II, IIA and IIB.

Compounds of formulae I, IA and IB, in which R represents $C(O)OR^9$, may be prepared by cyclisation of corresponding compounds of formulae VI, VIA and VIB, respectively:

VI

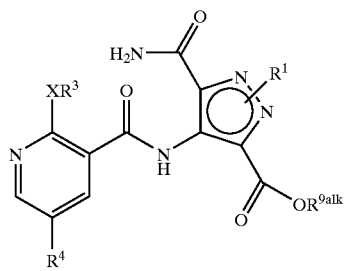

VIA

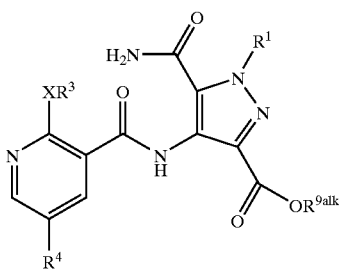

VIB

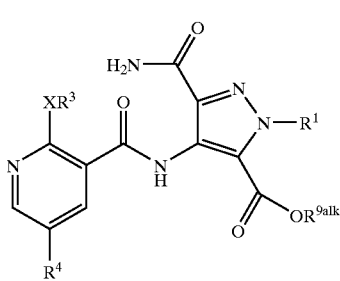

wherein $R^1$, $R^3$, $R^4$ and X are as defined previously for compounds of formulae I, IA and IB, and $R^{9alk}$ represents an optionally substituted lower alkyl group, as defined hereinbefore, followed by removal of the alkyl group $R^{9alk}$ (if required) by hydrolysis and/or (if required) exchange with a further optionally substituted alkyl group.

Typically, the cyclisation reaction is accomplished using analogous methods to those previously described for compounds of formulae II, IIA and IIB.

Compounds of formulae VI, VIA and VIB may be prepared by reaction of corresponding compounds of formulae VII, VIIA and VIIB, respectively:

VII

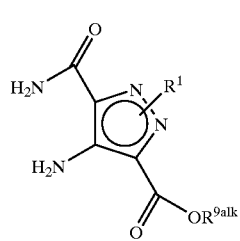

VIIA

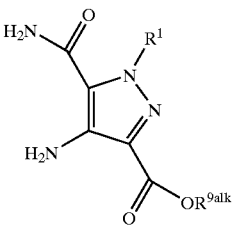

VIIB

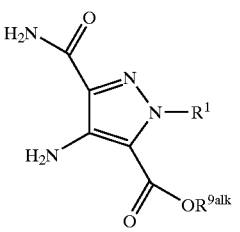

wherein $R^1$ and $R^{9alk}$ are as defined previously for compounds of formulae VI, VIA and VIB, with a compound of formula IV as defined hereinbefore. The reaction may be accomplished using analogous amide coupling conditions to those described previously in relation to compounds of formulae II, IIA and IIB.

Compounds of formulae I, IA and IB, in which $R^4$ is, for example, lower alkoxycarbonyl (such as methoxycarbonyl), lower alkynyl (such as o acetylenyl), lower acyl (such as acetyl), Het or aryl, which latter four groups are optionally substituted, may be prepared by reaction of corresponding compounds of formulae VIII, VIIIA and VIIIB, respectively:

VIII

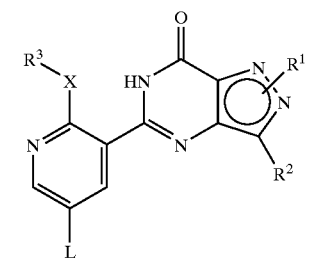

VIIIA

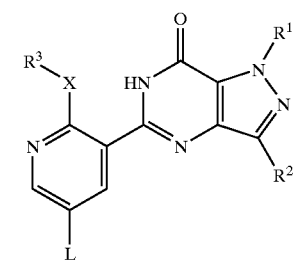

VIIIB

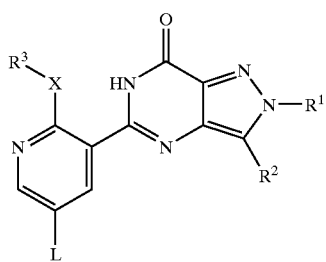

wherein L is a leaving group, such as halo, preferably bromo or iodo, and $R^1$, $R^2$, $R^3$ and X are as previously defined for compounds of formulae I, IA and IB, with a compound containing a group $R^{4a}$ which is capable of exchanging for L. $R^{4a}$ may be lower alkoxycarbonyl (such as methoxycarbonyl), lower alkynyl (such as acetylenyl), lower acyl (such as acetyl), Het, aryl (which latter four groups are optionally substituted), or, alternatively, $R^{4a}$ may be a group that is equivalent to (e.g. a tautomer of) any of the latter five groups. Conventional coupling chemistry, carbonylation chemistry or halogen metal exchange may be used in this reaction. In addition to the process conditions described in the processes hereinafter, suitable coupling conditions include:

(a) so-called "Suzuki" conditions (e.g. 1.2 eq. of boronic acid, 2 eq. of $K_2CO_3$ and 0.1 eq. of $Pd(PPh_3)_4$, refluxing in an approximately 4:1 mixture of dioxane:water, or 2.5 to 3 eq. of CsF, 0.05 to 0.1 eq. of $Pd_2(dba)_3$ and 0.01 to 0.04 eq of $P(o\text{-tol})_3$, refluxing in DME);

(b) so-called "Stille" conditions (e.g. 1.5 eq. of stannane, 10 eq. of LiCl, 0.15 eq. of CuI, and 0.1 eq. of $Pd(PPh_3)_4$, refluxing in dioxane, or 5 eq. of stannane, 3.6 eq. of $Et_3N$, $Pd_2(dba)$ and $P(o\text{-tol})_3$, refluxing in MeCN);

(c) so-called "Heck" conditions (e.g. 2 eq. of a source of an acyl anion equivalent (such as butyl vinyl ether), 1.7 eq. of $Et_3N$ and catalytic amounts of $Pd(OAc)_2$ and $P(o\text{-tol})_3$, in MeCN at between room temperature and reflux); or (d) so-called "Sonogashira" conditions (for example as described in Synthesis 1980, 8, 627, such as 1.5 to 5 eq. of a terminal alkyne and 0.024 to 0.03 eq. of $Pd(PPh_3)_2Cl_2/CuI$, in $Et_3N$ and MeCN at between room temperature and 60° C.).

(e) Ni-catalysed conversion of an aryliodide to an S-linked isothiourea derivative which can be further transformed to a sulphoxide or a sulphone. Such conditions are described, for example, in Chemistry Letters, 1998, p 1979.

Suitable carbonylation conditions include reaction of a compound of formula VIII, VIIIA or VIIIB in which L represents halo with an appropriate palladium catalyst system (e.g. palladium(II) acetate combined with 1,2-bis(diphenylphosphino)propane (DPPP)) under an atmosphere of carbon monoxide (e.g. at a pressure of around 482.6 kPa (70 psi)) in the presence of an excess of a lower alkyl alcohol (e.g. methanol), an excess of a tertiary amine base (e.g. $Et_3N$), and optionally in the presence of a suitable solvent (e.g. dimethylsulfoxide).

Group $R^{4a}$ may be a group $R^4$, as defined in formulae I, IA and IB. Alternatively, $R^{4a}$ may be converted to a group $R^4$ or to another group $R^4$ using conventional chemical techniques. Examples of such conversions of groups $R^{4a}$ to $R^4$ and interconversions of groups $R^4$ are given in the Examples set out hereinafter.

Compounds of formula VIII, VIIIA and VIIIB may be prepared from corresponding compounds of formulae X, XA and XB, respectively:

X

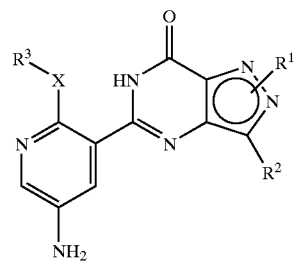

XA

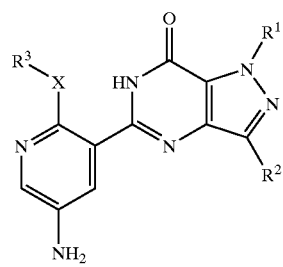

-continued

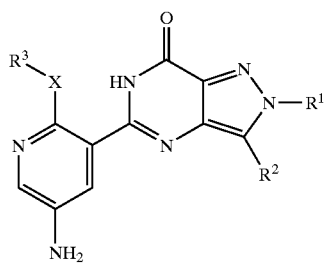
XB wherein $R^1$, $R^2$, $R^3$ and X are as previously defined for compounds of formulae VIII, VIIIA and VIIIB, using methods known to those skilled in the art for converting an amino group to an L group, in which L is as previously defined for compounds of formulae VIII, VIIIA and VIIIB. L may be Hal, wherein Hal is iodo, bromo or chloro. For example, compounds of formulae VIII, VIIIA and VIIIB in which L is iodo may be prepared by lo reacting a corresponding compound of formula X, XA or XB with about a 4 to 5-fold excess of butyl nitrite in diiodomethane.

Compounds of formulae X, XA and XB may be prepared by cyclisation of corresponding compounds of formulae XI, XIA and XIB, respectively:

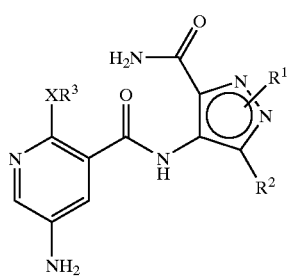
XI

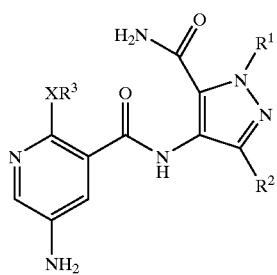
XIA

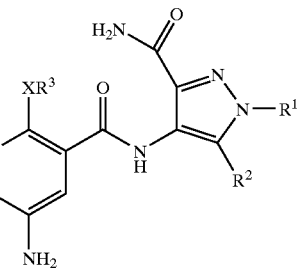
XIB wherein $R^1$, $R^2$, $R^3$ and X are as previously defined for compounds of formulae X, XA and XB. This cyclisation may be carried out using similar techniques to those described hereinbefore for the preparation of compounds of formulae II, IIA and IIB, but it is preferably base mediated. Compounds of formulae XI, XIA and XIB may be prepared by the reduction of corresponding compounds of formulae XII, XIIA and XIIB, respectively:

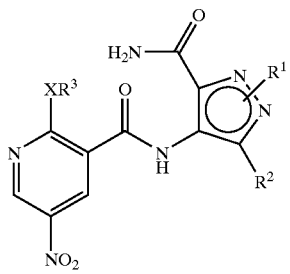
XII

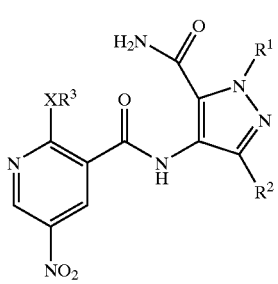
XIIA

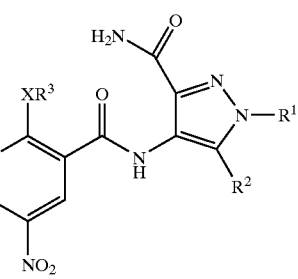
XIIB wherein $R^1$, $R^2$, $R^3$ and X are as defined previously for compounds of formulae XI, XIA and XIB, by conventional techniques, such as catalytic hydrogenation. Typically, the hydrogenation may be achieved using a Raney® nickel catalyst in a suitable solvent such as ethanol at a hydrogen pressure of about 150 kPa to 500 kPa, especially 345 kPa, at from about 40° C. to about 50° C.

Compounds of formulae XII, XIIA and XIIB may be prepared by reaction of corresponding compounds of formulae II, IIIA and IIIB as defined hereinbefore, with a compound of formula XIII:

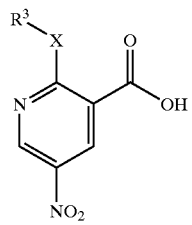
XIII wherein $R^3$ and X are as previously defined for compounds of formulae XII, XIIA and XIIB. The reaction may be achieved using analogous amide bond forming techniques to those previously described for compounds of formulae II, IIA and IIB.

Compounds of formulae X, XA and XB may alternatively be prepared by reduction of corresponding compounds of formulae XIII, XIIIA and XIIIB, respectively:

XIII

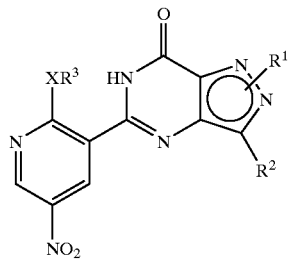

XIIIA

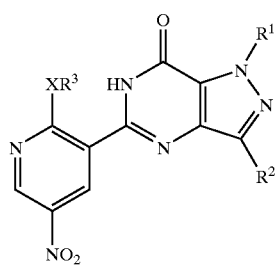

XIIIB

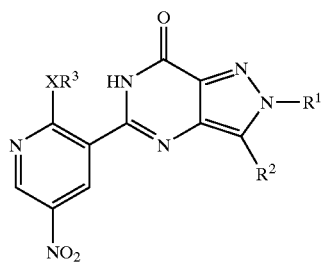

wherein $R^1$, $R^2$, $R^3$ and X are as previously defined for compounds of formulae X, XA and XB. This reduction may be performed under a variety of reaction conditions, for example by catalytic hydrogenation (for example using: 10% Pd/C in an alcohol, such as ethanol, at 60 psi (415 kPa) $H_2$ pressure and room temperature; or Raney® nickel in a suitable solvent such as ethanol at a hydrogen pressure of about 150 kPa to 500 kPa, especially 345 kPa, and at from about 40° C. to about 50° C.) or by transition metal catalysed reduction (e.g. at around room temperature in the presence of iron powder (e.g. 7 eq.) in acetic acid, or $TiCl_3$ (e.g. 9 eq.) in acetic acid).

Compounds of formulae XIII, XIIIA and XIIIB may be prepared by reaction of a compound of formula XIIIC,

XIIIC

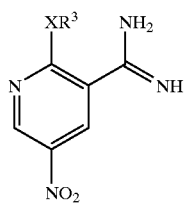

or, preferably, a carboxylic acid addition salt thereof (e.g. an acetate or a formate), wherein X and $R^3$ are as previously defined for compounds of formulae XIII, XIIIA and XIIIB, with either:
(a) a corresponding compound of formula III, IIIA or formula IIIB, as defined hereinbefore; or
(b) a corresponding compound of formula XVII, XVIIA or formula XVIIB, as defined hereinafter, in both cases under conditions such as those described herein. Such reactions may be carried out, for example, using 1.0 to 1.1 equivalents of the amidine compound of formula XIIIC, for example by refluxing in 3-methyl-3-pentanol (e.g. for about 2.5 to 3 hours).

Compounds of formula XIIIC may be prepared from the corresponding cyanopyridine under conditions well known to those skilled in the art.

Compounds of formulae XIII, XIIIA and XIIIB in which $R^2$ represents lower alkyl (which alkyl group is branched and unsaturated at the carbon atom that is attached to the rest of the molecule), lower alkoxycarbonyl, $NR^{12}R^{13}$, cyano, aryl or Het (which Het group is either aromatic or is unsaturated at the carbon atom that is attached to the rest of the molecule) may alternatively be prepared from corresponding compounds of formulae XIIID or XIIIE, respectively:

XIIID

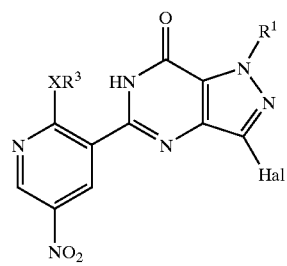

XIIIE

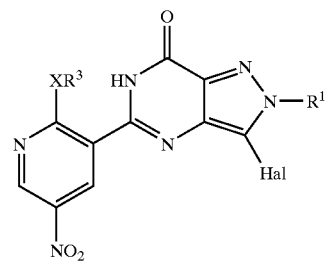

wherein Hal represents Cl, Br or I, preferably I and especially Br, and $R^1$, $R^3$ and X are as previously defined for compounds of formulae XII, XIIIA and XIIIB, for example as described hereinafter for preparation of compounds of formulae I, IA and IB (see process 6 below). In addition to the process conditions described in process 6 below, suitable coupling conditions include:
(a) so-called "Suzuki" conditions (e.g. 1.2 eq. of boronic acid, 2 eq. of $K_2CO_3$ and 0.1 eq. of $Pd(PPh_3)_4$, refluxing in an approximately 4:1 mixture of dioxane:water, or 2.5 to 3 eq. of CsF, 0.05 to 0.1 eq. of $Pd_2(dba)_3$ and 0.01 to 0.04 eq of $P(o-tol)_3$, refluxing in DME);
(b) so-called "Stille" conditions (e.g. 1.5 eq. of stannane, 10 eq. of LiCl, 0.15 eq. of CuI, and 0.1 eq. of $Pd(PPh_3)_4$, refluxing in dioxane, or 5 eq. of stannane, 3.6 eq. of $Et_3N$, $Pd_2(dba)$ and $P(o-tol)_3$, refluxing in MeCN);
(c) so-called "Heck" conditions (e.g. 2 eq. of a source of an acyl anion equivalent (such as butyl vinyl ether), 1.7 eq. of $Et_3N$ and catalytic amounts of $Pd(OAc)_2$ and $P(o-tol)_3$, in MeCN at between room temperature and reflux); or
(d) so-called "Sonogashira" conditions (for example as described in *Synthesis* 1980, 8, 627, such as 1.5 to 5 eq. of a terminal alkyne and 0.024 to 0.03 eq. of $Pd(PPh_3)_2$ $Cl_2$/CuI, in $Et_3N$ and MeCN at between room temperature and 60° C.).

Suitable carbonylation conditions include reaction of a compound of formula XIIID or XIIIE with an appropriate palladium catalyst system (e.g. palladium(II) acetate combined with 1,2-bis(diphenylphosphino)-propane (DPPP)) under an atmosphere of carbon monoxide (e.g. at a pressure of around 482.6 kPa (70 psi)) in the presence of an excess of a lower alkyl alcohol (e.g. methanol), an excess of a tertiary amine base (e.g. Et₃N), and optionally in the presence of a suitable solvent (e.g. dimethylsulfoxide).

Compounds of formula XIIID and XIIIE may be prepared by halogenation of corresponding compounds of formulae XIIIF and XIIIG, respectively:

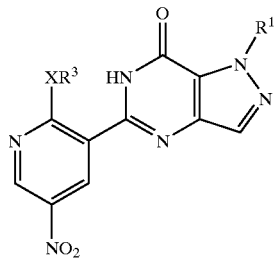

XIIIF

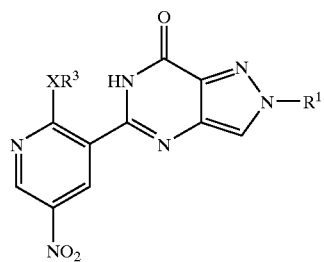

XIIIG wherein $R^1$, $R^3$ and X are as hereinbefore defined, under conditions known to those skilled in the art (e.g., for bromination, at between room temperature and reflux in the presence of acetic acid as solvent, 1.5 to 2.0 eq. of bromine and e.g. 1.5 to 2.0 eq. of sodium acetate).

Compounds of formulae XIII, XIIIA and XIIIB may be prepared by coupling corresponding compounds of formulae XVII, XVIIA and XVIIB, respectively:

XVII

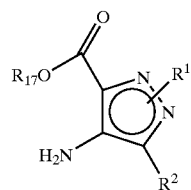

XVIIA

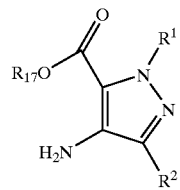

XVIIB

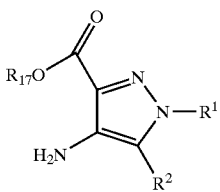

wherein $R^1$ and $R^2$ are as previously defined for compounds of formulae XVI, XVIA and XVIB and $R^{17}$ represents a lower (e.g. $C_{1-6}$ alkyl) group, to with a compound of formula XIIIC.

5. Compounds of formulae I, IA and IB in which $R^1$ represents lower alkyl, Het, aryl, alkylHet or alkylaryl (which latter five groups are all optionally substituted as defined hereinbefore in respect of $R^1$) may be prepared by alkylation of corresponding compounds of formulae XXIIA or XXIIB, respectively (which the skilled person will appreciate are different tautomeric forms of the same compound):

XXIIA

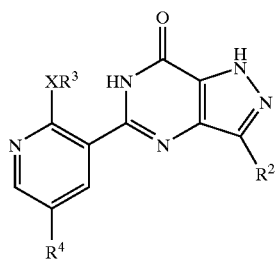

XXIIB

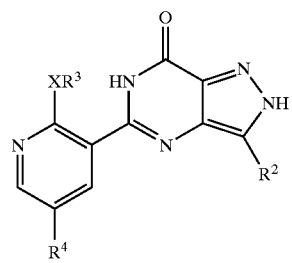

wherein $R^2$, $R^3$, $R^4$ and X are as previously defined for compounds of formulae I, IA and IB, for example by reaction under conditions known to those skilled in the art with a compound of formula $R^{1a}$—L, wherein $R^{1a}$ represents lower alkyl, Het, aryl, alkylHet or alkylaryl (which latter five groups are all optionally substituted as defined hereinbefore in respect of $R^1$) and L and Het are as hereinbefore defined. The skilled person will appreciate that compounds of formulae XXIIA and XXIIB are, respectively, compounds of formulae I, IA and IB in which $R^1$ represents H.

Compounds of formulae XXIIA and XXIIB may be prepared by cyclisation of corresponding compounds of formulae XXIIIA and XXIIIB, respectively:

XXIIIA

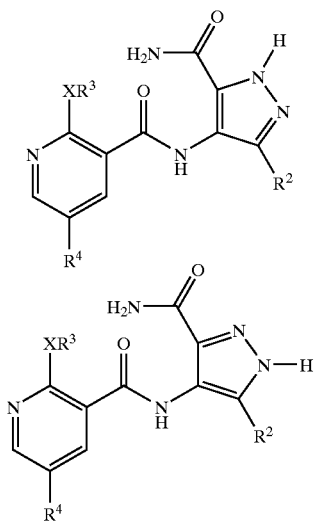

XXIIIB wherein $R^2$, $R^3$, $R^4$ and X are as hereinbefore defined, for example under conditions equivalent or analogous to those described hereinbefore in respect of the preparation of compounds of formulae I, IA and IB.

6. Compounds of formulae I, IA and IB, in which $R^2$ represents optionally substituted lower alkyl (which alkyl group is branched and unsaturated at the carbon atom that is attached to the rest of the molecule), $NR^{12}R^{13}$, cyano, aryl or Het (which Het group is either aromatic or unsaturated at the carbon atom that is attached to the rest of the molecule), may be prepared by cross-coupling of corresponding compounds of formula XXIV, XXIVA and XXIVB:

XXIV

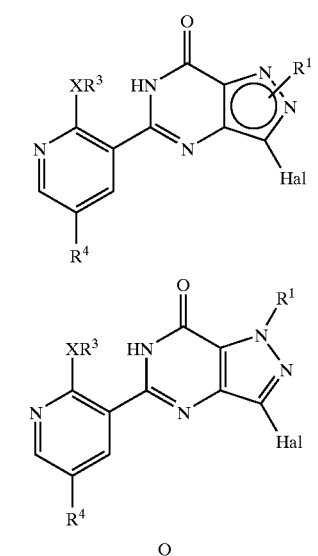

XXIVA

XXIVB wherein Hal, $R^1$, $R^3$, $R^4$ and X are as hereinbefore defined, using a compound of formula $R^{2a}M$ wherein $R^{2a}$ represents optionally substituted lower alkyl (which alkyl group is branched and unsaturated at the carbon atom that is attached to M), $NR^{12}R^{13}$, cyano, aryl or Het (which Het group is either aromatic or unsaturated at the carbon atom that is attached to M), $R^{12}$ and $R^{13}$ are as hereinbefore defined and M represents an optionally substituted metal or boron group, which group is suitable for cross-coupling reactions, for example a trialkylstannane (e.g. tri-n-butylstannane), a dialkylborane (e.g. diethylborane), a dialkoxy borane, a dihydroxyborane, lithium, a halomagnesium, a halozinc, copper, a halomercury, in the presence of an appropriate catalyst system (e.g. a palladium or nickel catalyst).

The cross-coupling reaction is preferably carried out in the presence of a base (e.g. potassium carbonate, cesium fluoride or triethylamine), preferably in excess. Those skilled in the art will appreciate that the type of catalyst that is employed will depend on factors such as the nature of the M group, the substrate that is employed etc.

Typical procedures that may be employed include those described hereinafter. In a further typical procedure, a compound of formula $R^{2a}M$ may be used, in which M is halozinc. Such a compound may be prepared by reaction of a compound $R^2Hal$, where Hal and $R^2$ are as hereinbefore defined, with an alkyllithium (e.g. n-butyllithium) at a temperature of between −78° C. and room temperature, in a suitable solvent (e.g. THF), and the resultant solution is then treated with $Zn(II)Cl_2$ (solution in ether) and the resultant solution is treated with a compound of formula XXIV, XXIVA or XXIVB in the presence of a palladium catalyst (e.g. tetrakis(triphenyl-phosphine)palladium(0)) in a suitable solvent (e.g. THF). The reaction may be carried out at from room temperature to reflux temperature.

Suitable coupling conditions also include so-called Suzuki and Stille conditions such as those described hereinbefore in respect of preparation of compounds of formulae XXIII, XIIIA and XIIIB, The skilled person will appreciate that compounds of formulae I, IA and IB in which $R^2$ represents lower alkyl that is branched, but not unsaturated, at the carbon atom that is attached to the rest of the molecule may be prepared by in this way, provided that the corresponding compound of formula I, IA or IB in which the corresponding $R^2$ group is unsaturated is subsequently hydrogenated under conditions known to those skilled in the art.

Compounds of formulae XXIV, XXIVA and XXIVB may be prepared by cyclisation of corresponding compounds of formulae XXV, XXVA and XXVB, respectively:

XXV

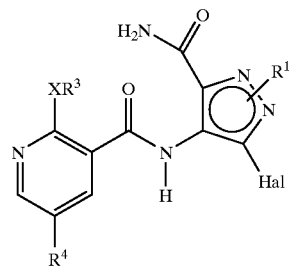

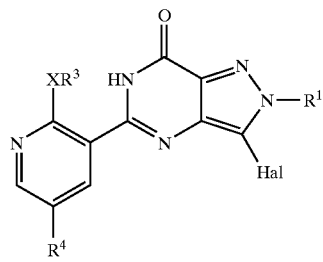

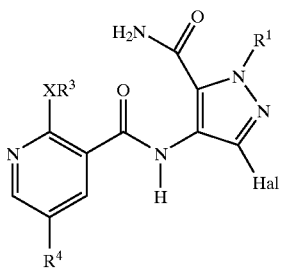

XXVA

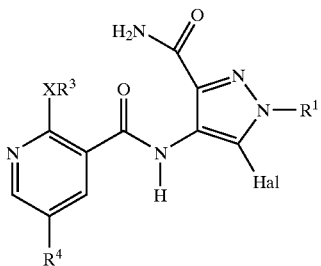

XXVB in which R¹, R³, R⁴, X and Hal are as hereinbefore defined, for example under analogous reaction conditions to those described hereinbefore for compounds of formulae II, IIA and IIB.

Compounds of formulae XXV, XXVA and XXVB may be prepared analogously to methods described herein, for example coupling of a compound of formula IV, as hereinbefore defined, to an appropriate 4-amino-3-halopyrazole-5-carboxamide, which pyrazole compound may, in turn, be prepared by halogenation of a corresponding 4-aminopyrazole-5-carboxamide, under conditions which are well known to those skilled in the art.

Compounds of formulae XXIV, XXIVA and XXIVB may alternatively be prepared from corresponding compounds of formulae XXVI, XXVIA and XXVIB, respectively:

XXVI

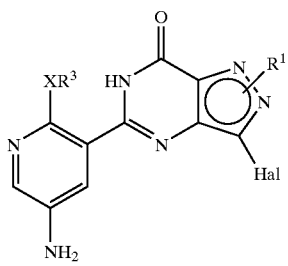

XXVIA

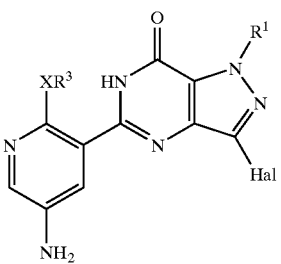

XXVIB

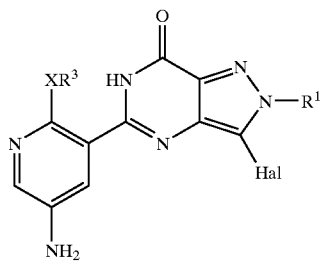

wherein X, Hal, R¹ and R³ are as hereinbefore defined, for example as described hereinbefore for preparation of compounds of formulae I, IA and IB from compounds of formulae X, XA and XB (via compounds of formulae VIII, VIIIA and VIIIB; see process 4 above).

Compounds of formulae XXVI, XXVIA and XXVIB may be prepared via routine techniques (for example, reduction of corresponding nitropyridine compounds of formulae XIIID and XIIIE as defined herein, respectively, using for example the methods for the reduction of compounds of formulae XXII, XIIA and XIIB as described herein).

7. Compounds of formulae I, IA and IB in which $R^2$ represents lower acyl (e.g. acetyl), lower alkoxycarbonyl (e.g. methoxycarbonyl) or lower alkynyl may be prepared by a cross-coupling reaction between corresponding compounds of formulae XXIV, XXIVA and XXIVB, respectively, as defined above, and a reagent or reagents capable of delivering the lower acyl, lower alkoxycarbonyl or lower alkynyl group (or groups equivalent to (e.g. tautomers of) these). Suitable cross-coupling conditions include the Heck, Sonogashira and palladium-catalysed carbonylation conditions described at process 4 above.

Compounds of formulae III, IIIA and IIIB, IV, VII, VIIA and VIIB, XIII, XIIIF and XIIIG, XXIII, XXIIIA and XXIIIB, compounds of formulae $HNR^{12}R^{13}$, $R^{2a}M$, $R^3OH$, and $R^{1a}$—L, other compounds mentioned hereinbefore, and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions.

Substituents on the aryl and Het groups in the above-mentioned compounds may be introduced, and interconverted, using techniques which are well known to those skilled in the art.

The skilled person will also appreciate that various standard substituent or functional group interconversions and transformations within certain compounds of formulae I, IA and IB will provide other compounds of formulae I, IA and IB. For example, when X is $NR^5$, the compounds of formulae I, IA and IB in which X is O may be treated with an excess of $R^3R^5NH$, or a suitable acid addition salt thereof, in the presence of an excess of a sterically hindered amine in a suitable solvent. Typically, $R^3R^5NH$ is used as the free base with about a 3-fold excess (over the substrate) of potassium bis(trimethylsilyl)amide (KHMDS) in dimethylformamide (DMF) as solvent at about 100° C. Alternatively, an excess of $R^3R^5NH$ may be used as the solvent and the reaction conducted in the presence of about a 50% excess of copper(II) sulfate at up to the reflux temperature of the reaction medium. Where the desired amino substituent on the compound of the formula I, IA or IB is —$NR^3R^5$ and one of either $R^3$ or $R^5$ is H, then the exchange reaction may be carried out by refluxing with the appropriate amine, a copper(II) sulfate penta- or hepta-hydrate or KHDMS in DMF. Typically, to exchange the $OR^3$ group for alternative amines of the formula $NHR^3R^5$, such as compounds wherein $R^3$ or $R^5$ are selected from aliphatic or cyclic amines, optionally including oxygen, then the reaction is preferably carried out by treating with the appropriate amine and about 8 equivalents of potassium bis(trimethylsilyl)amide in DMF for about 18 hours at 100° C. Further examples when X is O include alkoxide exchange at the 2-position of the pyridin-3-yl substituents, and for compounds in which one or more of $R^1$, $R^2$, $R^3$ and/or $R^4$ represents an alkyl group which is terminated by OH, deprotection of a corresponding ether compound of formula I, IA or IB (see the Examples below). Moreover, certain compounds of formulae I, IA and IB, for example those in which $R^{12}$ and $R^{13}$, together with the nitrogen to which they are attached, form a 4-lower alkyl-piperazinyl group, may be prepared directly from the corresponding piperazine analogues, using standard procedures (e.g. alkylation).

Further standard substituent or functional group interconversions and transformations that may be performed on compounds of formulae I, IA and IB include procedures described hereinafter. In this respect:

(i) alkoxycarbonyl may be hydrolysed to carboxy under acidic or basic conditions;

(ii) amino may be alkylated (either by reaction with an alkylating agent or by reductive alkylation) to give alkylamino or dialkylamino;

(iii) amino may be acylated to give acylamino or sulfonated to give sulfonylamino or disulfonylamino;

(iv) disulfonylamino may be hydrolysed to sulfonylamino under basic conditions;

(v) alkynyl may be hydrolysed to acyl in the presence of a catalyst such as a mercury(II) salt;

(vi) alkynyl may be oxidised to α-hydroxy acyl in the presence of an oxidising agent such as a phenyliodine (III) bis(trifluoroacetate), for example as described in *Tet. Lett.* 1985, 26, 3837;

(vii) hydroxy may be converted to halo by reaction with a halogenating agent;

(viii) halo may be converted to cyano by reaction with a metal cyanide salt (e.g. Cu(I) cyanide); and (ix) enolisable acyl groups may be converted to β-amino acyl by reaction with an aldehyde and an amine under "so called" Mannich conditions.

In addition, certain acyclic groups may be converted to certain heterocyclic groups using reagents and conditions known to those skilled in the art, for example as described in Comprehensive Heterocyclic Chemistry II, edited by A R Katritsky, C W Rees and E F V Scriven, 1$^{st}$ Edition, Elsevier Science Ltd., Volumes 1–11 (1996).

The compounds of the invention may be isolated from their reaction mixtures using conventional techniques.

It will be appreciated by those skilled in the art that, in the course of carrying out the above processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl) and tetrahydropyranyl. Suitable protecting groups for amino include tert-butyloxycarbonyl, 9-fluorenyl-methoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art.

The use of protecting groups is fully described in "Protective Groups in Organic Chemistry", edited by J W F McOmie, Plenum Press (1973), and "Protective Groups in Organic Synthesis", 2$^{nd}$ edition, T W Greene & P G M Wutz, Wiley-Interscience (1991).

Persons skilled in the art will also appreciate that, in order to obtain compounds of formula I, or IA or IB, in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formulae I, IA and IB which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula I, IA or IB with the appropriate base. Both types of salt may be formed or interconverted using ion-exchange resin techniques.

The present invention also includes all suitable isotopic variations of a compound of the formula (I) or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

All protected derivatives, and prodrugs, of compounds of formula I are included within the scope of the invention.

The present invention additionally comprises the combination of a cGMP $PDE_5$ inhibitor compound of the general formula (I), wherein said combination can be administered by sequential, simultaneous or joint administration of a compound of general formula (I) with:

(a) one or more naturally occurring or synthetic prostaglandins or esters thereof. Suitable prostaglandins for use herein include compounds such as alprostadil, prostaglandin $E_1$, prostaglandin $E_0$, 13,14-dihydroprosta glandin $E_1$, prostaglandin $E_2$, eprostinol, natural synthetic and semi-synthetic prostaglandins and derivatives thereof including those described in U.S. Pat. No. 6,037,346 issued on Mar. 14th, 2000 and incorporated herein by reference, $PGE_0$, $PGE_1$, $PGA_1$, $PGB_1$, $PGF_1\alpha$, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3\alpha$, carboprost tromethamine dinoprost, tromethamine, dinoprostone, lipo prost, gemeprost, metenoprost, sulprostune, tiaprost and moxisylate; and/or (b) one or more α-adrenergic receptor antagonist compounds also known as α-adrenoceptors or α-receptors or α-blockers. Suitable compounds for use herein include: the α-adrenergic receptors as described in PCT application WO99/30697 published on June 14th, 1998, the disclosures of which relating to α-adrenergic receptors are incorporated herein by reference and include, selective $\alpha_1$-adrenoceptors or $\alpha_2$-adrenoceptors and non-selective adrenoceptors, suitable $\alpha_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $\alpha_2$-blockers from U.S. Pat. No. 6,037,346 [Mar. 14th, 2000] dibenamine, tolazoline, trimazosin and dibenamine; α-adrenergic receptors as described in US Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $\alpha_2$-Adrenoceptors include: clonidine, papaverine, papaverine hydrochloride, optionally in the presence of a cariotonic agent such as pirxamine; and/or (c) one or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates, (NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075; and/or (d) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, $BaCl_2$; and/or (e) one or more dopaminergic agents. Suitable dopaminergic compounds for use herein include $D_2$-agonists such as, pramipexol; apomorphine; and/or (f) one or more vasodilator agents. Suitable vasodilator agents for use herein include nimodepine, pinacidil, cyclandelate, isoxsuprine, chloroprumazine, halo peridol, Rec 15/2739, trazodone, pentoxifylline; and/or (g) one or more thromboxane A2 agonists; and/or (h) one or more CNS active agents; and/or (i) one or more ergot alkoloids; Suitable ergot alkaloids are described in U.S. Pat. No. 6,037,346 issued on Mar. 14th, 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (k) one or more compounds which modulate the action of atrial natruretic factor (also known as atrial naturetic peptide), such as inhibitors or neutral endopeptidase; and/or (l) one or more compounds which inhibit angiotensin-converting enzyme such as enapril, and combined inhibitors of angiotensin-converting enzyme and neutral endopeptidase such as omapatrilat; and/or (m) one or more angiotensin receptor antagonists such as losartan; and/or (n) one or more substrates for NO-synthase, such as L-arginine; and/or (o) one or more calcium channel blockers such as amlodipine; and/or (p) one or more antagonists of endothelin receptors and inhibitors or endothelin-converting enzyme; and/or (q) one or more cholesterol lowering agents such as statins and fibrates; and/or (r) one or more antiplatelet and antithrombotic agents, e.g. tPA, uPA, warfarin, hirudin and other thrombin inhibitors, heparin, thromboplastin activating factor inhibitors; and/or (s) one or more insulin sensitising agents such as rezulin and hypoglycaemic agents such as glipizide; and/or (t) L-DOPA or carbidopa; and/or (u) one or more acetylcholinesterase inhibitors such as donezipil; and/or (v) one or more steroidal or non-steroidal anti-inflammatory agents.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative), palliative or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which inhibition of a cGMP PDE (e.g. cGMP PDE5) is desirable.

The compounds of the invention are thus expected to be useful for the curative, palliative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury or selective serotonin re-uptake inhibitor (SSRI) induced sexual dysfunction but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, diseases and conditions of the eye such as glaucoma, optic neuropathy, macular degeneration, elevated intra-occular pressure, retinal or arterial occulsion and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful include pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof e.g. gastroparesis, peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction as well as the stabilisation of blood pressure during haemodialysis.

Particularly preferred conditions include MED and FSD.

Thus, the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

Pharmaceutical Preparations

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the inhibition of cGMP-PDEs, such as cGMP-PDE5.

The compounds of the invention, their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the compounds of the invention or salts or solvates hereof can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or pulsatile delivery applications. The compounds of the invention may also be administered via intracavernosal injection. The compounds of the invention may also be administered via fast dispersing or fast dissolving dosages forms or in the form of a high energy dispersion or as coated particles. Suitable pharmaceutical formulations of the compounds of the invention may be in coated or un-coated form as desired.

Such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion or needless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
|---|---|
| Compound of Example 12 | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

Such tablets can be manufactured by standard processes, for example, direct compression or a wet or dry granulation process. The tablet cores may be coated with appropriate overcoats.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention or salts or solvates thereof can be administered in the form of a suppository or pessary, or they may be applied topically in the form of a gel, hydrogel, lotion, solution, cream, ointment or dusting powder. The compounds of the invention or salts or solvates thereof may also be dermally administered. The compounds of the invention or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds of the invention is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus, according to a further aspect of the invention there is provided a pharmaceutical formulation including a compound of the invention in admixture with a pharmaceutically or veterinarily acceptable adjuvant, diluent or carrier.

In addition to the fact that compounds of the invention inhibit cyclic guanosine 3',5'-monophosphate phosphodiesterases (cGMP PDES) and in particular, are potent and selective inhibitors of cGMP PDE5, compounds of the invention may also have the advantage that they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test methods.

Phosphodiesterase (PDE) Inhibitory Activity

The compounds of the present invention are potent and selective cGMP PDE5 inhibitors. In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDEL) from human cardiac ventricle; the cAMP-specific PDE (PDE4) from human skeletal muscle; and the photoreceptor PDE (PDE6) from bovine retina. Phosphodiesterases 7–11 were generated from full length human recombinant clones transfected into SF9 cells.

Assays were performed either using a modification of the "batch" method of W. J. Thompson et al. (Biochem., 1979, 18, 5228) or using a scintillation proximity assay for the direct detection of AMP/GMP using a modification of the protocol described by Amersham plc under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a conc ~1/3 $K_m$) such that $IC_{50} \cong K_i$. The final assay volume was made up to 100 $\mu$l with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 $\mu$l yttrium silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor $IC_{50}$ values obtained using the 'Fit Curve' Microsoft Excel extension. Results from these tests show that the compounds of the present invention are potent and selective inhibitors of cGMP-specific PDE5.

Preferred compounds of the present invention, such as those of Examples 1, 20, 22, 24, 32, 34, 44a, 44b, 44c, 63, 64, 65, 66, 67, and 85 and the compounds of Examples 5, 16, 17, 21, 26, 29, 47, 48, 49, 50, 50a, 51, 51a, 59, 68, 70, 71, 73, 74, 75, 77, 79, 80, 84, 86, 87, 89, 91, 92, 113, 114, 116, 118–128, 130–136, 138, 140, 143 have $IC_{50}$ values of less than about 10 nM for the PDE5 enzyme. A further preferred group of compounds having $IC_{50}$ values of less than about 10 nM for the PDE5 enzyme, are those of Examples 48, 50, 51, 51a, 59, 113, 114, 116, 118, 119, 121, 122–129, 131–136, 138, 140, 143. An additional group of compounds, such as those of Examples 48, 50, 51, 51a, 59, 63, 65, 70, 71, 72, 73, 76, 77, 78, 79, 80, 81, 82, 83, 89, 91, 92, 94, 113, 114, 116, 122–127, 129, 131, 132, 133, 134, 138, 140 have $IC_{50}$ values of less than about 5 nM for the PDE5 enzyme.

Especially preferred herein are compounds which have an $IC_{50}$ value of less than about 10, more preferably less than about 5 nM for the PDE5 enzyme in combination with greater than 10-fold selectivity for the PDE5 enzyme versus the PDE6 enzyme.

Functional Activity

This was assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996, 118 (suppl.), abstract 153P).

In Vivo Activity

Compounds were screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

Safety Profile

Compounds of the invention may be tested at varying i.v and p.o. doses in animals such as mouse and dog, observing for any untoward effects.

EXAMPLES AND PREPARATIONS

The synthesis of the compounds of the invention and of the intermediates for use therein are illustrated by the following Examples and Preparations.

$^1$H nuclear magnetic resonance (NMR) spectra were recorded using either a Varian Unity 300 or a Varian Inova 400 spectrometer and were in all cases consistent with the proposed structures. Characteristic chemical shifts ($\delta$) are given in parts-per-million downfield from tetramethylsilane using conventional abbreviations for designation of major peaks: e.g. s, singlet; d, doublet; t, triplet; q, quartet; m, multiplet; br, broad.

Mass spectra (m/z) were recorded using a Fisons Instruments Trio mass spectrometer in the thermospray ionisation mode (TSP) or using a Finnigan navigator in electrospray ionisation mode (ES)-positive and/or negative ionisation mode.

As used herein, the term "column chromatography" refers to normal phase chromatography using silica gel (0.04–0.06 mm).

Room temperature includes 20 to 25° C.

SYNTHESIS OF INTERMEDIATES

Preparation 1

2-Isobutoxynicotinic Acid

Sodium metal (3 g, 0.127 mol) was added in small amounts to isobutanol (100 mL)—some warming (80° C.) was needed to facilitate dissolution. 2-Chloronicotinic acid (10 g, 0.064 mol) was added and the solution refluxed for 1 h. A thick mixture resulted and a further 100 mL isobutanol was added and the mixture refluxed for 3 h. The mixture was cooled and quenched with 2N hydrochloric acid. The product was extracted into ethyl acetate and the organics washed with dilute hydrochloric acid (pH 3), dried (MgSO$_4$) and concentrated to give a brown solid. Purification by flash column chromatography (ethyl acetate as eluant) gave 10.5 g of product as a yellow solid.

$^1$H NMR (300 MHz, CDCl$_3$): $\delta$=1.05 (d, 6H), 2.20 (m, 1H), 4.40 (d, 2H), 7.10 (dd, 1H), 8.30 (dd, 1H), 8.45 (dd, 1H). LRMS (TSP) 196.2 (MH$^+$).

Preparation 2

2-n-Butoxynicotinic Acid

The title compound was prepared by the method of Preparation 1.

$^1$H NMR (400 MHz, d$_6$-DMSO): $\delta$=0.90 (t, 3H), 1.40 (m, 2H), 1.65 (m, 2H), 4.30 (t, 2H), 7.00 (dd, 1H), 8.05 (d, 1H), 8.30 (d, 1H).

Preparation 3

2-Isobutoxy-5-iodonicotinic Acid

N-Iodosuccinamide (18.22 g, 0.08 mol), trifluoroacetic acid (100 mL) and trifluoroacetic anhydride (25 mL) were added to 2-isobutoxynicotinic acid (10.55 g, 0.054 mol). The mixture was refluxed for 2.5 h, cooled and the solvents evaporated. The residue was extracted from water with ethyl acetate and the organics washed with water (twice) and brine (twice), dried (MgSO$_4$) and concentrated. The red residue was redissolved in ethyl acetate washed with sodium thiosulfate solution (twice), water (twice), brine (twice), redried (MgSO$_4$) and concentrated to give the desired product as a yellow solid.

$^1$H NMR (300 MHz, CDCl$_3$): $\delta$=1.05 (d, 6H), 2.20 (m, 1H), 4.40 (d, 2H), 8.50 (s, 1H), 8.70 (s, 1H), LRMS (TSP): 322.3 (MH$^+$).

Preparation 4

2-n-Butoxy-5-iodonicotinic Acid

The title compound was prepared by the method of Preparation 3.

$^1$H NMR (300 MHz, CDCl$_3$): $\delta$=1.00 (t, 3H), 1.50 (m, 2H), 1.85 (m, 2H), 4.60 (t, 2H), 8.50 (s, 1H), 8.70 (s, 1H), 10.50 (br s, 1H). LRMS (TSP): 322.0 (MH$^+$).

Preparation 5

Ethyl 2-Methyl-3-n-propyl-pyrazole-5-carboxylate

A solution of diethyl oxalate (27.2 mL, 0.2 mol) in 2-pentanone (21.2 mL, 0.2 mol) was added dropwise to a solution of sodium (4.83 g, 0.21 mol) in ethanol (200 mL), and the reaction stirred at 60° C. for 5 h, then cooled in an ice-bath. The solution was neutralised using acetic acid (11.5 mL, 0.2 mol) and N-methyl hydrazine (10.6 mL, 0.2 mol) then added dropwise. The mixture was stirred for a further 4 h at room temperature and concentrated under reduced pressure. The residue was partitioned between dichloromethane (300 mL) and water (200 mL), and the phases separated. The aqueous layer was extracted with dichloromethane (3×100 mL), the combined organic solutions were dried (MgSO$_4$) and evaporated under reduced pressure. The crude product was purified by column chromatography on silica gel, using ethyl acetate:hexane (25:75) as eluant to give ethyl 1-methyl-3-n-propyl-pyrazole-5-carboxylate (6.1 g) and the title compound (22.1 g, 56%).

$^1$H NMR (300 MHz, CDCl$_3$): $\delta$=1.00 (t, 3H), 1.40 (t, 3H), 1.70 (m, 2H), 2.60 (t, 2H), 3.87 (s, 3H), 4.40 (q, 2H), 6.60 (s, 1H).

Preparation 6

2-Methyl-3-n-propyl-pyrazole-5-carboxyylic Acid

A mixture of the title compound of Preparation 5 (21.5 g, 0.11 mol) in aqueous sodium hydroxide solution (50 mL, 6 N, 0.3 mol) was heated under reflux for 3 h. The cooled mixture was diluted with water (50 mL) and acidified using concentrated hydrochloric acid (25 mL) and the resulting precipitate was filtered and dried to give the title compound (17.3 g, 94%) as a pale yellow solid. A portion (1 g) of this solid, was recrystallised from water/ethanol.

m.p. 120–122° C.; $^1$H NMR (300 MHz, d$_6$-DMSO): δ=0.95 (t, 3H), 1.59 (m, 2H), 2.60 (t, 2H), 3.78 (s, 3H), 6.48 (s, 1H), 12.45 (s, 1H).

Preparation 7

2-Methyl-4-nitro-3-n-propyl-pyrazole-5-carboxylic Acid

Fuming sulfuric acid (17.5 mL) was added dropwise to ice-cooled fuming nitric acid (14.8 mL) whilst maintaining the internal temperature <30° C. The mixture was then warmed to 40° C. and the solid pyrazole carboxylic acid of Preparation 6 (16.33 g, 97 mmol) added slowly maintaining the temperature <60° C. The mixture was stirred at 60° C. for 14 h, cooled then poured into ice and stirred vigorously. The aqueous was extracted with dichloromethane (2×100 mL), dried (MgSO$_4$) and concentrated to give a solid. The yield of the title compound was 19.0 g. The solid was recrystallised from methanol/water.

$^1$H NMR (300 MHz, d$_6$-DMSO): δ=0.95 (t, 3H), 1.60 (m, 2H), 2.96 (t, 2H), 3.88 (s, 3H), 13.75 (s, 1H).

Preparation 8

2-Methyl-4-nitro-3-n-propyl-pyrazole-5-carboxamide

A mixture of the title compound of Preparation 7 (18.6 g, 87.3 mmol) in thionyl chloride (75 mL), was heated under reflux for 2 h. The cooled reaction mixture was concentrated under reduced pressure and the residue poured into an ice/ammonium hydroxide mixture. This was extracted with dichloromethane (4×100 mL) and the combined organic extracts dried (MgSO$_4$) and evaporated under reduced pressure. The crude product was purified by column chromatography on silica gel, using dichloromethane:methanol:0.88 ammonia (95:5:1) as eluant to afford the title compound (6.8 g, 37%) as a solid.

$^1$H NMR (300 MHz, CDCl$_3$): δ=1.07 (t, 3H), 1.72 (m, 2H), 3.00 (t, 2H), 3.97 (s, 3H), 6.14 (s, 1H), 7.40 (s, 1H).

Preparation 9

4-Amino-2-methyl-3-n-pyropyl-pyrazole-5-carboxamide

A mixture of the title compound of Preparation 8 (6.17 g, 29.0 mmol) and tin(II) chloride dihydrate (32.8 g, 145 mmol) in industrial methylated spirits (IMS) (100 mL) was heated under reflux for 2 h. The cooled mixture was concentrated under reduced pressure to approximately half its volume, basified to pH 9 using aqueous 2 N sodium hydroxide solution, and extracted with dichloromethane (3×300 mL). The combined organic extracts were dried (MgSO$_4$) and evaporated under reduced pressure and the crude product recrystallised from ethyl acetate/methanol to afford the title compound (4.86 g, 92%).

m.p.170–174° C.; $^1$H NMR (300 MHz, d$_6$-DMSO): δ=0.90 (t, 3H), 1.47 (m, 2H), 2.50 (t, 2H), 3.68 (s, 3H), 4.43 (s, 2H), 6.92 (s, 1H), 7.04 (s, 1H).

Preparation 10a

3-Ethyl-1-(2-methoxyethyl)-4-nitro-pyrazole-5-carboxamide and

Preparation 10b

3-Ethyl-2-(2-methoxyethyl)-4-nitro-pyrazole-5-carboxamide

A mixture of 3-ethyl-4-nitro-1H-pyrazole-5-carboxamide (prepared as in WO 98/49166) (1.7 g, 8.8 mmol), 2-bromoethyl methyl ether (0.85 mL, 8.85 mmol) and cesium carbonate (2.9 g, 9.0 mmol) in dimethylformamide (20 mL) was stirred at room temperature for 20 h. The reaction mixture was concentrated under reduced pressure and the residue was partitioned between ethyl acetate (125 mL) and brine (100 mL). The phases were separated, and the organic layer was dried (Na$_2$SO$_4$), and evaporated under reduced pressure. The crude product was purified by column chromatography on silica gel, using ethyl acetate:methanol (97:3) as eluant to afford 3-ethyl-1-(2-methoxyethyl)-4-nitro-pyrazole-5-carboxamide (831 mg, 39%).

$^1$H NMR (300 MHz, d$_6$-DMSO): 1.20 (t, 3H), 2.80 (q, 2H), 3.20 (s, 3H), 3.65 (t, 2H), 4.20 (t, 2H), 8.10 (br s, 1H), 8.40 (br s, 1H). LRMS (TSP) 243.6 (MH$^+$). and 3-ethyl-2-(2-methoxyethyl)-4-nitro-pyrazole-5-carboxamide (793 mg, 37%). $^1$H NMR (300 MHz, CDCl$_3$): δ=1.18 (t, 3H), 2.98 (q, 2H), 3.22 (s, 3H), 3.70 (t, 2H), 4.28 (t, 2H), 7.65 (s, 1H), 7.94 (s, 1H). LRMS: m/z 243 (MH)$^+$.

Preparation 11

4-Amino-3-ethyl-2-(2-methoxyethyl)-pyrazole-5-carboxamide

10% Palladium on carbon (100 mg) was added to a stirred slurry of 3-ethyl-2-(2-methoxyethyl)-4-nitro-pyrazole-5-carboxamide (5 g, 20.77 mmol) in ethanol (100 mL) and the mixture stirred in a pressure vessel under a hydrogen atmosphere (344.7 kPa (50 psi)) at room temperature for 6 h. The mixture was filtered and concentrated. Recrystallisation from hot ethyl acetate gave the product as white crystals (3.5 g). The mother liquor was concentrated to give a further 1.5 g of product as a grey powder.

$^1$H NMR (300 MHz, d$_6$-DMSO): δ=1.00 (t, 3H), 2.50 (q, 2H), 3.20 (s, 3H), 3.60 (t, 2H), 4.05 (t, 2H), 4.40 (s, 2H), 6.90 (br s, 1H), 7.00 (br s, 1H). LRMS 425.0 (2M)H$^+$.

Preparation 12

4-Amino-3-ethyl-1-(2-methoxyethyl)-pyrazole-5-carboxamide

Obtained from the title compound of Preparation 10a (95%), using a similar procedure to that described in Preparation 11, and was purified by column chromatography using dichloromethane:methanol (95:5) as eluant.

$^1$H NMR (300 MHz, CDCl$_3$): δ=1.26 (t, 3H), 2.58 (q, 2H), 3.37 (s, 3H), 3.60 (s, 2H), 3.82 (t, 2H), 4.50 (t, 2H). LRMS 213 MH$^+$.

Preparation 13

N-[3-(Aminocarbonyl)-5-ethyl-1-(2-methoxyethyl)-1H-pyrazol-4-yl]-2-butoxy-5-iodonicotinamide Oxalyl chloride (2 g, 15.9 mmol) was added to a stirred solution of the title compound from Preparation 4 (1.28 g, 3.98 mmol) in dichloromethane (20 mL) and 3 drops N,N-dimethylformamide added. After 2.5 h the solvent was evaporated and the residue azeotroped 3 times with dichloromethane. The residue was resuspended in dichloromethane (4 mL) and added to a stirred mixture of the title compound of Preparation 11 (0.76 g, 3.58 mmol) and triethylamine (0.8 g, 7.97 mmol) in dichloromethane (10 mL). After 1 h the solvent was evaporated and the residue partitioned between ethyl acetate and water. The organic phase was separated and washed with 2N HCl (twice), sodium bicarbonate solution (twice) and brine before being dried (MgSO$_4$) and concentrated. The product was triturated with ether and filtered to give 820 mg of pure product as a white solid. The mother liquor was concentrated and purified by flash column chromatography (elution with 80% ethyl acetate: hexane), to give a further 605 mg of product.

$^1$H NMR (400 MHz, CDCl$_3$): δ=0.95 (t, 3H), 1.20 (t, 3H), 1.45 (m, 2H), 1.90 (m, 2H), 2.85 (q, 2H), 3.35 (s, 3H), 3.80 (t, 2H), 4.25 (t, 2H), 4.60 (t, 2H), 5.20 (br s, 1H), 6.60 (br s, 1H), 8.40 (s, 1H), 8.80 (s, 1H), 10.30 (s, 1H). LRMS (TSP): 516.2 (MH$^+$).

Preparation 14

N-[3-(Aminocarbonyl)-1-methyl-5-propyl-1H-pyrazol-4-yl]-5-iodo-2-isobutoxynicotinamide The title compound was prepared using the method of Preparation 13.

$^1$H NMR (300 MHz, CDCl$_3$): δ=0.90 (t, 3H), 1.00 (d, 6H), 1.60 (m, 2H), 2.30 (m, 1H), 2.80 (t, 2H), 3.80 (s, 3H), 4.30 (d, 2H), 5.20 (br s, 1H), 6.60 (br s, 1H), 8.40 (s, 1H), 8.80 (s, 1H), 10.20 (s, 1H). LRMS (TSP): 486.1 (MH$^+$).

Preparation 15

N-[5-(Aminocarbonyl)-3-ethyl-1-(2-methoxyethyl)-1H-pyrazol-4-yl]-2-butoxy-5-iodonicotinamide 1-(3-Dimethylaminopropyl)-3-ethyl-carbodiimide hydrochloride (434 mg, 2.26 mmol) was added to a stirred solution of 5-iodo-2-butoxynicotinic acid (615 mg, 1.92 mmol), 4-amino-3-ethyl-1-(2-methoxyethyl)-pyrazole-5-carboxamide (370 mg, 1.74 mmol), 1-hydroxybenzotriazole hydrate (346 mg, 2.26 mmol) and diisopropylethylamine (0.9 mL, 5.22 mmol) in tetrahydrofuran (12 mL) at room temperature under a nitrogen atmosphere. After 20 h the solvent was evaporated and the product was extracted from 10% sodium bicarbonate solution with dichloromethane (3×100 mL). The organics were dried (MgSO$_4$) and concentrated to give a fawn solid. The solid was triturated with di-isopropylether to give an off-white solid (1.2 g).

$^1$H NMR (300 MHz, CDCl$_3$): δ=1.00 (t, 3H), 1.20 (t, 3H), 1.45 (m, 2H), 1.85 (m, 2H), 2.60 (q, 2H), 3.40 (s, 3H), 3.80 (t, 2H), 4.45 (t, 2H), 4.50 (q, 2H), 5.60 (br s, 1H), 7.80 (br s, 1H), 8.50 (s, 1H), 8.80 (s, 1H), 9.60 (s, 1H). LRMS (TSP): 515.7 (MH$^+$).

Preparation 16

N-[3-(Aminocarbonyl)-5-ethyl-1H-pyrazol-4-yl]-2-butoxy-5-iodonicotinamide

The title compound was made by the method of Preparation 13 using, as starting material, 4-amino-3-ethyl-1H-pyrazole-5-carboxamide (prepared as in WO 98/49166).

$^1$H NMR (400 MHz, d$_6$-DMSO): δ=0.95 (t, 3H), 1.05 (t, 3H), 1.30 (m, 2H), 1.75 (m, 2H), 2.70 (q, 2H), 4.40 (t, 2H), 5.80 (br s, 1H), 6.60 (br s, 1H), 8.20 (s, 1H), 8.55 (s, 1H), 10.30 (s, 1H). LRMS (TSP): 457.9 (MH$^+$).

Preparation 17

N-{3-(Aminocarbonyl)-1-[2-dimethylamino)ethyl]-5-ethyl]-1H-pyrazol-4-yl}-2-butoxy-5-iodonicotinamide Cesium carbonate (1.17 g, 3.59 mmol) was added to a stirred solution of the title compound from Preparation 16 (800 mg, 1.79 mmol) and N,N-dimethylaminoethyl chloride hydrochloride (309 mg, 2.15 mmol) in N,N-dimethylformamide (10 mL) under a nitrogen atmosphere. The mixture was heated at 80° C. for 24 h. The mixture was cooled and extracted from water with ethyl acetate. The organics were dried (MgSO$_4$) and concentrated to give a brown oil. Purification by flash column chromatography (gradient elution from 100% dichloromethane to 90% dichloromethane/MeOH) gave the product as a pale brown oil (522 mg).

$^1$H NMR (400 MHz, CDCl$_3$): δ=0.95 (t, 3H), 1.20 (t, 3H), 1.40 (m, 2H), 1.90 (m, 2H), 2.35 (s, 6H), 2.80 (t, 2H), 2.85 (q, 2H), 4.20 (t, 2H), 4.60 (t, 2H), 5.30 (br s, 1H), 6.60 (br s, 1H), 8.40 (s, 1H) 8.75 (s, 1H), 10.35 (s, 1H). LRMS (TSP): 529.5 (MH$^+$).

Preparations 17a to 17c

The following compounds were made by the method of Preparation 17

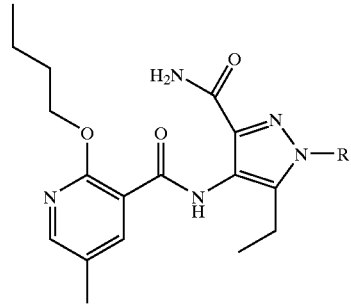

from the compounds of Preparation 16 and the appropriate alkylating agent.

| Preparation | R | LRMS (MH$^+$) | $^1$H NMR |
|---|---|---|---|
| 17a[1] | ![structure] | 571 | (400 MHz, CDCl$_3$): δ = 0.95(t, 3H), 1.20(t, 3H), 1.45(m, 2H), 1.90(m, 2H), 2.50(m, 4H), 2.85(t, 2H), 2.90 (q, 2H), 3.70(m, 4H), 4.40(t, 2H), 4.60(t, 2H), 5.25(br s, 1H), 6.60(br s, 1H), 8.45(s, 1H), 8.75(s, 1H), 10.40(s, 1H). |

-continued

| Preparation | R | LRMS (MH+) | 1H NMR |
|---|---|---|---|
| 17b[2] | (piperidine with Boc group structure) | 641 | (400 MHz, CDCl$_3$): δ = 1.00(t, 3H), 1.20(t, 3H), 1.40(m, 2H), 1.45(s, 9H), 1.90(m, 4H), 2.15(m, 2H), 2.80 (m, 4H), 4.25(m, 3H), 4.55(t, 2H), 5.30(s, 1H), 6.60(s, 1H), 8.40(s, 1H), 8.75(s, 1H), 10.40(s, 1H). |
| 17c[3] | (azetidine with Boc group structure) | 613.0 | (400 MHz, CDCl$_3$): δ = 0.90(t, 3H), 1.10(t, 3H), 1.40(m, 2H), 1.45(s, 9H), 1.85(m, 2H), 2.80(q, 2H), 4.30 (t, 2H), 4.40(m, 2H), 4.50(t, 2H), 5.00(m, 1H), 5.60(br s, 1H), 6.70(br s, 1H), 8.40(s, 1H), 8.65(s, 1H), 10.30(s, 1H). |

[1]= N-(2-chloroethyl)morpholine hydrochloride was used as alkylating agent
[2]= tert-butyl 4-[(methylsulfonyl)oxy]-1-piperidinecarboxylate (WO 93/19059) was used as alkylating agent
[3]= tert-butyl-3-iodo-1-azetidinecarboxylate (Preparation 44) was used as alkylating agent

Preparation 18

Pyridine-2-ethoxy-3-carboxylic Acid

A solution of potassium t-butoxide (44.9 g, 0.40 mol) in absolute ethanol (300 mL) was added slowly to a solution of 2-chloronicotinic acid (30 g, 0.19 mol) in ethanol (100 mL), and the reaction heated in a sealed vessel at 170° C. for 20 h. On cooling, the reaction mixture was concentrated under reduced pressure, the residue dissolved in water (200 mL) and acidified to pH 3 with aqueous hydrochloric acid. The aqueous solution was extracted with dichloromethane (4×200 mL), the organic phases combined, dried (Na$_2$SO$_4$) and concentrated under reduced pressure to afford the title compound (27.4 g, 41%) as a white solid.

$^1$H NMR (300 MHz, CDCl$_3$): δ=1.53 (t, 3H), 4.69 (q, 2H), 7.13 (m, 1H), 8.37 (d, 1H), 8.48 (d, 1H).

Preparation 19

Pyridine-2-ethoxy-3-carboxylic Acid Ethyl Ester

A suspension of the title compound of Preparation 18 (16.4 g, 98 mmol), and cesium carbonate (32 g, 98 mmol) in N,N-dimethylformamide (240 mL) was stirred at room temperature for 2 h. Ethyl iodide (7.85 mL, 98 mmol) was added and the reaction stirred for a further 24 h. The reaction mixture was concentrated under reduced pressure and the residue partitioned between aqueous sodium carbonate solution (100 mL) and ethyl acetate (100 mL). The phases were separated and the aqueous phase extracted with ethyl acetate (2×100 mL). The combined organic solutions were washed with brine, dried (Na$_2$SO$_4$) and evaporated under reduced pressure to afford the title compound (18.0 g, 94%) as a pale yellow oil.

$^1$H NMR (300 MHz, CDCl$_3$): δ=1.41 (m, 6H), 4.36 (q, 2H), 4.48 (q, 2H), 6.90 (m, 1H), 8.12 (d, 1H), 8.28 (d, 1H).

Preparation 20

Pyridine-2-ethoxy-5-nitro-3-carboxylic Acid Ethyl Ester

Ammonium nitrate (5.36 g, 66 mmol) was added portionwise to an ice-cooled solution of the title compound of Preparation 19 (4.66 g, 22.3 mmol) in trifluoroacetic anhydride (50 mL) and the reaction stirred for 18 h at room temperature. The reaction mixture was carefully poured into ice water (200 mL) and the resulting suspension stirred for an hour. The precipitate was filtered off, washed with water and dried under suction to afford the title compound (3.29 g, 61%).

$^1$H NMR (300 MHz, CDCl$_3$): δ=1.41 (t, 3H), 1.48 (t, 3H), 4.41 (q, 2H), 4.62 (q, 2H), 8.89 (s, 1H), 9.16 (s, 1H).

Preparation 21

Pyridine-2-ethoxy-5-nitro-3-carboxylic Acid

Aqueous sodium hydroxide solution (4 mL, 5N, 20 mmol) was added dropwise to a solution of the title compound of Preparation 20 (5.1 g, 20 mmol) in ethanol (100 mL) and the reaction stirred at room temperature for 18 h. The reaction mixture was concentrated under reduced pressure, the residue suspended in water (50 mL) and acidified to pH 3 with hydrochloric acid. This aqueous solution was extracted with ethyl acetate (3×100 mL), the combined organic layers washed with brine (100 mL), dried (Na$_2$SO$_4$) and evaporated under reduced pressure to give a beige solid. The crude product was recrystallised from ethyl acetate/hexane to afford the title compound (3.32 g, 78%) as beige crystals.

$^1$H NMR (300 MHz, CDCl$_3$): δ=1.55 (t, 3H), 4.78 (q, 2H), 9.17 (s, 1H), 9.23 (s, 1H).

Preparation 22

5-Nitro-N-[3-(aminocarbonyl)-1-methyl-5-propyl-1H-pyrazol-4-yl]-2-ethoxynicotinamide The title compound was made by the method of Preparation 15.

$^1$H NMR (300 MHz, CDCl$_3$): δ=0.95 (t, 3H), 1.60 (t, 3H), 1.70 (m, 2H), 2.90 (t, 2H), 3.85 (s, 3H), 4.80 (q, 2H), 5.35 (br s, 1H), 6.60 (br s, 1H), 9.15 (s, 1H), 9.30 (s, 1H), 10.50 (s, 1H). TLC (95% dichloromethane/5% MeOH)-R$_f$=0.5.

Preparation 23

5-Amino-N-[3-(aminocarbonyl)-1-methyl-5-propyl-1H-pyrazol-4-yl]-2-ethoxynicotinamide Raney® nickel (10 g of a 50% aqueous slurry) was added to the title compound of Preparation 22 (20 g, 53.2 mmol)

in ethanol (900 mL). The mixture was hydrogenated (344.7 kPa (50 psi) hydrogen) at 60° C. for 16 h, cooled and filtered through a plug of Arbocel® to give the product (no further purification).

$^1$H NMR (300 MHz, CDCl$_3$): δ=0.90 (t, 3H), 1.50 (t, 3H), 1.65 (m, 2H), 2.80 (t, 2H), 3.50 (br s, 2H), 3.80 (s, 3H), 4.60 (q, 2H), 5.20 (br s, 1H), 6.60 (br s, 1H), 7.80 (s, 1H), 7.95 (s, 1H), 10.50 (s, 1H). TLC (90% dichloromethane/10% MeOH)-R$_f$=0.3.

Preparation 24

2-Ethoxy-5-nitropyridine-3-carboxamide

N,N-Dimethylformamide (2 drops) was added to an ice-cold solution of the title compound of Preparation 21 (3.0 g, 13.9 mmol) and oxalyl chloride (5 mL, 57.0 mmol) in dichloromethane (30 mL), and the reaction then stirred at room temperature for 2 h. The reaction mixture was concentrated under reduced pressure and azeotroped with dichloromethane. The residue was dissolved in dichloromethane (30 mL), the solution cooled in an ice-bath, 0.88 ammonia (5 mL) added, and the reaction stirred for 15 minutes. The mixture was partitioned between dichloromethane and water and the layers separated. The organic phase was washed with aqueous saturated sodium bicarbonate solution, brine, then dried (MgSO$_4$) and evaporated under reduced pressure. The residual yellow solid was triturated with diethyl ether, filtered and dried to afford the title compound (2.4 g, 83%).

$^1$H NMR (300 MHz, CDCl$_3$): δ=1.56 (t, 3H), 4.74 (q, 2H), 6.14 (br s, 1H), 7.66 (br s, 1H), 9.18 (d, 1H), 9.29 (d, 1H). LRMS 229 (MNH$_4$)$^+$.

Preparation 25

2-Ethoxy-5-nitropyridine-3-carbonitrile

Trifluoroacetic anhydride (3.46 g, 16.5 mmol) in dioxan (5 mL) was added to an ice-cold solution of the title compound of Preparation 24 (2.32 g, 11.0 mmol) and pyridine (2.17 g, 27.5 mmol) in dioxan (15 mL), and the solution stirred at room temperature for 3 h. The mixture was concentrated under reduced pressure and the residue partitioned between ethyl acetate and water. The layers were separated and the organic phase washed consecutively with hydrochloric acid (2N, 2x), aqueous saturated sodium bicarbonate solution, then brine. The solution was dried (MgSO$_4$) and evaporated under reduced pressure. The residue was purified by column chromatography on silica gel using an elution gradient of pentane:ethyl acetate (100:0 to 95:5) to afford the title compound (1.73 g, 81%).

$^1$H NMR (300 MHz, CDCl$_3$): δ=1.50 (t, 3H), 4.63 (q, 2H), 8.66 (d, 1H), 9.20 (d, 1H).

Preparation 26

2-Ethoxy-5-nitropyridine-3-carboximidamide Acetate

The title compound of Preparation 25 (11.0 g, 57.0 mmol) was added "in one portion" to a cooled (−10° C.) solution of ethanol saturated with HCl gas, (100 mL), and the reaction stirred at this temperature for 8 h. The reaction was evaporated under reduced pressure, the residue triturated with diethyl ether, and the precipitate filtered off. The solid was partitioned between ethyl acetate and aqueous saturated sodium bicarbonate solution, and the layers separated. The organic phase was washed with aqueous saturated sodium bicarbonate solution, brine, then dried (MgSO$_4$), and evaporated under reduced pressure to give a white solid, 4.25 g. Ammonium acetate (3.61 g, 46.9 mmol) was added to a solution of this intermediate imidate (8.62 g) in ethanol (80 mL), and the reaction heated under reflux for an hour. Tlc analysis showed starting material remaining, so additional ammonium acetate (0.5 g, 6.5 mmol) was added, and the reaction heated under reflux for a further 30 min. The cooled reaction mixture was evaporated under reduced pressure and the residue triturated with diethyl ether. The resulting solid was filtered off, and dried under vacuum to afford the title compound (8.26 g).

$^1$H NMR (300 MHz, d$_6$-DMSO): δ=1.38 (t, 3H), 1.77 (s, 3H), 4.54 (q, 2H), 8.74 (d, 1H), 9.20 (d, 1H). LRMS 211 (MH)$^+$.

Preparation 27

4-Nitro-1H-pyrazole-5-carboxamide

Oxalyl chloride (33.3 mL, 0.4 mol) was added dropwise over 15 minutes to an ice-cold suspension of 4-nitro-1H-pyrazole-5-carboxylic acid (40.0 g, 0.25 mol) and N,N-dimethylformamide (3 drops) in dichloromethane (400 mL). The mixture was allowed to warm to room temperature and stirred for 24 h. Additional oxalyl chloride (16.7 mL, 0.2 mol) was added and the reaction stirred for a further 24 h. The reaction mixture was filtered, the filtrate evaporated under reduced pressure and redissolved in tetrahydrofuran (400 mL). This solution was cooled in an ice-bath, ammonia bubbled through for an hour, and the mixture purged with nitrogen for 30 minutes. The reaction mixture was concentrated under reduced pressure, the residue triturated with water, and the solid filtered and dried under vacuum to afford the title compound (34.7 g, 86%) as a white solid.

$^1$H NMR (300 MHz, d$_6$-DMSO): δ=7.60–8.10 (m, 3H), 8.68 (s, 1H).

Preparation 28

2-Methyl-4-nitro-pyrazole-5-carboxamide

A mixture of the title compound of Preparation 27 (35.5 g, 0.22 mol), cesium carbonate (79.7 g, 0.24 mol), and methyl iodide (34.7 g, 0.24 mol) in N,N-dimethylformamide (200 mL) was stirred at room temperature for 4 days. The reaction mixture was concentrated under reduced pressure and the residue azeotroped with xylene. The resulting brown gum was triturated with hot ethyl acetate (6×400 mL) and hot methanol/dichloromethane (4×500 mL), the resulting suspensions filtered and the combined filtrates evaporated under reduced pressure. The residual brown solid was purified by column chromatography on silica gel, using an elution gradient of ethyl acetate:hexane (30:70 to 100:0) to afford the title compound, (11.5 g, 31%) as a solid.

$^1$H NMR (300 MHz, CDCl$_3$): δ=4.03 (s, 3H), 5.88 (s, 1H), 7.80 (s, 1H), 8.25 (s, 1H).

Preparation 29

4-Amino-2-methyl-pyrazole-5-carboxamide

A mixture of the title compound of Preparation 28 (5.0 g, 30.0 mmol) and 10% palladium on charcoal (500 mg) in methanol (200 mL) was hydrogenated at 206.8 kPa (30 psi) and 50° C. for 18 h. The cooled mixture was filtered through Arbocel®, the filter pad washed with methanol, and the combined filtrate evaporated under reduced pressure to afford the title compound, (4.2 g, 100%) as a pink solid.

¹H NMR (300 MHz, d₆-DMSO): δ=3.72 (s, 3H), 4.60 (s, 2H), 6.88 (s, 1H), 7.05 (m, 2H).

Preparation 30

6-(Dimethylamino)pyridin-3-yl Boronic Acid Dihydrochloride n-Butyllithium (5.3 mL, 1.6M in hexanes, 8.5 mmol) was added dropwise to a cooled (−70° C.) solution of 5-bromo-2-(dimethylamino)pyridine (J. Org. Chem. 1983; 48; 1064) (1.5 g, 7.46 mmol) in tetrahydrofuran (20 mL), and the solution stirred for 30 minutes. A solution of triisopropyl borate (2.57 mL, 11.2 mmol) in tetrahydrofuran (4 mL) was added dropwise, and the reaction then allowed to warm to room temperature over 3 h. The reaction was quenched by the addition of hydrochloric acid (2N), and the mixture then evaporated under reduced pressure. The residue was crystallised from methanol:diethyl ether to afford the title compound, (800 mg, 45%) as an off-white solid.

¹H NMR (300 MHz, d₆-DMSO): δ=3.20 (s, 6H), 7.18 (d, 1H), 8.18 (m, 2H).

Preparation 31

2-Propoxy-5-iodonicotinic Acid

The title compound was prepared from the title compound of Preparation 40 using the method of Preparation 3.

¹H NMR (300 MHz, CDCl₃): δ=1.05 (t, 3H), 1.85–2.0 (m, 2H), 4.5 (t, 2H), 8.5 (s, 1H), 8.6 (s, 1H). Analysis: found C, 35.16; H, 3.19; N, 4.46. Calcd for $C_9H_{10}INO_3$: C, 35.19; H, 3.28; N, 4.56%.

Preparation 32

[N-3-(Aminocarbonyl)-5-ethyl-1H-pyrazol-4-yl]-5-iodo-2-propoxynicotinamide

The title compound was prepared from 2-propoxy-5-iodonicotinic acid (see Preparation 31 above) and 4-amino-3-ethyl-1H-pyrazole-5-carboxamide (prepared as described in WO 98/49166) according to the method described in Preparation 13.

¹H NMR (300 MHz, d₄-MeOH): δ=1.0 (t, 3H), 1.25 (t, 3H), 1.85–2.0 (m, 2H), 2.8 (q, 2H), 4.5 (t, 2H), 8.5 (s, 1H), 8.6 (s, 1H). LRMS (TSP) 444 (MH⁺).

Preparation 33

N[5-(Aminocarbonyl)-1-methyl-3-propyl-1H-pyrazol-4-yl]-5-iodo-2-proroxynicotinamide The title compound was prepared from 2-propoxy-5-iodonicotinic acid (see Preparation 31 above) and 4-amino-1-methyl-3-propyl-1H-pyrazole-5-carboxamide (prepared as described in EP 526 004) according to the method described in Preparation 13.

m.p. 257–9° C.; ¹H NMR (300 MHz, CDCl₃): δ=0.95 (t, 3H), 1.15 (t, 3H), 1.6–1.75 (m, 2H), 1.85–1.95 (m, 2H), 2.55 (t, 2H), 4.05 (s, 3H), 4.5 (t, 2H), 5.45–5.65 (br s, 1H), 7.55–7.65 (br s, 1H), 8.5 (s, 1H), 8.8 (s, 1H), 9.3 (s, 1H). LRMS (ES-negative ion) 470 (M−H), (ES-positive ion) 472 (MH⁺). Analysis: found C, 43.32; H, 4.62; N, 14.77. Calcd for $C_{17}H_{22}IN_5O_3$: C, 43.32; H, 4.71; N, 14.86%.

Preparation 34

Methyl 5-{[(Benzyloxy)carbonyl]amino}-2-propoxynicotinate

Benzyl chloroformate (6.6 mL, 45.9 mmol) was added dropwise to the title compound of Preparation 43 (9.6 g, 45.9 mmol) and sodium carbonate (4.4 g, 41.4 mmol) in tetrahydrofuran (51 mL) and water (38 mL) with ice-cooling. After 5 h, the reaction mixture was diluted with ethyl acetate (200 mL), the aqueous phase removed, and the remaining organic phase washed with water (200 mL), dried over MgSO₄, concentrated, and the brown solid triturated with pentane to give the title compound as a buff solid (13.5 g, 39.3 mmol).

¹H NMR (300 MHz, CDCl₃): δ=1.0 (t, 3H), 1.9 (2H, tq), 3.85 (s, 3H), 4.35 (t, 2H), 5.2 (s, 2H), 6.5 (br s, 1H), 7.3–7.4 (m, 5H), 8.25 (2H, br s). LRMS (TSP) 345 (MH⁺).

Preparation 35

5-{[(Benzyloxy)carbonyl]amino}-2-propoxynicotinic Acid

A solution of sodium hydroxide (3.12 g, 78 mmol) in water (15 mL) was added to a stirred suspension of the title compound of Preparation 34 (13.55 g, 39 mmol) in methanol (140 mL) and the mixture stirred at room temperature for 18 h. After concentration in vacuo, the residue was dissolved in water (100 mL) which was acidified to pH 5 with conc. hydrochloric acid and the precipitate removed by filtration, washed with water and dried. Purification by column chromatography (ethyl acetate:pentane (4:1) as eluant) to gave the title compound as a white solid (8.9 g, 27 mmol).

¹H NMR (300 MHz, CDCl₃): δ=1.0 (t, 3H), 1.8–1.95 (m, 2H), 4.45 (t, 2H), 5.2 (s, 2H), 7.3–7.4 (m, 5H), 7.95 (br s, 1H), 8.4 (d, 1H), 8.5 (br s, 1H), 11.1 (br s, 1H). LRMS (TSP) 331 (MH⁺).

Preparation 36

Benzyl 5-({[5-(Aminocarbonyl)-1-methyl-3-propyl-1H-pyrazol-4-yl]-amino}carbonyl)-6-propoxy-3-pyridinylcarbamate A solution of the title compound from Preparation 35 (1.51 g, 4.6 mmol), O-(7-azabenzotriazol-1-yl)-N,N,N',N'-tetramethyluronium hexafluorophosphate (1.74 g, 4.6 mmol) and N,N-diisopropylethylamine (2.39 mL, 13.7 mmol) in N,N-dimethylformamide (20 mL) was added to 4-amino-1-methyl-3-propyl-1H-pyrazole-5-carboxamide (prepared as described in EP 526 004; 1.0 g, 4.6 mmol) and N,N-diisopropylethylamine (2.39 mL, 13.7 mmol) in N,N-dimethylformamide (10 mL) and the resultant mixture stirred at room temperature for 24 h. After concentrating in vacuo, the mixture was dissolved in ethyl acetate (50 mL), and washed with aq. sodium bicarbonate solution (5%, 50 mL). The nascent solid was removed by filtration and confirmed as product (659 mg, 1.3 mmol). The organic phase was washed with water (50 mL) and brine (25 mL) before drying over MgSO₄ and concentrating to a pink solid which was crystallised from hot ethyl acetate to afford further title compound as a white solid (368 mg, 0.7 mmol). The mother liquors were then purified by column chromatography (ethyl acetate:pentane 3:1 as eluant) to afford a further batch of title compound (111 mg, 0.2 mmol).

¹H NMR (300 MHz, d₆-DMSO): δ=0.85 (t, 3H), 0.95 (t, 3H), 1.5–1.6 (m, 2H), 1.7–1.85 (m, 2H), 2.4 (t, 2H), 3.9 (s, 3H), 4.3 (t, 2H), 5.15 (s, 2H), 7.3–7.45 (m, 5H), 7,7 (br s, 1H), 8.2 (br s, 1H), 8.4 (s, 1H), 9.5 (s, 1H), 9.85 (br s, 1H). LRMS (TSP) 495 (MH⁺). Analysis: found C, 60.19; H,. 6.02; N, 16.81. Calcd for $C_{25}H_{30}N_6O_5 \cdot 0.3H_2O$: C, 60.06; H, 6.17; N, 16.81%.

Preparation 37

2-Ethoxy-5-iodonicotinic Acid

The title compound was prepared from 2-ethoxynicotinic acid using the method of Preparation 3.

¹H NMR (400 MHz, d₆-DMSO): δ=13.2 (br s, 1H), 8.5 (d, 1H), 8.3 (d, 1H), 4.35 (q, 2H), 1.3 (t, 3H).

Preparation 38

N-[5-(Aminocarbonyl)-3-ethyl-1H-pyrazol-4-yl]-2-ethoxy-5-iodonicotinamide

The title compound of Preparation 37 (8 g, 27.3 mmol) in dichloromethane (200 mL) was treated with 1-hydroxybenzotriazole hydrate (4.43 g, 32.8 mmol), N,N-diisopropylethylamine (14.3 mL, 77.8 mmol), 1-(3-dimethylaminopropyl)-3-ethylcarbodiimide hydro-chloride (6.27 g, 31.7 mmol) and 4-amino-3-ethyl-1H-pyrazole-5-carboxamide (prepared as described in WO 98/49166; 3.78 g, 24 mmol), and the resultant mixture stirred at room temperature for 14 h. After washing with water (100 mL), a portion of the title compound was isolated by filtration of the precipitate as a pale brown solid (6.55 g, 15.3 mmol). The organic phase was dried over $MgSO_4$, concentrated and the residue treated with diethyl ether to give further title compound as a pale brown solid (1.65 g, 3.84 mmol).

$^1$H NMR (300 MHz, $CDCl_3$): δ=1.25 (t, 3H), 1.55 (t, 3H), 2.9 (2H, q), 2.65 (2H, q), 5.4 (br s, 1H), 6.75 (br s, 1H), 8.4 (d, 1H), 8.8 (d, 1H), 10.65 (br s 1H). LRMS (ES-positive ion) 430 ($MH^+$).

Preparation 39

N-{3-(Aminocarbonyl)-1-[2-(dimethylamino)ethyl]-5-ethyl-1H-pryazol-4-yl}-2-ethoxy-5-iodonicotinamide Cesium carbonate (3.3 g, 10.2 mmol) was added to a stirred solution of the title compound of Preparation 38 (4 g, 9.3 mmol) and 2-dimethylaminoethylchloride hydrochloride (1.2 g, 11.2 mmol) in N,N-dimethylformamide (50 mL) and the resultant solution stirred at 80° C. for 14 h. Concentration gave a residue which was taken up in ethyl acetate (150 mL) and water (250 mL). The separated aqueous phase was extracted with ethyl acetate (2×150 mL), and the combined organics dried over $MgSO_4$, concentrated and purified by column chromatography (dichloromethane:methanol:ammonia (98:2:0.2 to 97:2.5:0.5) as eluant) to afford the title compound as a white solid (2.23 g, 4.5 mol).

$^1$H NMR (400 MHz, $CDCl_3$): δ=1.3 (t, 3H), 1.55 (t, 3H), 2.3 (s, 6H), 2.8 (t, 2H), 2.9 (q, 2H), 4.2 (t, 2H), 4.6 (q, 2H), 5.25 (br s, 1H), 6.6 (br s, 1H), 8.4 (s, 1H), 8.8 (s, 1H), 10.5 (s, 1H); LRMS (TSP) 401 ($MH^+$).

The regioisomers were confirmed by long range $^1$H-$^{13}$C correlation experiments (HMBC).

Preparation 40

2-Propoxynicotinic Acid

The title compound was prepared in 73% yield from n-propanol using the method of Preparation 1.

$^1$H NMR (300 MHz, $d_6$-DMSO +1 drop $d_1$-trifluoroacetic acid) δ=0.95 (t, 3H), 1.65–1.8 (m, 2H), 4.25 (t, 2H), 7.0 (m, 1H), 8.1 (d, 1H), 8.25 (d, 1H).

Preparation 41

Methyl-2-propoxynicotinate

Diethyl azodicarboxylate (2.2 mL, 14 mmol) was added dropwise to a solution of the title compound of Preparation 40 (2.30 g, 12.7 mmol), triphenylphosphine (3.67 g, 14 mmol) and methanol (0.60 mL, 15 mmol) in tetrahydrofuran (20 mL) and the reaction stirred for 18 h at room temperature. The reaction mixture was concentrated under reduced pressure, the residue triturated with a 20% diethyl ether-:pentane solution and then filtered. The filtrate was concentrated under reduced pressure and the residue purified by flash column chromatography (diethyl ether:pentane 50:50 as eluant), to afford the title compound (2.2 g, 11.3 mmol) as a pale yellow oil.

$^1$H NMR (300 MHz, $CDCl_3$) δ=1.07 (3H, t), 1.86 (2H, m), 3.92 (3H, s), 4.38 (2H, t), 6.93 (1H, m), 8.15 (1H, d), 8.30 (1H, d).

Preparation 42

Methyl 5-Nitro-2-propoxynicotinate

The title compound was prepared in 32% yield (after crystallisation from methanol) from the title compound of Preparation 41, using the method of Preparation 20.

$^1$H NMR (300 MHz, $CDCl_3$) δ=1.04 (3H, t), 1.84 (2H, m), 3.92 (3H, s), 4.48 (2H, t), 8.88 (1H, s), 9.14 (1H, s).

Preparation 43

Methyl 5-Amino-2-propoxynicotinate

The title compound was prepared from the title compound of Preparation 42 by the method of Preparation 23.

$^1$H NMR (300 MHz, $CDCl_3$) δ=1.04 (3H, t), 1.80 (2H, m), 3.40 (2H, s), 3.89 (3H, s), 4.28 (2H, t), 7.57 (1H, s), 7.80 (1H, s). LRMS (TSP): 211 $(MH)^+$.

Preparation 44 tert-Butyl 3-Iodo-1-azetidinecarboxylate

A mixture of tert-butyl 3-[(methylsulfonyl)oxy]-1-azetidinecarboxylate (prepared as described in *Synlett* 1998, 379; 5.0 g, 19.9 mmol), and potassium iodide (16.5 g, 99.4 mmol) in N,N-dimethylformamide (25 mL), was heated at 10° C. for 42 h. The cooled mixture was partitioned between water and ethyl acetate, and the layers separated. The organic phase was dried over $MgSO_4$, concentrated under reduced pressure and the residue azeotroped with xylene. The crude product was purified by flash column chromatography (dichloromethane as eluant) to give the title compound, 3.26 g.

$^1$H NMR (300 MHz, $CDCl_3$) δ=1.43 (s, 9H), 4.28 (m, 2H), 4.46 (m, 1H), 4.62 (m, 2H). LRMS (TSP) 284 $(MH)^+$.

Preparation 45

N-[5-(Aminocarbonyl)-1-methyl-3-propyl-1H-pyrazol-4-yl]-2-ethoxy-5-nitronicotinamide The product of preparation 21 and 4-amino-1-methyl-3-propyl-1H-pyrazole-5-carboxamide (prepared as described in EP 526 004) were combined using the method of preparation 13.

m.p. 251–3° C.; 1H NMR (300 MHz, $d_6$-DMSO): δ=0.9 (t, 3H), 1.38 (t, 3H), 1.5–1.7 (m, 2H), 2.5–2.55 (m, partially obscured by DMSO peak), 3.9 (s, 3H), 4.5–4.65 (m, 2H), 7.3 (br s, 1H), 7.7 (br s, 1H), 8.7 (s, 1H), 9.2 (s, 1H), 9.7 (s, 1). LRMS (ES negative ion) 375 $(M-H)^-$. Analysis: Found C, 50.99; H, 5.36; N, 22.33. Calcd for $C_{16}H_{20}N_6O_5$: C, 51.06; H, 5.36; N, 22.33%.

Preparation 46a

3-Ethyl-1-[2-(4-morpholinyl)ethyl]-4-nitro-1H-pyrazole-5-carboxamide and

Preparation 46b

5-Ethyl-1-[2-(4-morpholinyl)ethyl]-4-nitro-1H-pyrazole-3-carboxamide

Using the method of preparations 10a and 10b, the title compounds were prepared using 4-(2-chloroethyl)morpholine.HCl. The regiochemistry was determined by nOe studies.

3-Ethyl-1-[2-(4-morpholinyl)ethyl]-4-nitro-1H-pyrazole-5-carboxamide m.p. 133° C. 1H NMR (300 MHz, CDCl$_3$): δ=1.25 (t, 3H), 2.4–2.45 (m, 4H), 2.75 (t, 2H), 2.9 (q, 2H), 3.55–3.65 (m, 4H), 4.45 (t, 2H), 6.4 (br s, 1H), 7.6 (br s, 1H). LRMS (TSP) 298 (MH$^+$). Analysis: Found C, 48.47; H, 6.47; N, 23.49. Calcd for C$_{12}$H$_{19}$N$_5$O$_4$: C, 48.48; H, 6.44; N, 23.56%.

5-Ethyl-1-[2-(4-morpholinyl)ethyl]-4-nitro-1H-pyrazole-3-carboxamide m.p. 144.9–147.1° C. 1H NMR (400 MHz, CDCl$_3$): δ=1.25 (t, 3H), 2.4–2.5 (m, 4H), 2.8 (t, 2H), 3.0 (q, 2H), 3.55–3.65 (m, 4H), 4.2 (t, 2H), 6.0 (br s, 1H), 7.25 (br s, 1H). LRMS (TSP) 298 (MH$^+$). Analysis: Found C, 48.49; H, 6.47; N, 23.35. Calcd for C$_{12}$H$_{19}$N$_5$O$_4$: C, 48.48; H, 6.44; N, 23.56%.

Preparation 47

4-Amino-3-ethyl-1-[2-(4-morpholinyl)ethyl]-1H-pyrazole-5-carboxamide

The title compound of preparation 46a (16 g, 54 mmol) was dissolved in ethanol (320 ml) and treated with 10% Pd on C (1.5 g) before stirring at RT under 60 psi of hydrogen for 6 h. The catalyst was removed by filtration through Arbocel*, the filtrate concentrated in vacuo to an oil which afforded the title compound as a pink solid after trituration with diisopropyl ether (13.18 g, 49.3 mmol).

m.p. 115–7° C. 1H NMR (300 MHz, CDCl$_3$): δ=1.2 (t, 3H), 2.4–2.5 (m, 4H), 2.55 (q, 2H), 2.8 (t, 2H), 3.4 (s, 2H), 3.6–3.65 (m, 4H), 4.45 (t, 2H). LRMS (TSP) 268 (MH$^+$). Analysis: Found C, 53.89; H, 8.04; N, 25.86. Calcd for C$_{12}$H$_{21}$N$_5$O$_2$: C, 53.92; H, 7.92; N, 26.20%.

Preparation 48

N-{5-(Aminocarbonyl)-3-ethyl-1-[2-(4-morpholinyl)ethyl]-1H-pyrazol-4-yl}-5-iodo-2-proroxynicotinamide The title compound was prepared by the method of preparation 13 using the title compounds of preparations 31 and 47.

m.p. 180–180.5° C. 1H NMR (300 MHz, CDCl$_3$): δ=1.05 (t, 3H), 1.25 (t, 3H), 1.85–1.95 (m, 2H), 2.4–2.55 (m, 4H), 2.6 (q, 2H), 2.8 (t, 2H), 3.55–3.7 (m, 4H), 4.5 (t, 2H), 4.55 (t, 2H), 5.6 (br s, 1H), 8.25 (br s 1H), 8.5 (s, 1H), 8.75 (s, 1H), 9.5 (s, 1H). LRMS (TSP) 558 (MH$^+$). Analysis: Found C, 45.05; H, 5.23; N, 14.59. Calcd for C$_{21}$H$_{29}$N$_6$O$_4$I.0.2H$_2$O: C, 45.04; H, 5.29; N, 15.01%.

Preparation 49

N-{5-(Aminocarbonyl)-3-ethyl-1-[2-(4-morpholinyl)ethyl]-1H-pyrazol-4-yl}-2-ethoxy-5-iodonicotinamide The title compound was prepared by the method of preparation 13 from the products of preparations 31 and 47 in 88% yield (4.0 g).

1H NMR (300 MHz, CDCl$_3$): δ=1.2 (t, 3H), 1.5 (t, 3H), 2.4–2.5 (m, 4H), 2.6 (q, 2H), 2.8 (t, 2H), 3.6–3.7 (m, 4H), 4.45 (t, 2H), 4.65 (q, 2H), 5.6 (br s, 1H), 8.3 (br s, 1H), 8.45 (s, 1H), 8.77 (s, 1H), 9.55 (s, 1H). LRMS (TSP) 544 (MH$^+$).

Preparation 50

N-[3-(Aminocarbonyl)-1-(4-cyanobenzyl)-5-ethyl-1H-pyrazol-4-yl]-2-ethoxy-5-iodonicotinamide The title compound was prepared from the title compound of preparation 38 and 4-cyanobenylchloride in 83% yield (988 mg).

1H NMR (300 MHz, CDCl$_3$): δ=1.2 (t, 3H), 1.55 (t, 3H), 2.8 (q, 2H), 3.0 (s, 3H), 3.1 (s, 3H), 4.65 (q, 2H), 4.95 (s, 2H), 5.2 (br s, 1H), 6.6 (br s, 1H), 8.40 (d, 1H), 8.80 (d, 1H), 10.45 (br s, 1H). LRMS (TSP) 514 (MH$^+$), 537 (MNa$^+$).

Preparation 51

N-[3-(Aminocarbonyl)-5-ethyl-1-(2-pyridinylmethyl)-1H-pyrazol-4-yl]-5-iodo-2-propoxynicotinamide The title compound was prepared using the method of preparation 13 and the title compounds of preparations 31 and 4-amino-5-ethyl-1-(2-pyridinylmethyl)-1H-pyrazole-3-carboxamide (WO 9849166).

1H NMR (400 MHz, CDCl$_3$): δ=1.00 (m, 6H), 1.90 (m, 2H), 2.80 (q, 2H), 4.50 (t, 2H), 5.20 (s, 1H), 5.40 (s, 2H), 6.60 (s, 1H), 6.90 (d, 1H), 7.20 (m, 1H), 7.60 (app. t, 1H), 8.40 (d, 1H), 8.60 (m, 1H), 8.75 (s, 1H), 10.40 (s, 1H); LRMS (ES-positive ion) 535 (MH$^+$), (ES-negative ion) 533 (M−H); Anal. Found C, 47.53; H, 4.41; N, 15.69. Calcd for C$_{21}$H$_{23}$O$_3$N$_6$I: C, 47.20; H, 4.34; N, 15.73.

Preparation 52 tert-Butyl 3-(3-(Aminocarbonyl)-5-ethyl-4-{[(5-iodo-2-propoxy-3-pyridinyl)carbonyl]amino}-1H-pyrazol-1-yl)-1-azetidinecarboxylate The title compound was prepared by the method of preparation 17c using the products from preparations 32 and 44.

1H NMR (400 MHz, DMSO): δ=0.95 (t, 3H), 1.05 (t, 3H), 1.40 (s, 9H), 1.78–1.88 (m, 2H), 2.68 (q, 2H), 4.22–4.35 (m, 4H), 4.40 (t, 2H), 5.33 (t, 1H), 7.35 (bs, 1H), 7.52 (bs, 1H), 8.40 (s, 1H), 8.55 (s, 1H), 10.10 (s, 1H); LRMS (TSP-positive ion) 373.2 (MH$^+$-BOC and I); Anal. Found C, 45.11; H, 5.07; N, 13.56; Calcd for C$_{23}$H$_{31}$O$_5$N$_6$I.0.2 DCM: C, 45.28; H, 5.14; N, 13.66.

Preparation 53 tert-Butyl 4-(3-(Aminocarbonyl)-5-ethyl-4-{[(5-iodo-2-propoxy-3-pyridinyl)carbonyl]amino}-1H-pyrazol-1-yl)-1-piperidinecarboxylate The title compound was prepared using the method of preparation 17b, and the product from preparation 32 in 52% yield (10.3 g).

1H NMR (400 MHz, CDCl$_3$): δ=1.00 (t, 3H), 1.10 (t, 3H), 1.45 (s, 9H), 1.85–1.95 (m, 4H), 2.10 (m, 2H), 2.84 (m, 4H), 4.10–4.30 (m, 3H), 4.50 (t, 2H), 5.10 (s, 1H), 6.60 (s, 1H), 8.40 (s, 1H), 8.72 (s, 1H), 10.30 (s, 1H); LRMS (TSP-positive ion) 628 (MH$^+$); Anal. Found C, 47.55; H, 5.71; N, 13.07; Calcd for C$_{25}$H$_{35}$O$_5$N$_6$I.0.3H$_2$O, C, 47.52; H, 5.68; N, 13.30.

Preparation 54a 1-(Cyclopropylmethyl)-3-ethyl-4-nitro-1H-pyrazole-5-carboxamide and Preparation 54b 1-(Cyclopropylmethyl)-5-ethyl-4-nitro-1H-pyrazole-3-carboxamide A suspension of 3-ethyl-4-nitro-1H-pyrazole-5-carboxamide (prepared as in WO98/49166) (40.0 g, 217 mmol) in dry DMF (300 ml) was treated with cesium carbonate (77.8 g, 239 mmol). To this, in a single portion, was added cyclopropylmethyl bromide (22.9 ml, 239 mmol) and the resultant suspension stirred at RT for 6 h. After condensation in vacuo, the residue was partioned between ethyl acetate (200 ml) and water (200 ml), and the insoluble material removed by filtration. The solid was partioned between water (200 ml) and methylene chloride (200 ml), and undissolved solid removed by filtration. Combined organics were washed with brine (100 ml), dried over $MgSO_4$, and condensed to a solid (40 g). The two regioisomers were separated by crystallisation of the crude mixture. The more lipophilic component (Rf=0.27, methylene chloride:methanol 98:2) crystallising from a mixture of methylene chloride (50 ml) and diisopropylether (200 ml) to give 1-(cyclopropylmethyl)-3-ethyl-4-nitro-1H-pyrazole-5-carboxamide (12 g, 50 mmol). Crystallisation of the mother liquors from acetonitrile gave the more polar component (Rf=0.19, methylene chloride:methanol 98:2) (10 g, 42 mmol) which was confirmed as the 1-(cyclopropylmethyl)-5-ethyl-4-nitro-1H-pyrazole-3-carboxamide by nOe experiements. The mother liquors contained further material as a mixture of regioisomers (20 g, 84 mmol).

1-(Cyclopropylmethyl)-3-ethyl-4-nitro-1H-pyrazole-5-carboxamide

1H NMR (300 MHz, $CDCl_3$): δ=0.38–0.42 (m, 2H), 0.5–0.6 (m, 2H), 1.2 (t, 3H), 1.3 (m, 1H), 2.9 (q, 2H), 4.2 (d, 2H), 6.0 (br s, 1H), 7.15 (br s, 1H). LRMS (TSP) 239 ($MH^+$). Analysis: Found C, 50.38; H, 5.93; N, 23.12. Calcd for $C_{10}H_{14}N_4O_3$: C, 50.41; H, 5.92; N, 23.52%.

1-(Cyclopropylmethyl)-5-ethyl-4-nitro-1H-pyrazole-3-carboxamide

1H NMR (300 MHz, $CDCl_3$): δ=0.35–0.41 (m, 2H), 0.6–0.65 (m, 2H), 1.25 (t, 3H), 1.2–1.3 (m, 1H), 2.95 (q, 2H), 4.0 (d, 2H), 5.85 (br s, 1H), 7.2 (br s, 1H). LRMS (TSP) 239 ($MH^+$). Analysis: Found C, 50.30; H, 5.90; N, 23.39. Calcd for $C_{10}H_{14}N_4O_3$: C, 50.41; H, 5.92; N, 23.52%.

Preparation 55

4-Amino-1-(cyclopropylmethyl)-5-ethyl-1H-pyrazole-3-carboxamide

The title compound was prepared following the method of preparation 11 using 1-(cyclopropylmethyl)-5-ethyl-4-nitro-1H-pyrazole-3-carboxamide (from preparation 54b) in 92% yield (7.7 g).

m.p. 143–145° C. 1H NMR (400 MHz, $CDCl_3$): δ=0.35–0.42 (m, 4H), 1.18 (t, 3H), 1.25–1.35 (m, 1H), 2.55 (q, 2H), 2.8 (br s, 2H), 4.33 (s, 1H), 4.36 (s, 1H). LRMS (TSP) 209 ($MH^+$). Analysis: Found C, 57.58; H, 7.78; N, 26.76. Calcd for $C_{10}H_{16}N_4O$: C, 57.67; H, 7.74; N, 26.91%.

Preparation 56

5-Acetyl-2-ethoxynicotinic Acid

Palladium(II) acetate (919 mg, 4.08 mmol), butyl vinyl ether (18.9 ml, 146.5 mmol) and tri-otolyl phosphine (2.50 g, 8.16 mmol) were added to a stirred solution of the title compound of preparation 37 (15.0 g, 51.2 mmol) and triethylamine (10.5 ml, 81.9 mmol) in acetonitrile (150 ml). The mixture was refluxed for 3 h under nitrogen, and then stirred at RT for 16 h. The solvent was removed in vacuo, and the residue taken up in 6N HCl (80 ml), and stirred at RT for 40 min. The mixture was then diluted with water and ethyl acetate, filtered through Arbocel* and the organic layer was separated. The aqueous phase was extracted with ethyl acetate (3×200 ml), and the combined organics were dried ($MgSO_4$) and concentrated in vacuo. The crude product was then taken up in $NaHCO_3$ (sat. aq., 500 ml) and ethyl acetate (200 ml). The organic layer was separated, the aqueous layer washed with dichloromethane (200 ml), acidified with conc. HCl to pH 1, and extracted with ethyl acetate (5×200 ml). The combined extracts were washed with brine (200 ml), dried ($MgSO_4$) and concentrated in vacuo. Purification of the crude product by column chromatography (99:1:0.25 ethyl acetate:methanol:acetic acid as eluent), and then recrystallisation from hot diisopropylether gave the title compound as a yellow solid (3.91 g, 18.9 mmol).

1H NMR (400 MHz, $CDCl_3$): δ=1.60 (t, 3H), 2.60 (s, 3H), 4.80 (q, 2H), 8.93 (s, 1H), 8.96 (s, 1H). LRMS (ES-negative) 208 ($MH^-$).

Preparation 57

Methyl 2-Ethoxy-5-iodonicotinate

Concentrated sulphuric acid (2 ml) was added to a stirring suspension of the title compound of preparation 37 (40 g, 137 mmol) in methanol (250 ml), and the mixture refluxed for 2 h. A further aliquot of sulphuric acid (1 ml) was added, and the mixture refluxed for a further 2 h, before standing at −18° C. for 16 h. The off-white precipitate was filtered off and washed with methanol, dissolved in ethyl acetate (500 ml) and the solution, washed with $NaHCO_3$ (sat. aq., 200 ml) and brine (200 ml). The organic layer was dried over $MgSO_4$, and concentrated in vacuo to give the title compound as an off-white solid (34 g, 111 mmol).

m.p. 67–69° C.; 1H NMR (400 MHz, $CDCl_3$): δ=1.41 (t, 3H), 3.90 (s, 3H), 4.43 (q, 2H), 8.36 (s, 1H), 8.44 (s, 1H); LRMS (TSP-positive) 308 ($MH^+$); Anal. Found C, 35.06; H, 3.18; N, 4.45. Calcd for $C_9H_{10}O_3NI$: C, 35.20; H, 3.28; N, 4.56.

Preparation 58

Methyl 5-Acetyl-2-ethoxynicotinate

Palladium(II) acetate (877 mg, 3.90 mmol), butyl vinyl ether (19.8 ml, 0.15 mol) and tri-otolyl phosphine (2.37 g, 7.81 mmol) were added to a stirring solution of the title compound of preparation 57 (15.0 g, 48.8 mmol) and triethylamine (10.9 ml, 78.1 mmol) in acetonitrile (150 ml). The mixture was refluxed for 1.5 h under nitrogen, and then the solvent removed in vacuo. The residue was taken up in 6N HCl (60 ml), and stirred at RT for 1 h. The mixture was then diluted with water, and extracted with ethyl acetate (3×250 ml). The combined organic layers were dried ($MgSO_4$) and concentrated in vacuo. The brown residue was purified by flash column chromatography (methylene chloride as eluent) to give an off-white solid, which was recrystallised from diisopropylether to yield the title compound as pale brown needles (5.3 g, 23.7 mmol).

m.p. 111–112° C.; 1H NMR (400 MHz, $CDCl_3$): δ=1.41 (t, 3H), 2.56 (s, 3H), 3.89 (s, 3H), 4.54 (q, 2H), 8.62 (s, 1H), 8.83 (s, 1H); LRMS (TSP-positive) 224 ($MH^+$); Anal. Found C, 59.11; H, 5.80; N, 6.22. Calcd for $C_{11}H_{13}O_4N$: C, 59.19; H, 5.87; N, 6.27.

Preparation 59

5-Acetyl-2-ethoxynicotinic Acid

To a solution of the title compound of preparation 58 (7.15 g, 32.0 mmol) in dioxane (50 ml) was added a solution of sodium hydroxide (2.56 g, 64.1 mmol) in water (10 ml).

The mixture was stirred at RT for 2 h, after which it was concentrated in vacuo. The residue was partitioned between ethyl acetate (100 ml) and water (100 ml). The aqueous layer was separated, acidified with 2N HCl, and then extracted with ethyl actetate (3×100 ml). These combined organic extracts were washed with brine (100 ml), dried (MgSO$_4$) and concentrated in vacuo to yield the title compound as a yellow solid (6 g, 28.6 mmol).

m.p. 117–118° C.; 1H NMR (300 MHz, CDCl$_3$): δ=1.54 (t, 3H), 2.62 (s, 3H), 4.78 (q, 2H), 8.95 (br s, 2H); LRMS (ES-negative) 208 (MH$^-$); Anal. Found C, 57.32; H, 5.43; N, 6.53. Calcd for C$_{10}$H$_{11}$O$_4$N: C, 57.41; H, 5.30; N, 6.70.

Preparation 60

5-Acetyl-N-[3-(aminocarbonyl)-1-(cyclopropylmethyl)-5-ethyl-1H-pyrazol-4-yl]-2-ethoxynicotinamide A solution of the title compound of preparation 56 (800 mg, 3.82 mmol) and O-(7-azabenzotriazol-1-yl)-N,N,N',N'tetramethyluronium hexafluorphosphate (1.59 g, 4.40 mmol) in DMF (30 ml) was added to a solution of the title compound of preparation 55 (796 mg, 3.82 mmol) and diisopropylethylamine (3.33 ml, 19.1 mmol) in DMF (15 ml). After 1 h the DMF was removed in vacuo, and the residue was partitioned between ethyl acetate (200 ml) and water (200 ml). The organic layer was separated, washed with NaHCO$_3$ (sat. aq., 100 ml) and 1N HCl (aq., 100 ml), dried (MgSO$_4$) and concentrated in vacuo to give a beige solid. This was recrystallised from isopropyl alcohol to yield the title compound as a pale brown solid (1.1 g, 2.75 mmol).

m.p. 238–240° C.; 1H NMR (400 MHz, CDCl$_3$): δ=0.39 (m, 2H), 0.60 (m, 2H), 1.18 (t, 3H), 1.26 (m, 1H), 1.53 (t, 3H), 2.58 (s, 3H), 2.92 (q, 2H), 3.95 (d, 2H), 4.74 (q, 2H), 5.26 (br s, 1H), 6.64 (br s, 1H), 8.85 (s, 1H), 9.00 (s, 1H), 10.48 (br s, 1H). LRMS (ES-positive) 400 (MH$^+$); Anal. Found C, 59.34; H, 6.41; N, 16.80. Calcd for C$_{20}$H$_{25}$O$_4$N$_5$.0.3H$_2$O.0.2IPA: C, 59.35; H, 6.58; N, 16.80.

Preparation 61

5-Acetyl-N-[3-(aminocarbonyl)-5-ethyl-1H-pyrazol-4-yl]-2-ethoxynicotinamide

A solution of the title compound from preparation 59 (5.70 g, 27.3 mmol) and O-(7-azabenzotriazol-1-yl)-N,N,N',N'tetramethyluronium hexafluorphosphate (10.9g, 28.6 mmol) in methylene chloride (100 ml) was added to a solution of 4-amino-3-ethyl-1H-pyrazole-5-carboxamide (prepared as WO 98/49166) (4.20 g, 27.3 mmol) and diisopropylethylamine (23.7 ml, 136.2 mmol) in methylene chloride (115 ml). After 1 h the mixture was diluted with brine (100 ml) and washed with NaHCO$_3$ (sat. aq., 100 ml) and then HCl (2N, 100 ml). Each aqueous layer was back-extracted with dichloromethane (100 ml), and the combined organics washed with brine (100 ml), dried (MgSO$_4$) and concentrated in vacuo. An analytical sample of the title compound was obtained by trituration with ethyl acetate, followed by recrystallisation from ethanol, while the remainder was purified by flash column chromatography (95:5 methylene chloride:methanol as eluent) to yield the title compound (total weight=7.8 g, 22.5 mmol).

m.p. 217–219° C.; 1H NMR (400 MHz, DMSO): δ=1.12 (t, 3H), 1.42 (t, 3H), 2.58 (s, 3H), 2.73 (q, 2H), 4.61 (q, 2H), 7.26 (bs, 1H), 7.48 (bs, 1H), 8.72 (s, 1H), 8.90 (s, 1H), 10.52 (bs, 1H), 12.93 (bs, 1H). LRMS (TSP-positive) 346.2 (MH$^+$); Anal. Found C, 55.45; H, 5.64; N, 19.91. Calcd for C$_{16}$H$_{19}$O$_4$N$_5$: C, 55.65; H, 5.55; N, 20.28.

Preparation 62 tert-Butyl 4-[4-{[(5-Acetyl-2-ethoxy-3-pyridinyl)carbonyl]amino}-3-(aminocarbonyl)-5-ethyl-1H-pyrazol-1-yl]-1-piperidinecarboxylate The title compound from preparation 61 (4.32 g, 12.5 mmol) and cesium carbonate (4.90 g, 15.0 mmol) were dissolved in DMF (60 ml), and 1-(tert-butoxycarbonyl)-4-piperidinylmethane sulphonate (Bioorg. Med. Chem. Lett. 1999, 9, 1285) (4.20 g, 15.0 mmol) was added in one portion. The mixture was stirred at 100° C. under nitrogen for 6 h, after which additional 1-(tert-butoxycarbonyl)-4-piperidinylmethane sulphonate (1.75 g, 6.26 mmol) and cesium carbonate (2.00 g, 6.26 mmol) were added. The mixture was heated at 60° C. for a further 16 h. The mixture was concentrated in vacuo, and the residue was partitioned between ethyl acetate (200 ml) and water (200 ml). Brine (50 ml) was then added, the organic layer separated and the aqueous extracted further with ethyl acetate (2×100 ml). The combined organic layers were dried (MgSO$_4$), and concentrated in vacuo. The crude product was purified by column chromatography (first with 98:2 methylene chloride methanol; and repeated with 1:1 to 0:1 pentane:ethyl acetate) to yield the title compound as a white solid (3.8 g, 7.19 mmol).

m.p. 197–202° C.; 1H NMR (400 MHz, CDCl$_3$): δ=1.24 (t, 3H), 1.49 (s, 9H), 1.58 (t, 3H), 1.92 (m, 2H), 2.15 (m, 2H), 2.60 (s, 3H), 2.90 (m, 2H), 2.93 (q, 2H), 4.22 (m, 1H), 4.29 (m, 2H), 4.78 (q, 2H), 5.26 (bs, 1H), 6.66 (bs, 1H), 8.88 (s, 1H), 9.03 (s, 1H), 10.49 (bs, 1H); LRMS (ES-positive) 529 (MH$^+$); Anal. Found C, 58.04; H, 6.85; N, 15.39. Calcd for C$_{26}$H$_{36}$O$_6$N$_6$.0.5H$_2$O: C, 58.09; H, 6.94; N, 15.63.

Preparation 63

5-Acetyl-N-{5-(aminocarbonyl)-3-ethyl-1-[(1-methyl-1H-imidazol-2-yl)methyl]-1H-pyrazol-4-yl}-2-ethoxynicotinamide The title compound was prepared by the method of preparation 13 using 4-amino-3-ethyl-1-[(1-methyl-1H-imidazol-2-yl)methyl]-1H-pyrazole-5-carboxamide (prepared as in WO 9954333) and the title compound of preparation 59.

1H NMR (400 MHz, CDCl$_3$): δ=1.25 (m, 6H), 2.60 (s, 3H), 2.70 (q, 2H), 3.95 (s, 3H), 4.80 (q, 2H), 5.60 (s, 2H), 5.80 (br s, 1H), 6.85 (s, 1H), 6.90 (s, 1H), 8.90 (s, 1H), 9.00 (s, 1H), 9.80 (br s, 1H), 10.20 (s, 1H). LRMS (ES-positive) 440 (MH$^+$); (ES-negative) 438 (ES$^-$).

Preparation 64

4-{[1-(5-Iodo-2-isobutoxy-3-pyridinyl)vinyl]amino}-1-methyl-5-propyl-1H-pyrazole-3-carboxamide The title compound was prepared by the method of preparation 13 using the products of preparations 3 and 9.

1H NMR (300 MHz, CDCl$_3$): δ=0.9 (3H, t), 1.0 (6H, t), 1.5–1.65 (2H, m), 2.2–2.45 (1H, m), 2.82 (2H, t), 3.85 (3H, s), 4.35 (2H, d), 5.2 (1H, br s), 6.6 (1H, br s), 8.4 (1H, d), 8.75 (1H, d), 10.2 (1H, br s). LRMS (TSP) 486 (MH$^+$).

SYNTHESIS OF THE COMPOUNDS OF FORMULAE IA AND IB

Example 1

5-(2-Butoxy-5-iodo-3-pyridinyl)-3-ethyl-2-(2-methoxyethyl)-2,6-dihydro-7H-pyrazolo[4,3-d]pyrimidin-7-one Potassium hexamethyldisilazide (46 mg, 0.23 mmol) was added to N-[3-(aminocarbonyl)-5-ethyl-1-(2-methoxyethyl)-1H-pyrazol-4-yl]-2-butoxy-5-iodonicotinamide (Preparation 13) (100 mg, 0.19 mmol) in degassed n-butanol (2 mL) and the solution stirred under a nitrogen atmosphere. The reaction was heated at reflux for 9 h and then cooled. The butanol was removed in vacuo and the residue partitioned between dichloromethane and 1N hydrochloric acid. The organic phase was separated and washed with brine, dried (MgSO$_4$) and concentrated to give a white solid. Trituration with ethyl acetate gave the title compound (40 mg, 42%) as a white solid.

$^1$H NMR (400 MHz, CDCl$_3$): δ=1.00 (t, 3H), 1.40 (t, 3H), 1.55 (m, 2H), 1.90 (m, 2H), 3.05 (q, 2H), 3.30 (s, 3H), 3.90 (t, 2H), 4.40 (t, 2H), 4.55 (t, 2H), 8.40 (s, 1H), 9.00 (s, 1H), 10.70 (s, 1H). LRMS (TSP): 498.1 (MH$^+$).

Example 2

Methyl 6-Butoxy-5-[3-ethyl-2-(2-methoxyethyl)-7-oxo-6,7-dihydro-2H-pyrazolo[4,3-d]pyrimidin-5-yl]nicotinate 5-(2-Butoxy-5-iodo-3-pyridinyl)-3-ethyl-2-(2-methoxyethyl)-2,6-dihydro-7H-pyrazolo[4,3-d]pyrimidin-7-one (Example 1) (100 mg, 0.20 mmol), palladium acetate (31.6 mg, 0.141 mmol), 1,2-bis(diphenylphosphino)propane (37 mg, 0.09 mmol) and triethylamine (0.22 mL, 1.56 mmol) were added to methanol (5 mL) and dimethylsulfoxide (0.7 mL). The reagents were stirred together under an atmosphere of carbon monoxide (482.6 kPa (70 psi)) at 75° C. for 14 h. The reaction mixture was filtered through Celite® and the solvent removed in vacuo. The product was purified by flash column chromatography (gradient elution from dichloromethane to 2% methanol:dichloromethane) to give the title compound (89 mg, 100%).

$^1$H NMR (300 MHz, CDCl$_3$): δ=1.00 (t, 3H), 1.40 (t, 3H), 1.50 (m, 2H), 1.90 (m, 2H), 3.05 (q, 2H), 3.25 (s, 3H), 3.90 (t, 2H), 4.00 (s, 3H), 4.40 (t, 2H), 4.60 (t, 2H), 8.85 (s, 1H), 9.25 (s, 1H), 10.60 (s, 1H). LRMS (TSP): 430.2 (MH$^+$).

Example 3

6-Butoxy-5-[3-ethyl-2-(2-methoxyethyl)-7-oxo-6,7-dihydro-2H-pyrazolo[4,3-d]pyrimidin-5-yl]nicotinic Acid Sodium hydroxide (0.52 mL of 2N) was added to a solution of methyl 6-butoxy-5-[3-ethyl-2-(2-methoxyethyl)-7-oxo-6,7-dihydro-2H-pyrazolo[4,3-d]pyrimidin-5-yl]nicotinate (Example 2) (226 mg, 0.53 mmol) in dioxane. The solution was stirred for 14 h. The pH was adjusted to pH 2–3 with hydrochloric acid (1N) and the mixture concentrated to dryness. Hot ethanol was added to the solid and the slurry filtered. The ethanol solution was concentrated and the resulting solid was washed with dichloromethane resulting in the title compound (156 mg, 72%).

$^1$H NMR (300 MHz, CDCl$_3$): δ=1.00 (t, 3H), 1.40 (t, 3H), 1.55 (m, 2H), 1.90 (m, 2H), 3.10 (q, 2H), 3.30 (s, 3H), 3.90 (t, 2H), 4.55 (t, 2H), 4.65 (t, 2H), 8.95 (s, 1H), 9.25 (s, 1H), 10.90 (s, 1H). LRMS (TSP): 416.5 (MH$^+$).

Example 4

5-[2-Butoxy-5-(hydroymethyl)-3-pyridinyl]-3-ethyl-2-(2-methoxyethyl)-2,6-dihydro-7H-pyrazolo[4,3-d]pyrimidin-7-one Carbonyldiimidazole (47 mg, 0.24 mmol) was added to a stirred solution of 6-butoxy-5-[3-ethyl-2-(2-methoxyethyl)-7-oxo-6,7-dihydro-2H-pyrazolo[4,3-d]pyrimidin-5-yl]nicotinic acid (Example 3) (100 mg, 0.24 mmol) in tetrahydrofuran (3 mL) under a nitrogen atmosphere. The mixture was stirred at room temperature for 1 h. A further 20 mg of carbonyldiimidazole was added and the mixture stirred for a further 1 h. The mixture was cooled to 0° C. and water (0.3 mL) added followed by sodium borohydride (27.4 mg, 0.72 mmol). Stirring was continued for 1 h. The reaction mixture was quenched with water and extracted from 2 N HCl with ethyl acetate. The organic fractions were washed with brine, dried (MgSO$_4$) and evaporated to give the crude product. The crude product was purified by flash column chromatography (gradient elution from dichloromethane to 5% methanol:dichloromethane) to give the title compound (20 mg, 21%).

$^1$H NMR (300 MHz, CDCl$_3$): δ=1.00 (t, 3H), 1.40 (t, 3H), 1.50 (m, 2H), 1.90 (m, 2H), 2.20 (br s, 1H), 3.05 (q, 2H), 3.30 (s, 3H), 3.90 (t, 2H), 4.40 (t, 2H), 4.55 (t, 2H), 4.75 (s, 2H), 8.20 (s, 1H), 8.80 (s, 1H), 10.80 (s, 1H). LRMS (TSP): 402.4 (MH$^+$); Analysis: found C, 59.06; H, 6.79; N, 17.01; C$_{20}$H$_{27}$N$_5$O$_4$.0.3H$_2$O requires C, 59.04; H, 6.84; N, 17.21.

Example 5

6-Butoxy-5-[3-ethyl-2-(2-methoxyethyl)-7-oxo-6,7-dihydro-2H-pyrazolo[4,3-d]pyrimidin-5-yl]-N-methoxy-N-methylnicotinamide 6-Butoxy-5-[3-ethyl-2-(2-methoxyethyl)-7-oxo-6,7-dihydro-2H-pyrazolo-[4,3-d]pyrimidin-5-yl]nicotinic acid (Example 3) (200 mg, 0.48 mmol) was dissolved in dichloromethane and 1-hydroxybenzotriazole hydrate (78 mg, 0.58 mmol) and 1-(3-dimethylaminopropyl)-3-ethyl-carbodiimide hydrochloride (120 mg, 0.58 mmol) were added followed by diisopropylethylamine (0.34 mL, 1.95 mmol). N,O-dimethylhydroxyl-amine hydrochloride (56.3 mg, 0.58 mmol) was added and the mixture stirred at room temperature for 14 h. A further 0.29 mmol of 1-hydroxybenzotriazole hydrate and 1-(3-dimethylaminopropyl)-3-ethyl-carbodiimide hydrochloride were added and the reaction stirred for a further 3 h. The reaction mixture was diluted with further dichloromethane, washed with water, dried (MgSO$_4$) and concentrated. Purification by flash column chromatography (gradient elution from dichloromethane to 5% methanol:dichloromethane) gave the title compound (178 mg, 81%).

$^1$H NMR (300 MHz, CDCl$_3$): δ=1.00 (t, 3H), 1.40 (t, 3H), 1.60 (m, 2H), 1.95 (m, 2H), 3.05 (q, 2H), 3.25 (s, 3H), 3.40 (s, 3H), 3.60 (s, 3H), 3.90 (t, 2H), 4.40 (t, 2H), 4.60 (t, 2H), 8.65 (s, 1H), 9.20 (s, 1H), 10.75 (s, 1H). LRMS (TSP): 459.7 (MH$^+$); Analysis: found C, 57.80; H, 6.56; N, 18.02; C$_{22}$H$_{30}$N$_6$O$_5$ requires C, 57.63; H, 6.59; N, 18.33.

Examples 6 to 10

The following compounds were made by the same method as Example 5

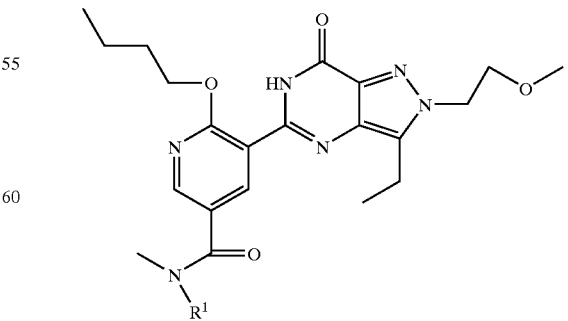

from the compound of Example 3 and the appropriate amine.

| Ex. | R1 | LRMS (MH+) | 1H NMR |
|---|---|---|---|
| 6[1] | 4-(NHSO2Me)-phenyl-CH2CH2- | 626.7 | (300 MHz, CDCl3) δ: 1.00(t, 3H), 1.40 (m, 3H), 1.50(m, 2H), 1.90(m, 2H), 2.80–3.20(m, 10H), 3.30(s, 3H), 3.40–3.80(m, 2H), 3.85(t, 2H), 4.40(t, 2H), 4.60(t, 2H), 6.80–9.80(m, 7H), 10.80 (s, 1H). |
| 7[2] | 2-pyridyl-CH2CH2- | 534.5 | (300 MHz, CDCl3) δ: 1.00(t, 3H), 1.40 (t, 3H), 1.50(m, 2H), 1.90(m, 2H), 3.00 (q, 2H), 3.20(s, 3H), 3.25(s, 3H), 3.50 (m, 2H), 3.80(t, 2H), 3.90(m, 2H), 4.40 (t, 2H), 4.60(t, 2H), 7.70(m, 1H), 7.80 (m, 1H), 8.25(m, 2H), 8.80(m, 2H). |
| 8[3] | 2,3-dihydro-1,4-benzodioxin-2-yl-CH2- | 577.7 | (300 MHz, CDCl3) δ: 1.00(t, 3H), 1.40 (t, 3H), 1.55(m, 2H), 1.90(m, 2H), 3.00 (q, 2H), 3.20(s, 3H), 3.30(s, 3H), 3.70 (m, 1H), 3.80(t, 2H), 4.10(m, 2H), 4.40 (m, 1H), 4.45(m, 3H), 4.60(t, 2H), 6.95 (m, 4H), 8.40(s, 1H), 8.80(s, 1H), 10.75(s, 1H). |
| 9[4] | Me2N-CH2CH2- | 500.5 | (300 MHz, CDCl3) δ: 1.00(t, 3H), 1.40 (t, 3H), 1.55(m, 2H), 1.90(m, 2H), 3.00 (s, 3H), 3.05(q, 2H), 3.0–3.l(m, 2H), 3.20(s, 3H), 3.30(s, 3H), 3.45(m, 2H), 3.80(t, 2H), 3.90(m, 2H), 4.40(t, 2H), 4.60(t, 2H), 8.40(s, 1H), 8.80(s, 1H), 12.0(br s, 1H). |
| 10[5] | 1-oxo-2(1H)-phthalazinyl-CH2CH2- | 601.7 | (300 MHz, CDCl3) δ: 1.00(t, 3H), 1.40 (t, 3H), 1.55(m, 2H), 1.85(m, 2H), 2.60 (br s, 2H), 2.90–3.30 m, 4H), 3.30(s, 3H), 3.90–4.10(m, 4H), 4.40(t, 2H), 4.60(br s, 3H), 7.40–8.30(m, 5H), 8.40 (s, 1H), 8.80(s, 1H), 10.75(br s, 1H). |

[1] = N-{4-[2-(methylamino)ethyl]phenyl}methanesulfonamide (EP 245 997) was the amine used
[2] = 2-(2-methylaminoethyl)pyridine was the amine used
[3] = 2,3-dihydro-1,4-benzodioxin-2-yl-N-methylmethanamine (Gazz. Chim. Ital. 83; 1953; 144; 148) was the amine used.
[4] = N,N,N'-trimethylethylenediamine was the amine used.
[5] = 2-[2-(methylamino)ethyl]-1-(2H)-phthalazinone (EP 242 173) was the amine used.

Example 11

5-{2-Butoxy-5-[3-(trifluoromethyl)phenyl]-3-pyridinyl}-3-ethyl-2-(2-methoxyethyl)-2,6-dihydro-7H-pyrazolo[4,3-d]pyrimidin-7-one 5-(2-Butoxy-5-iodo-3-pyridinyl)-3-ethyl-2-(2-methoxyethyl)-2,6-dihydro-7H-pyrazolo[4,3-d]pyrimidin-7-one (Example 1) (140 mg, 0.28 mmol), K2CO3 (78 mg, 0.56 mmol) and 3-trifluoromethylboronic acid (60 mg, 0.34 mmol) were stirred together in aqueous dioxan under a nitrogen atmosphere. The mixture was immersed in a pre-heated oil bath at 120° C. for a few minutes and Pd(PPh3)4 (34 mg, 0.028 mmol) was added. The mixture was heated at reflux for 2 h and then cooled. The cooled mixture was concentrated and partitioned between ethyl acetate and water. This was then filtered through an Arbocel® pad to remove the palladium residues and the organic layer separated, washed with sodium bicarbonate solution then brine, dried (MgSO4) and concentrated. Recrystallisation from ethyl acetate gave the title compound (101 mg, 70%).

1H NMR (300 MHz, CDCl3): δ=1.00 (t, 3H), 1.40 (t, 3H), 1.60 (m, 2H), 2.00 (m, 2H), 3.05 (q, 2H), 3.25 (s, 3H), 3.90 (t, 2H), 4.45 (t, 2H), 4.65 (t, 2H), 7.60 (m, 2H), 7.80 (d, 1H), 7.85 (s, 1H), 8.50 (s, 1H), 8.95 (s, 1H), 10.85 (s, 1H). LRMS (ES): 516.1 (MH+). Analysis: found C, 60.21; H, 5.43; N, 13.48; $C_{26}H_{28}N_5O_5F_3$ requires C, 60.57; H, 5.47; N, 13.58.

Example 12

5-[2-Butoxy-5-(2-furyl)-3-pyridinyl]-3-ethyl-2-(2-methoxyethyl)-2,6-dihydro-7H-pyrazolo[4,3-d]pyrimidin-7-one Pd(PPh$_3$)$_4$ (46.5 mg, 0.04 mmol) was added to a stirred mixture of potassium carbonate (55 mg, 0.40 mmol), 2-furylboronic acid (54 mg, 0.48 mmol) and the title compound of Example 1 (200 mg, 0.40 mmol) in degassed dioxan/water (10 mL of 4:1 mixture). The mixture was heated at reflux for 2 h and cooled. The solvent was removed in vacuo and the residue triturated with ethyl acetate to give an orange solid. Purification by flash column chromatography (elution with 50:1 dichloromethane/methanol) gave the title compound as a cream solid (121 mg, 58%).

MP=154–155° C. $^1$H NMR (300 MHz, CDCl$_3$): δ=1.00 (t, 3H), 1.40 (t, 3H), 1.60 (m, 2H), 1.95 (m, 2H), 3.05 (q, 2H), 3.30 (s, 3H), 3.90 (t, 2H), 4.40 (t, 2H), 4.60 (t, 2H), 6.50 (s, 1H), 6.70 (s, 1H), 7.50 (s, 1H), 8.60 (s, 1H), 9.00 (s, 1H), 10.80 (s, 1H). LRMS (ES): 438.1 (MH$^+$).

Example 13

5-(2-Butoxy-5-[2-pyridyl]-3-pyridinyl)-3-ethyl-2-(2-methoxyethyl)-2,6-dihydro-7H-pyrazolo[4,3-d]pyrimidin-7-one 2-Tributyltin pyridine (192 mg, 0.52 mmol), lithium chloride (170 mg, 4.00 mmol), cuprous iodide (11.5 mg, 0.06 mmol), Pd(PPh$_3$)$_4$ (46.5 mg, 0.04 mmol) and the title compound of Example 1 (200 mg, 0.40 mmol) were stirred together in dioxan (10 mL) under a nitrogen atmosphere. The mixture was heated at reflux for 3.5 h, allowed to cool and the solvent removed in vacuo. The residue was taken up in ethyl acetate and shaken vigorously with 5% aqueous potassium fluoride solution for 10 min and the mixture filtered through Arbocel®. The organic layer was separated, washed with 5% aqueous potassium fluoride solution, saturated sodium bicarbonate solution and brine. The organics were dried (MgSO$_4$) and concentrated. The solid was partially purified by trituration with cold ethyl acetate and further purified by flash column chromatography (elution with 50:1 dichloromethane/methanol) to give the title compound (52 mg, 29%).

$^1$H NMR (300 MHz, CDCl$_3$): δ=1.00 (t, 3H), 1.40 (t, 3H), 1.55 (m, 2H), 1.95 (m, 2H), 3.10 (q, 2H), 3.30 (s, 3H), 3.90 (t, 2H), 4.45 (t, 2H), 4.60 (t, 2H), 7.30 (m, 1H), 7.80 (m, 2H), 8.75 (d, 1H), 8.90 (s, 1H), 9.30 (s, 1H), 10.80 (s, 1H). LRMS (ES): 449.2 (MH$^+$).

Example 14 (Preparative Example)

5-(2-Butoxy-5-trimethylsilylethynyl-3-pyridinyl)-3-ethyl-2-(2-methoxy-ethyl)-2,6-dihydro-7H-pyrazolo[4,3-d]pyrimidin-7-one The title compound from Example 1 (127 mg, 0.25 mmol) was suspended in triethylamine (2 mL) and trimethylsilylacetylene (38 mg, 0.39 mmol) and acetonitrile (2 mL to try and solubilise reactants). Pd(PPh$_3$)$_2$Cl$_2$ (5 mg, 0.006 mmol) and cuprous iodide (1.2 mg, 0.006 mmol) were added and the reaction mixture stirred. After 1 h a further portion of trimethylsilylacetylene (19 mg, 0.19 mmol) was added and stirring continued for 2 h. The solvent was evaporated and the residue partitioned between ethyl acetate and water. The organics were washed with brine, dried (MgSO$_4$) and concentrated to give a brown foam. Purification by flash column chromatography (gradient elution from 100% dichloromethane to 99% dichloromethane/methanol) gave the title compound as a light brown solid (108 mg).

$^1$H NMR (300 MHz, CDCl$_3$): δ=0.25 (s, 9H), 1.00 (t, 3H), 1.40 (t, 3H), 1.50 (m, 2H), 1.90 (m, 2H), 3.10 (q, 2H), 3.30 (s, 3H), 3.90 (t, 2H), 4.40 (t, 2H), 4.60 (t, 2H), 8.40 (s, 1H), 8.80 (s, 1H), 10.70 (s, 1H). LRMS (TSP): 468.3 (MH$^+$).

Example 15

5-(2-Butoxy-5-ethynyl-3-pyridinyl)-3-ethyl-2-(2-methoxyethyl)-2,6-dihydro-7H-pyrazolo[4,3-d]pyrimidin-7-one Potassium fluoride (22 mg, 0.38 mmol) was added to a stirred solution of the title compound from Example 14 (90 mg, 0.19 mmol) in aqueous N,N-dimethylformamide (2 mL N,N-dimethylformamide/0.2 mL water) at 0° C. After 10 min the reaction was allowed to warm to room temperature and stirred for 2 h. The reaction mixture was diluted with ethyl acetate and washed with water, 1 N hydrochloric acid (3 times) and brine. The organic layer was dried (MgSO$_4$) and concentrated to give the title compound as a white solid (75 mg).

$^1$H NMR (400 MHz, CDCl$_3$): δ=1.00 (t, 3H), 1.40 (t, 3H), 1.50 (m, 2H), 1.90 (m, 2H), 3.05 (q, 2H), 3.20 (s, 1H), 3.30 (s, 3H), 3.85 (t, 2H), 4.40 (t, 2H), 4.60 (t, 2H), 8.40 (s, 1H), 8.80 (s, 1H), 10.70 (s, 1H). LRMS (TSP): 396.3 (MH$^+$).

Example 16

5-(5-Acetyl-2-butoxy-3-pyridinyl)-3-ethyl-2-(2-methoxyethyl)-2,6-dihydro-7H-pyrazolo[4,3-d]pyrimidin-7-one The title compound of Example 15 (2.4 g, 6 mmol) and mercury sulfate (100 mg, 0.34 mmol) were stirred together in a mixture of 1N H$_2$SO$_4$ (5 mL) and acetone (35 mL). After 2 h a further portion of mercury sulfate (100 mg) was added and a third portion (100 mg in 5 mL 1N H$_2$SO$_4$) was added 2 h later. The crude reaction mixture was concentrated and the black residue partitioned between dichloromethane and water. The organic phase was separated and washed with saturated sodium bicarbonate solution and brine, dried (MgSO$_4$) and evaporated. Purification by flash column chromatography (gradient elution from 30% ethyl acetate: pentane to 100% ethyl acetate) gave 780 mg product.

$^1$H NMR (400 MHz, CDCl$_3$): δ=1.00 (t, 3H), 1.40 (t, 3H), 1.55 (m, 2H), 1.95 (m, 2H), 2.60 (s, 3H), 3.10 (q, 2H), 3.30 (s, 3H), 3.90 (t, 2H), 4.45 (t, 2H), 4.65 (t, 2H), 8.80 (s, 1H), 9.20 (s, 1H), 10.60 (s, 1H). LRMS (TSP): 414.3 (MH$^+$).

Example 17

5-[5-Acetyl-2-(2-methoxy-1-methylethoxy)-3-pyridinyl]-3-ethyl-2-(2-methoxyethyl)-2,6-dihydro-7H-pyrazolo[4,3-d]pyrimidin-7-one 5-(5-Acetyl-2-butoxy-3-pyridinyl)-3-ethyl-2-(2-methoxyethyl)-2,6-dihydro-7H-pyrazolo[4,3-d]pyrimidin-7-one (Example 16) (150 mg, 0.36 mmol) was dissolved in 1-methoxypropan-2-ol (3 mL) and the solution heated at reflux for 5 minutes to degas the solution. After cooling potassium hexamethyldisilazide (360 mg, 1.80 mmol) was added and the solution reheated to reflux for 8 h. The cooled reaction mixture was evaporated to dryness and partitioned between ethyl acetate and water after 1N hydrochloric acid had been used to adjust the pH to 8. The organic phase was separated and washed with brine, dried (MgSO$_4$) and evaporated. The crude product was purified by flash column chromatography (gradient elution from 100% dichloromethane 0.5% ammonia to 99% dichloromethane:1% methanol:0.5% ammonia) to give the title compound (45 mg, 29%).

$^1$H NMR (300 MHz, CDCl$_3$): δ=1.40 (t, 3H), 1.50 (d, 3H), 2.60 (s, 3H), 3.10 (q, 2H), 3.30 (s, 3H), 3.50 (s, 3H), 3.60–3.80 (m, 2H), 3.90 (t, 2H), 4.40 (t, 2H), 5.60 (m, 1H), 8.80 (s, 1H), 9.10 (s, 1H), 10.80 (s, 1H). LRMS (TSP): 430.3 (MH$^+$).

Example 18

5-{2-Butoxy-5-[3-(dimethylamino)propanoyl]-3-pyridinyl}-3-ethyl-2-(2-methoxyethyl)-2,6-dihydro-7H-pyrazolo[4,3-d]pyrimidin-7-one Dimethylamine hydrochloride (280 mg, 31 mmol) was added to formaldehyde (72 mg, 2 mL of a 37–41% aqueous solution) and the mixture sonicated until the white solid dissolved. After 30 min acetic anhydride (1.2 mL) was added and the mixture warmed in a water bath until a clear solution was obtained. A portion of this solution (0.16 mL) was added to 5-(5-acetyl-2-butoxy-3-pyridinyl)-3-ethyl-2-(2-methoxyethyl)-2,6-dihydro-7H-pyrazolo[4,3-d]pyrimidin-7-one (Example 16) (100 mg, 0.24 mmol) and the resulting solution heated in a water bath. After 1 h the reaction was cooled and extracted from saturated sodium bicarbonate solution with ethyl acetate. The organics were washed with a further portion of sodium bicarbonate solution then brine, dried (MgSO$_4$) and concentrated. The residue was purified by flash column chromatography (gradient elution from 100% dichloromethane to 10% methanol:dichloromethane) to give 50 mg product.

$^1$H NMR (400 MHz, CDCl$_3$): δ=1.00 (t, 3H), 1.40 (t, 3H), 1.50 (m, 2H), 1.95 (m, 2H), 2.35 (s, 6H), 2.80 (t, 2H), 3.10 (q, 2H), 3.20 (t, 2H), 3.30 (s, 3H), 3.90 (t, 2H), 4.45 (t, 2H), 4.65 (t, 2H), 8.80 (s, 1H), 9.25 (s, 1H), 10.60 (s, 1H). LRMS (TSP): 471.3 (MH$^+$).

Example 19

5-{2-Butoxy-5-[3-(4-ethyl-1-piperazinyl)propanoyl]-3-pyridinyl}-3-ethyl-2-(2-methoxyethyl)-2,6-dihydro-7H-pyrazolo[4,3-d]pyrimidin-7-one The title compound was prepared by the method of Example 18.

$^1$H NMR (400 MHz, CDCl$_3$): δ=1.00 (t, 3H), 1.10 (t, 3H), 1.40 (t, 3H), 1.55 (m, 2H), 1.95 (m, 2H), 2.40 (q, 2H), 2.40–2.70 (m, 8H), 2.85 (t, 2H), 3.10 (q, 2H), 3.20 (t, 2H), 3.30 (s, 3H), 3.90 (t, 2H), 4.40 (t, 2H), 4.70 (t, 2H), 8.80 (s, 1H), 9.20 (s, 1H), 10.60 (s, 1H). LRMS (TSP): 540.1 (MH$^+$).

Example 20

5-(2-Butoxy-5-iodo-3pyridinyl)-3-ethyl-1-(2-methoxyethyl)-1,6-dihydro-7H-pyrazolo[4,3-d]pyrimidin-7-one The title compound was made by the method of Example 1 using the title compound of Preparation 15.

$^1$H NMR (300 MHz, CDCl$_3$): δ=1.05 (t, 3H), 1.40 (t, 3H), 1.60 (m, 2H), 1.95 (m, 2H), 3.00 (q, 2H), 3.35 (s, 3H), 3.85 (t, 2H), 4.60 (t, 2H), 4.80 (t, 2H), 8.40 (s, 1H), 9.00 (s, 1H), 10.95 (s, 1H). LRMS (TSP): 497.8 (MH$^+$).

Example 20a (Preparative Example)

5-(2-Butoxy-5-trimethylsilylethynyl-3-pyridinyl)-3-ethyl-1-(2-methoxyethyl)-1,6-dihydro-7H-pyrazolo[4,3-d]pyrimidin-7-one The title compound was made by the method of Example 14 using the title compound of Example 20.

$^1$H NMR (300 MHz, CDCl$_3$): δ=0.25 (s, 9H), 1.00 (t, 3H), 1.40 (t, 3H), 1.60 (m, 2H), 1.90 (m, 2H), 3.00 (q, 2H), 3.35 (s, 3H), 3.85 (t, 2H), 4.60 (t, 2H), 4.80 (t, 2H), 8.40 (s, 1H), 8.80 (s, 1H), 11.00 (s, 1H). LRMS (TSP): 467.5 (MH$^+$).

Example 20b 5-(2-Butoxy-5-ethynyl-3-pyridinyl)-3-ethyl-1-(2-methoxyethyl)-1,6-dihydro-7H-pyrazolo[4,3-d]pyrimidin-7-one The title compound was made by the method of Example 15 using the title compound of Example 20a.

$^1$H NMR (300 MHz, CDCl$_3$): δ=1.00 (t, 3H), 1.40 (t, 3H), 1.55 (m, 2H), 1.90 (m, 2H), 3.00 (q, 2H), 3.20 (s, 1H), 3.35 (s, 3H), 3.80 (t, 2H), 4.60 (t, 2H), 4.80 (t, 2H), 8.40 (s, 1H), 8.85 (s, 1H), 11.00 (s, 1H). LRMS (TSP): 396.4 (MH$^+$).

Example 21

5-(5-Acetyl-2-butoxy-3-pyridinyl)-3-ethyl-1-(2-methoxyethyl)-1,6-dihydro-7H-pyrazolo[4,3-d]pyrimidin-7-one The title compound was made by the method of Example 16 using the title compound of Example 20.

$^1$H NMR (300 MHz, CDCl$_3$): δ=1.00 (t, 3H), 1.40 (t, 3H), 1.60 (m, 2H), 1.90 (m, 2H), 2.60 (s, 3H), 3.00 (q, 2H), 3.30 (s, 3H), 3.80 (t, 2H), 4.60 (t, 2H), 4.75 (t, 2H), 8.80 (s, 1H), 9.20 (s, 1H), 10.90 (s, 1H). LRMS (TSP): 413.9 (MH$^+$).

Example 22

5-(5-Iodo-2-isobutoxy-3-pyridinyl)-2-methyl-3-propyl-2,6-dihydro-7H-pyrazolo[4,3-d]pyrimidin-7-one The title compound was made by the method of Example 1 using the title compound of Preparation 14.

$^1$H NMR (300 MHz, CDCl$_3$): δ=1.05 (t, 3H), 1.10 (d, 6H), 1.80 (m, 2H), 2.25 (m, 1H), 3.00 (t, 2H), 4.05 (s, 3H), 4.30 (d, 2H), 8.40 (s, 1H), 9.00 (s, 1H), 10.70 (s, 1H). LRMS (TSP): 468.1 (MH$^+$).

Example 23

Methyl 6-Isobutoxy-5-(2-methyl-7-oxo-3-propyl-6,7-dihydro-2H-pyrazolo-[4,3-d]pyrimidin-5-yl)nicotinate The title compound was made by the method of Example 2 using the title compound of Example 22.

$^1$H NMR (300 MHz, CDCl$_3$): δ=1.05 (t, 3H), 1.15 (d, 6H), 1.80 (m, 2H), 2.30 (m, 1H), 3.00 (t, 2H), 4.00 (s, 3H), 4.10 (s, 3H), 4.40 (d, 2H), 8.80 (s, 1H), 9.30 (s, 1H), 10.65 (s, 1H). LRMS (TSP): 400.1 (MH$^+$).

Example 24

6-Isobutoxy-5-(2-methyl-7-oxo-3-propyl-6,7-dihydro-2H-pyrazolo[4,3-d]-pyrimidin-5-yl)nicotinic Acid The title compound was made by the method of Example 3 using the title compound of Example 23.

$^1$H NMR (300 MHz, CDCl$_3$): δ=1.05 (t, 3H), 1.10 (d, 6H), 1.80 (m, 2H), 2.25 (m, 1H), 3.05 (t, 2H), 4.10 (s, 3H), 4.40 (d, 2H), 8.95 (s, 1H), 9.20 (s, 1H), 11.10 (br s, 1H). LRMS (TSP): 386.1 (MH$^+$).

Example 25

5-[5-(4,4-Dimethyl-4,5-dihydro-1,3-oxazol-2-yl)-2-isobutoxy-3-pyridinyl]-2-methyl-3-propyl-2,6-dihydro-7H-pyrazolo[4,3-d]pyrimidin-7-one 6-Isobutoxy-5-(2-methyl-7-oxo-3-propyl-6,7-dihydro-2H-pyrazolo[4,3-d]pyrimidin-5-yl)nicotinic acid (Example 24) (200 mg, 0.52 mmol) was dissolved in dichloromethane and oxalyl chloride (0.18 mL, 2.8 mmol) was added followed by 1 drop of N,N-dimethylformamide. The mixture was stirred for 2 h and the solvent was then removed in vacuo, azeotroping with further dichloromethane. A dichloromethane solution of the acid chloride was then added to a solution of 2-amino-2-methyl-1-propanol (0.05 mL, 0.52 mmol) and diisopropylethylamine (0.09 mL, 0.62 mmol) in dichloromethane and the mixture stirred for 2 h. The reaction mixture was diluted with further dichloromethane and washed with a 1 N solution of citric acid, followed by brine. The organics were dried ($MgSO_4$) and concentrated in vacuo. The residue was redissolved in dichloromethane and thionyl chloride (0.05 mL, 0.62 mmol) was added. After 2 h the solution was washed with water then sodium bicarbonate solution. The organic phase was dried and concentrated. The crude residue was purified by flash column chromatography (50% ethyl acetate:pentane as eluant) to give the product.

$^1$H NMR (300 MHz, $CDCl_3$): δ=1.05 (d, 6H), 1.05 (t, 3H), 1.40 (s, 6H), 1.80 (m, 2H), 2.00 (m, 1H), 3.10 (t, 2H), 4.10 (s, 2H), 4.20 (d, 2H), 4.25 (s, 3H), 8.60 (s, 1H), 8.75 (s, 1H). LRMS (TSP): 439.0 ($MH^+$).

Example 26

6-Isobutoxy-N,N-dimethyl-5-(2-methyl-7-oxo-3-propyl-6,7-dihydro-2H-pyrazolo[4,3-d]pyrimidin-5-yl)nicotinamide The title compound was made by the method of Example 5 using the title compound of Example 24.

$^1$H NMR (300 MHz, $CDCl_3$): δ=1.00 (t, 3H), 1.10 (d, 6H), 1.80 (m, 2H), 2.30 (m, 1H), 2.95 (t, 2H), 3.20 (br.s, 6H), 4.00 (s, 3H), 4.40 (d, 2H), 8.40 (s, 1H), 8.90 (s, 1H), 10.75 (s, 1H). LRMS (TSP): 413.3 ($MH^+$).

Example 27

5-(5-Ethynyl-2-isobutoxy-3-pyridinyl)-2-methyl-3-propyl-2,6-dihydro-7H-pyrazolo[4,3-d]pyrimidin-7-one 5-(5-Iodo-2-isobutoxy-3-pyridinyl)-2-methyl-3-propyl-2,6-dihydro-7H-pyrazolo[4,3-d]pyrimidin-7-one (Example 22) (3 g, 6.42 mmol), trimethylsilylacetylene (4.5 mL, 32.1 mmol), copper(I) iodide (37 mg, 0.19 mmol), Pd $(PPh_3)_2Cl_2$ (13.5 mg, 0.19 mmol) were stirred together in a mixture of acetonitrile (50 mL) and triethylamine (50 mL) at 40° C. for 16 h under a nitrogen atmosphere. The solvent was evaporated and the crude mixture partitioned between 3% sodium bicarbonate solution and ethyl acetate. The organics were concentrated and redissolved in acetonitrile. Tetraethylammonium fluoride (1.27 g, 8.52 mmol) was added and the mixture stirred for 1.5 h at room temperature. A further portion of tetraethylammonium fluoride was added and the mixture stirred for a further 1.5 h. The organics were evaporated and the crude mixture partitioned between 3% sodium bicarbonate solution and ethyl acetate. The organics were dried ($MgSO_4$) and concentrated to give the product as a fawn solid (2.35 g).

$^1$H NMR (300 MHz, $CDCl_3$): δ=1.00 (t, 3H), 1.10 (d, 6H), 1.80 (m, 2H), 2.30 (m, 1H), 3.00 (t, 2H), 3.20 (s, 1H), 4.05 (s, 3H), 4.35 (d, 2H), 8.40 (s, 1H), 8.80 (s, 1H). TLC (1:1 ethyl acetate/pentane): $R_f$=0.25.

Example 28

5-[2-Isobutoxy-5-(1H-1,2,3-triazol-5-yl)-3-pyridinyl]-2-methyl-3-propyl-2,6-dihydro-7H-pyrazolo[4,3-d]pyrimidin-7-one 5-(5-Ethynyl-2-isobutoxy-3-pyridinyl)-2-methyl-3-propyl-2,6-dihydro-7H-pyrazolo[4,3-a]pyrimidin-7-one (Example 27) (200 mg, 0.54 mmol) and trimethylsilylazide (630 mg, 5.4 mmol) were stirred at 170° C. in a sealed pressure vessel for 14 h. The reaction mixture was cooled and partitioned between ethyl acetate and saturated sodium bicarbonate solution. The brown precipitate was filtered off and the 2 phases separated. The organic phase was washed with more sodium bicarbonate solution and brine, dried with ($MgSO_4$) and concentrated. This residue was combined with the original precipitate and purified by flash column chromatography (gradient elution from dichloromethane to 5% methanol:dichloromethane) to give 109 mg of a white solid (49%).

$^1$H NMR (400 MHz, $CDCl_3$): δ=0.90 (t, 3H), 1.00 (d, 6H), 1.75 (m, 2H), 2.20 (m, 1H), 2.90 (t, 2H), 4.00 (s, 3H), 4.30 (d, 2H), 7.80 (s, 1H), 8.60 (s, 1H), 9.00 (s, 1H), 10.80 (s, 1H). LRMS (ES): 409.0 ($MH^+$).

Example 29

5-(5-Glycoloyl-2-isobutoxy-3-pyridinyl)-2-methyl-3-propyl-2,6-dihydro-7H-pyrazolo[4,3-d]pyrimidin-7-one 5-(5-Ethynyl-2-isobutoxy-3-pyridinyl)-2-methyl-3-propyl-2,6-dihydro-7H-pyrazolo[4,3-d]pyrimidin-7-one (Example 27) (1 g, 2.7 mmol) and PhI($O_2CCF_3$)$_2$ (2.59 g, 6.02 mmol) were vigorously stirred in a mixture of dichloromethane:acetonitrile: $H_2O$ (45 mL of 80:10:1) under a nitrogen atmosphere. After 10 h the mixture was cooled, diluted with dichloromethane and washed with saturated sodium bicarbonate. The organic layer was dried ($MgSO_4$) and evaporated to give the crude product. Flash column chromatography (95% dichloromethane:methanol) gave 300 mg of pure product and a further 300 mg of slightly impure product.

$^1$H NMR (300 MHz, $CDCl_3$): δ=1.00 (t, 3H), 1.10 (d, 6H), 1.80 (m, 2H), 2.30 (m, 1H), 3,00 (t, 2H), 3.40 (t, 1H), 4.05 (s, 3H), 4.45 (d, 2H), 4.90 (d, 2H), 8.80 (s, 1H), 9.20 (s, 1H), 10.60 (s, 1H). TLC: Rf=0.3 (95% dichloromethane:5% MeOH).

Example 30

5-[5-(2-Chloroacetyl)-2-isobutoxy-3-pyridinyl]-2-methyl-3-propyl-2,6-dihydro-7H-pyrazolo[4,3-d]pyrimidin-7-one 5-(5-Glycoloyl-2-isobutoxy-3-pyridinyl)-2-methyl-3-propyl-2,6-dihydro-7H-pyrazolo[4,3-d]pyrimidin-7-one (Example 29) (0.3 g, 0.75 mmol), triethylamine (0.14 mL, 0.98 mmol) and methanesulfonyl chloride (0.07 mL, 0.9 mmol) were stirred in dichloromethane (7 mL) at room temperature for 24 h. The reaction mixture was diluted with ethyl acetate and washed with saturated sodium bicarbonate solution. The organics were dried ($MgSO_4$) and evaporated. The product was purified by flash column chromatography (eluting with 97% dichloromethane:3% methanol) to give 200 mg of product.

¹H NMR (300 MHz, CDCl₃): δ=1.00 (t, 3H), 1.15 (d, 6H), 1.80 (m, 2H), 2.30 (m, 1H), 3.00 (t, 2H), 4.10 (s, 3H), 4.45 (d, 2H), 4.65 (s, 2H), 8.85 (s, 1H), 9.25 (s, 1H), 10.60 (s, 1H). TLC: R$_f$=0.3 (97% dichloromethane:3% MeOH).

Example 31

5-{2-Isobutoxy-5-[2-(4-morpholinyl)acetyl]-3-pyridinyl}-2-methyl-3-propyl-2,6-dihydro-7H-pyrazolo[4,3-d]pyrimidin-7-one 5-[5-(2-Chloroacetyl)-2-isobutoxy-3-pyridinyl]-2-methyl-3-propyl-2,6-dihydro-7H-pyrazolo[4,3-d]pyrimidin-7-one (Example 30) (100 mg, 0.24 mmol), triethylamine (0.04 mL, 0.29 mmol) and morpholine (0.023 mL, 0.26 mmol) were stirred in dichloromethane (3 mL) under a nitrogen atmosphere for 16 h. The mixture was poured into ethyl acetate and washed with saturated sodium bicarbonate solution. The organics were dried (MgSO₄) and concentrated. The product was purified by flash column chromatography (eluting with 97% dichloromethane:3% methanol) to give 80 mg of product as a beige foam.

¹H NMR (300 MHz, CDCl₃): δ=1.00 (t, 3H), 1.15 (d, 6H), 1.80 (m, 2H), 2.30 (m, 1H), 2.60 (m, 4H), 3.00 (t, 2H), 3.80 (m, 6H), 4.05 (s, 3H), 4.40 (d, 2H), 9.00 (s, 1H), 9.40 (s, 1H), 10.60 (s, 1H). TLC: R$_f$=0.3 (97% dichloromethane:3% MeOH)

Example 32

5-{5-[2-(4-Ethyl-1-piperazinyl)acetyl]-2-isobutoxy-3-pyridinyl}-2-methyl-3-propyl-2,6-dihydro-7H-pyrazolo[4,3-d]pyrimidin-7-one The title compound was prepared as for Example 31.

¹H NMR (300 MHz, CDCl₃): δ=1.05 (t, 3H), 1.10 (d, 6H), 1.10 (t, 3H), 1.80 (m, 2H), 2.25 (m, 1H), 2.40 (q, 2H), 2.40–2.70 (m, 8H), 3.00 (t, 2H), 3.75 (s, 2H), 4.10 (s, 3H), 4.40 (d, 2H), 9.00 (s, 1H), 9.35 (s, 1H), 10.60 (s, 1H). TLC: R$_f$=0.5 (89% dichloromethane:10% methanol:1% ammonia).

Example 33

5-(2-Butoxy-5-glycoloyl-3-pyridinyl)-3-ethyl-2-(2-methoxyethyl)-2,6-dihydro-7H-pyrazolo[4,3-d]pyrimidin-7-one The title compound was made by the method of Example 29 using Example 15.

¹H NMR (400 MHz, CDCl₃): δ=1.00 (t, 3H), 1.40 (t, 3H), 1.55 (m, 2H), 1.95 (m, 1H), 3.10 (q, 2H), 3.30 (s, 3H), 3.40 (t, 1H), 3.90 (t, 2H), 4.40 (t, 2H), 4.65 (t, 2H), 4.90 (d, 2H), 8.80 (s, 1H), 9.20 (s, 1H), 10.60 (s, 1H). LRMS (TSP): 430.4 (MH⁺).

Example 34

5-[2-Butoxy-5-(4-morpholinylacetyl)-3-pyridinyl]-3-ethyl-2-(2-methoxyethyl)-2,6-dihydro-7H-pyrazolo[4,3-d]pyrimidin-7-one Triphenylphosphine (110 mg, 0.42 mmol) in dichloromethane (1 mL) was added slowly to an ice cooled solution of 5-(2-butoxy-5-glycoloyl-3-pyridinyl)-3-ethyl-2-(2-methoxyethyl)-2,6-dihydro-7H-pyrazolo[4,3-d]pyrimidin-7-one (Example 33) (150 mg, 0.35 mmol) and carbon tetrabromide (140 mg, 0.42 mmol) in dichloromethane (3 mL). The solution was allowed to warm to room temperature. After 2 h further carbon tetrabromide (25 mg, 0.075 mmol) and triphenylphosphine were added and stirring continued for 2 h. Concentration and purification of the product by flash column chromatography (gradient elution with ethyl acetate/pentane (10:90–70:30) gave 5-[2-butoxy-5-(2-bromoacetyl)-3-pyridinyl]-3-ethyl-2-(2-methoxyethyl)-2,6-dihydro-7H-pyrazolo[4,3-d]-pyrimidin-7-one which was used without any further purification (slight contamination with triphenylphosphine oxide). 5-[2-Butoxy-5-(2-bromoacetyl)-3-pyridinyl]-3-ethyl-2-(2-methoxyethyl)-2,6-dihydro-7H-pyrazolo[4,3-d]pyrimidin-7-one (205 mg, 0.42 mmol) was dissolved in dichloromethane and the solution cooled to 0° C. Morpholine (54 mg, 0.62 mmol) and triethylamine (84 mg, 0.83 mmol) were added and the mixture was allowed to warm to room temperature and stirred for 2 h. The solvent was evaporated and the residue dissolved in ethyl acetate, washed with water (twice), saturated sodium bicarbonate (twice) and brine, dried (MgSO₄) and concentrated. Purification by flash column chromatography (gradient elution 20% ethyl acetate/pentane:100% ethyl acetate:3% methanol/methyl acetate) gave 70 mg product.

¹H NMR (300 MHz, CDCl₃): δ=1.00 (t, 3H), 1.40 (t, 3H), 1.60 (m, 2H), 1.95 (m, 2H), 2.60 (m, 4H), 3.05 (q, 2H), 3.25 (s, 3H), 3.75 (m, 6H), 3.90 (t, 2H), 4.45 (t, 2H), 4.65 (t, 2H), 9.00 (s, 1H), 9.40 (s, 1H), 10.60 (s, 1H). LRMS (ES): 499.1 (MH⁺).

Example 35

6-Butoxy-5-[3-ethyl-2-(2-methoxyethyl)-7-oxo-6,7-dihydro-2H-pyrazolo[4,3]pyrimidin-5-yl] nicotinonitrile Copper(I) cyanide (35 mg, 0.39 mmol) was mixed with the title compound of Example 1 (130 mg, 0.26 mmol) in N-methylpyrrolidinone (3 mL) and the resulting solution was heated for 14 h at 150° C. under a nitrogen atmosphere. The reaction mixture was cooled and partitioned between ethyl acetate and water. Concentrated ammonium hydroxide was added and the organic layer was separated, washed with more ammonia solution and brine, dried (MgSO₄), filtered and evaporated to give a brown solid.

¹H NMR (400 MHz, CDCl₃): δ=1.00 (t, 3H), 1.40 (t, 3H), 1.50 (m, 2H), 1.90 (m, 2H), 3.10 (q, 2H), 3.30 (s, 3H), 3.90 (t, 2H), 4.40 (t, 2H), 4.65 (t, 2H), 8.55 (s, 1H), 9.00 (s, 1H), 10.60 (s, 1H). LRMS (TSP): 397.2 (MH⁺).

Example 36

6-Isobutoxy-5-(2-methyl-7-oxo-3-propyl-6,7-dihydro-2H-pyrazolo[4,3-d]-pyrimidin-5-yl) nicotinonitrile The title compound was prepared by the method of Example 35.

¹H NMR (400 MHz, CDCl₃): δ=1.05 (t, 3H), 1.10 (d, 6H), 1.80 (m, 2H), 2.30 (m, 1H), 3.00 (t, 2H), 4.10 (s, 3H), 4.40 (d, 2H), 8.60 (s, 1H), 9.00 (s, 1H), 10.60 (s, 1H). LRMS (TSP): 367.0 (MH⁺).

Example 37 (Preparative Example)

6-Isobutoxy-5-(2-methyl-7-oxo-3-propyl-6,7-dihydro-2H-pyrazolo[4,3-d]pyrimidin-5-yl)-3-pyridinecarbothioamide Water (2 drops) was added to a stirred suspension of 6-isobutoxy-5-(2-methyl-7-oxo-3-propyl-6,7-dihydro-2H-pyrazolo[4,3-d]pyrimidin-5-yl)-nicotinonitrile (Example 36) (150 mg, 0.41 mmol) in $(EtO)_2P(S)SH$ (0.5 mL). The mixture was stirred at room temperature. After 5 h more $(EtO)_2P(S)SH$ (0.5 mL) was added and dichloromethane (5 mL) added to aid stirring. After 14 h the reaction mixture was diluted with dichloromethane and washed with saturated sodium bicarbonate solution. After filtration and separation of the phases the organics were washed again with saturated sodium bicarbonate solution and brine, dried $(MgSO_4)$ and concentrated. The product was purified by flash column chromatography (gradient elution from 100% dichloromethane to 96% dichloromethane:methanol) to give 80 mg product.

$^1$H NMR (400 MHz, $CDCl_3$): δ=0.90 (t, 3H), 0.95 (d, 6H), 1.70 (m, 2H), 2.10 (m, 1H), 2.80 (t, 2H), 3.90 (s, 3H), 4.20 (d, 2H), 8.60 (br s, 1H), 8.70 (s, 1H), 8.75 (br s, 1H), 9.00 (s, 1H), 10.65 (s, 1H). LRMS (TSP): 366.9 ($MH^+$).

Example 38

5-[2-Isobutoxy-5-(4-methyl-1,3-thiazol-2-yl)-3-pyridinyl]-2-methyl-3-propyl-2,6-dihydro-7H-pyrazolo[4,3-d]pyrimidin-7-one 6-Isobutoxy-5-(2-methyl-7-oxo-3-propyl-6,7-dihydro-2H-pyrazolo[4,3-d]-pyrimidin-5-yl)-3-pyridinecarbothioamide (Example 37) (77 mg, 0.19 mmol) and chloroacetone (36 mg, 0.38 mmol) were heated to reflux for 14 h in ethanol (5 mL). The reaction mixture was cooled and concentrated. Purification by flash column chromatography (gradient elution from 100% dichloromethane to 3% methanol:dichloromethane) gave 65 mg of product.

$^1$H NMR (400 MHz, $CDCl_3$): δ=1.00 (t, 3H), 1.10 (d, 6H), 1.85 (m, 2H), 2.30 (m, 1H), 2,55 (s, 3H), 3.00 (t, 2H), 4.10 (s, 3H), 4.40 (d, 2H), 6.90 (s, 1H), 8.80 (s, 1H), 9.20 (s, 1H), 10.75 (s, 1H). LRMS (TSP): 438.9 ($MH^+$).

Example 39 (Preparative Example)

H'-Hydroxy-6-isobutoxy-5-(2-methyl-7-oxo-3-propyl-6,7-dihydro-2H-pyrazolo[4,3-d]pyrimidin-5-yl)-3-pyridinecarboximidamide Potassium t-butoxide (61 mg, 0.54 mmol) was added to a stirred suspension of hydroxylamine hydrochloride (38 mg, 0.54 mmol) in 2-methyl-1-propanol (5 mL). After 2–3 min 6-isobutoxy-5-(2-methyl-7-oxo-3-propyl-6,7-dihydro-2H-pyrazolo[4,3-d]pyrimidin-5-yl)nicotinonitrile (Example 36) (200 mg, 0.54 mmol) was added and the reaction mixture heated at reflux for 5 h. A further 1 equivalent of potassium t-butoxide and hydroxylamine hydrochloride were added and refluxing continued for 14 h. The reaction mixture was cooled and concentrated. The residue was triturated with dichloromethane and filtered, washing the solid with further dichloromethane. The filtrate was evaporated and purified by flash column chromatography (elution with ethyl acetate +2% ammonia) gave 65 mg of the title compound as a white solid.

$^1$H NMR (300 MHz, $CDCl_3$): δ=0.80 (t, 3H), 0.95 (d, 6H), 1.60 (m, 2H), 2.10 (m, 1H), 2.80 (t, 2H), 3.90 (s, 3H), 4.20 (d, 2H) 5.00 (br s, 2H), 8.40 (s, 1H), 8.70 (s, 1H), 9.35 (s, 1H)., 10.70 (s, 1H). LRMS (TSP): 399.8 $MH^+$).

Example 40 (Preparative Example)

5-{5-[[(Acetyloxy)imino](amino)methyl]-2-isobutoxy-3-pyridinyl}-2-methyl-3-propyl-2,6-dihydro-7H-pyrazolo[4,3-d]pyrimidin-7-one N-Hydroxy-6-isobutoxy-5-(2-methyl-7-oxo-3-propyl-6,7-dihydro-2H-pyrazolo[4,3-d]pyrimidin-5-yl)-3-pyridinecarboximidamide (Example 39) (65 mg, 0.16 mmol), N,N-dimethylaminopyridine (24 mg, 0.20 mmol), acetic acid (9.7 mg, 0.16 mmol) and 1-(3-dimethylaminopropyl)-3-ethyl-carbodiimide hydrochloride (37.5 mg, 0.20 mmol) were stirred in dioxan (2 mL) for 14 h. The solvent was removed in vacuo and the product purified by flash column chromatography (eluting with 90% dichloromethane:methanol) to give the product (58 mg) as a white solid.

$^1$H NMR (300 MHz, $CDCl_3$): δ=1.00 (t, 3H), 1.10 (d, 6H), 1.80 (m, 2H), 2.30 (s, 3H), 2.25 (m, 1H), 2.95 (t, 2H), 4.00 (s, 3H), 4.40 (d, 2H), 5.25 (br s, 2H), 8.60 (s, 1H), 8.75 (s, 1H), 10.70 (s, 1H). LRMS (EI): 442.1 ($MH^+$).

Example 41

5-[2-Isobutoxy-5-(5-methyl-1,2,4-oxadiazol-3-yl)-3-pyridinyl]-2-methyl-3-propyl-2,6-dihydro-7H-pyrazolo[4,3-d]pyrimidin-7-one 5-{5-[[(Acetyloxy)imino](amino)methyl]-2-isobutoxy-3-pyridinyl}-2-methyl-3-propyl-2,6-dihydro-7H-pyrazolo[4,3-d]pyrimidin-7-one (Example 40) (55 mg, 0.13 mmol) was heated at 190° C. for 3 h. After cooling the oxadiazole was purified by flash column chromatography (elution with 50:1 dichloromethane:methanol) to give 21 mg of a yellow solid.

$^1$H NMR (300 MHz, $CDCl_3$): δ=1.05 (t, 3H), 1.10 (d, 6H), 1.80 (m, 2H), 2.30 (m, 1H), 2.70 (s, 3H), 3.00 (t, 2H), 4.05 (s, 3H), 4.40 (d, 2H), 8.95 (s, 1H), 9.35 (s, 1H), 10.70 (s, 1H). LRMS (ES): 424.1 ($MH^+$).

Example 42

5-[2-Isobutoxy-5-(3-methyl-1,2,4-oxadiazol-5-yl)-3-pyridinyl]-2-methyl-3-propyl-2,6-dihydro-7H-pyrazolo[4,3-d]pyrimidin-7-one 5-(5-Iodo-2-isobutoxy-3-pyridinyl)-2-methyl-3-propyl-2,6-dihydro-7H-pyrazolo[4,3-d]pyrimidin-7-one (Example 22) (200 mg, 0.42 mmol) and N'-hydroxyethanimidamide (EP 795 328) (95 mg, 1.28 mmol) were suspended in toluene (4 mL) and triethylamine (86 mg, 0.85 mmol) was added. $Pd(PPh_3)_2Cl_2$ (15 mg, 0.02 mmol) was added and placed in a preheated oil bath at 95° C. under 1 atmosphere carbon monoxide. After 4 h a further portion of acetamidoxime (50 mg), triethylamine (43 mg) and $Pd(PPh_3)_2Cl_2$ (15 mg) were added and stirring was continued at 95° C. for 14 h. The cooled reaction mixture was diluted with ethyl acetate and washed with water and brine, dried $(MgSO_4)$, filtered and evaporated. Purification by flash column chromatography (gradient elution from dichloromethane:1% methanol:dichloromethane) gave 70 mg product.

$^1$H NMR (300 MHz, $CDCl_3$): δ=1.00 (t, 3H), 1.10 (d, 6H), 1.80 (m, 2H), 2.30 (m, 1H), 2.50 (s, 3H), 3.00 (t, 2H), 4.10 (s, 3H), 4.45 (d, 2H), 9.00 (s, 1H), 9.40 (s, 1H), 10.70 (s, 1H). LRMS (TSP): 424.1 ($MH^+$).

Example 43

5-[2-Isobutoxy-5-(1H-1,2,3,4-tetrazol-5-yl)-3-pyridinyl]-2-methyl-3-propyl-2,6-dihydro-7H-pyrazolo[4,3-d]pyrimidin-7-one 5-[2-Isobutoxy-5-cyano-3-pyridinyl]-2-methyl-3-propyl-2,6-dihydro-7H-pyrazolo[4,3-a]pyrimidin-7-one (Example 36) (200 mg, 0.55 mmol), trimethylsilylazide (0.069 mL, 0.54 mmol) and dibutyltin oxide (54 mg, 0.22 mmol) were heated at 80° C. in toluene (10 mL) for 14 h. The reaction mixture was transferred to a PTFE lined sealed vessel, a further 0.069 mL trimethylsilylazide added and the reaction heated at 80° C. for a further 5 h. After cooling and filtering the filtrate was diluted with pentane. Further solid precipitated and this was combined with the original precipitate and purified by flash column chromatography (eluting with dichloromethane/methanol/ammonia in a ratio of 5:1:0.1) to give 144 mg product.

$^1$H NMR (300 MHz, CD$_3$OD): δ=1.00 (t, 3H), 1.10 (d, 6H), 1.80 (m, 2H), 2.20 (m, 1H), 3.10 (t, 2H), 4.10 (s, 3H), 4.35 (d, 2H), 8.90 (s, 1H), 8.95 (s, 1H). LRMS (ES): 410.1 (MH$^+$).

Example 44

5-(2-Butoxy-5-iodo-3-pyridinyl)-2-[2-(dimethylamino)ethyl]-3-ethyl-2,6-dihydro-7H-pyrazolo[4,3-d]pyrimidin-7-one The title compound was made by the method of Example 1 from Preparation 17.

$^1$H NMR (300 MHz, CDCl$_3$): δ=0.95 (t, 3H), 1.40 (t, 3H), 1.55 (m, 2H), 1.85 (m, 2H), 2.30 (s, 3H), 2.80 (t, 2H), 3.00 (q, 2H), 4.40 (t, 2H), 4.60 (t, 2H), 8.40 (s, 1H), 8.95 (s, 1H), 10.70 (s, 1H). LRMS (TSP): 511.3 (MH$^+$).

Examples 44a to 44c

The following compounds were made by the method of Example 44

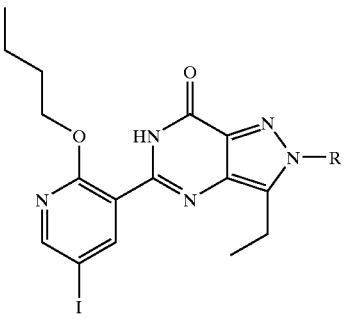

from the appropriate pyrazolocarboxamides.

| Ex. | R | LRMS (MH$^+$) | $^1$H NMR |
|---|---|---|---|
| 44a | morpholinoethyl | 553 | (400 MHz, CDCl$_3$): δ = 1.00(t, 3H), 1.40(t, 3H), 1.55(m, 2H), 1.90(m, 2H), 2.50(m, 4H), 2.95(t, 2H), 3.05 (q, 2H), 3.65(m, 4H), 4.40(t, 2H), 4.50(t, 2H), 8.40(s, 1H), 9.00(s, 1H), 10.70(s, 1H). |
| 44b | N-Boc-piperidinyl | 623 | (400 MHz, CDCl$_3$): δ = 1.00(t, 3H), 1.40(t, 3H), 1.50(s, 9H), 1.55(m, 2H), 1.90(m, 4H), 2.40(br s, 2H), 2.90(br s, 2H), 3.10(q, 2H), 4.30(m, 3H), 4.60(t, 2H), 8.40(s, 1H), 9.00 (s, 1H), 10.70(s, 1H). |
| 44c | N-Boc-azetidinyl | 612.2 | (400 MHz, CDCl$_3$): δ = 1.00(t, 3H), 1.40(t, 3H), 1.50(s, 9H), 1.55(m, 2H), 1.90(m, 2H), 3.00(q, 2H), 4.40 (t, 2H), 4.50(t, 2H), 4.65(br s, 2H), 5.20(m, 1H), 8.40(s, 1H), 9.00(s, 1H), 10.80(s, 1H). |

Example 45 (Preparative Example)

5-(2-Butoxy-5-trimethylsilylethynyl-3-pyridinyl)-2-[2-(dimethylamino)-ethyl]-3-ethyl-2,6-dihydro-7H-pyrazolo[4,3-d]pyrimidin-7-one Pd(PPh$_3$)$_2$Cl$_2$ (11.2 mg, 0.016 mmol) and cuprous iodide (3 mg, 0.016 mmol) were added to a stirred slurry of 5-(2-butoxy-5-iodo-3-pyridinyl)-2-[2-(dimethylamino)ethyl]-3-ethyl-2,6-dihydro-7H-pyrazolo[4,3-d]pyrimidin-7-one (Example 44) (330 mg, 0.647 mmol) in triethylamine (8 mL) and acetonitrile (2 mL) at room temperature under a nitrogen atmosphere. The mixture was heated at 60° C. for 3 h, cooled and extracted from brine with dichioromethane (2×100 mL). The organics were dried (MgSO$_4$) and concentrated to give a yellow solid. Purification by flash column chromatography (elution with 5% methanol/95% dichloromethane) gave the product as a pale brown oil (290 mg, 93%).

$^1$H NMR (300 MHz, CDCl$_3$): δ=0.30 (s, 9H), 1.00 (t, 3H), 1.40 (t, 3H), 1.50 (m, 2H), 1.90 (m, 2H), 2.30 (s, 3H), 2.90 (t, 2H), 3.05 (q, 2H), 4.40 (t, 2H), 4.60 (t, 2H), 8.30 (s, 1H), 8.80 (s, 1H), 10.70 (s, 1H). LRMS (TSP): 481.3 (MH$^+$).

Examples 45a to 45c

The following compounds were made by the method of Example 45:

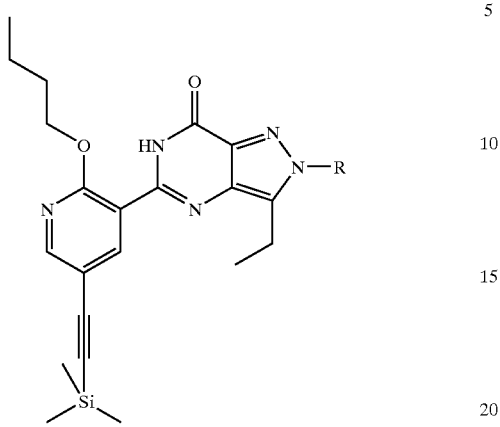

from the appropriate iodo compounds.

Examples 46a to 46c

The following compounds were made by the method of Example 46

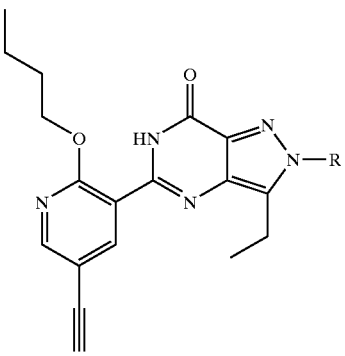

from the appropriate trimethylsilyl compounds.

| Ex. | R | LRMS | $^1$H NMR |
|---|---|---|---|
| 45a | *–CH$_2$CH$_2$–morpholinyl | 523 MH$^+$ | (300 MHz, CDCl$_3$): δ = 0.25(s, 9H), 1.00 (t, 3H), 1.40(t, 3H), 1.50(m, 2H), 1.90(m, 2H), 2.50(m, 4H), 2.95(t, 2H), 3.05(q, 2H), 3.70(m, 4H), 4.40(t, 2H), 4.60(t, 2H), 8.40(s, 1H), 8.80(s, 1H), 10.70(s, 1H). |
| 45b | *–(piperidin-4-yl)-N-Boc | 615 - MNa$^+$ | (400 MHz, CDCl$_3$): δ = 0.25(s, 9H), 1.00 (t, 3H), 1.40(t, 3H), 1.50(s, 9H), 1.55(m, 2H), 1.90(m, 4H), 2.40(br s, 2H), 2.85(br s, 2H), 3.10(m, 2H), 4.40(m, 3H), 4.60(t, 2H), 8.35(s, 1H), 8.80(s, 1H), 10.70(s, 1H). |
| 45c | *–(azetidin-3-yl)-N-Boc | 582.4 - MH$^+$ | (400 MHz, CDCl$_3$): δ = 0.25(s, 9H), 1.00 (t, 3H), 1.40(t, 3H), 1.40(s, 9H), 1.50(m, 2H), 1.90(m, 2H), 3.00(q, 2H), 4.40(t, 2H), 4.50(t, 2H), 4.60(br s, 2H), 5.25(m, 1H), 8.40(s, 1H), 8.80(s, 1H), 10.80(s, 1H). |

Example 46

5-(2-Butoxy-5-ethynyl-3-pyridinyl)-2-[2-(dimethylamino)ethyl]-3-ethyl-2,6-dihydro-7H-pyrazolo[4,3-d]pyrimidin-7-one Potassium fluoride (72.5 mg, 1.25 mmol) was added to a stirred solution of 5-(2-butoxy-5-trimethylsilylethynyl-3-pyridinyl)-2-[2-(dimethylamino)-ethyl]-3-ethyl-2,6-dihydro-7H-pyrazolo[4,3-d]pyrimidin-7-one (Example 45) (300 mg, 0.625 mmol) in N,N-dimethylformamide (10 mL) and water (2 mL) at room temperature. After 2 h the reaction mixture was poured into brine and extracted with ethyl acetate (2×100 mL) The organics were dried (MgSO$_4$) and concentrated to give the product (285 mg) as a pale brown oil.

$^1$H NMR (300 MHz, CDCl$_3$): δ=1.00 (t, 3H), 1.40 (t, 3H), 1.50 (m, 2H), 1.90 (m, 2H), 2.30 (s, 6H), 2.90 (t, 2H), 3.00 (q, 2H), 4.40 (t, 2H), 4.60 (t, 2H), 8.40 (s, 1H), 8.80 (s, 1H), 10.70 (s, 1H). LRMS (ES): 409 (MH$^+$).

| Ex. | R | LRMS (MH⁺) | ¹H NMR |
|---|---|---|---|
| 46a | *‑CH₂CH₂‑N(morpholine) | 451 | (400 MHz, CDCl₃): δ = 1.00(t, 3H), 1.40 (t, 3H), 1.50(m, 2H), 1.90(m, 2H), 2.50 (m, 4H), 2.95(t, 2H), 3.05(q, 2H), 3.20 (s, 1H), 3.70(m, 4H), 4.40(t, 2H), 4.60 (t, 2H), 8.40(s, 1H), 8.80(s, 1H), 10.75 (s, 1H). |
| 46b | *‑CH₂‑(N-Boc-piperidine) | 521 | (400 MHz, CDCl₃): δ = 1.00(t, 3H), 1.40 (t, 3H), 1.50(m, 2H), 1.50(s, 9H), 1.90 (m, 4H), 2.40(br s, 2H), 2.90(br s, 2H), 3.05(q, 2H), 3.20(s, 1H), 4.40(m, 3H), 4.60(t, 2H), 8.40(s, 1H), 8.80(s, 1H), 10.70(s, 1H). |
| 46c | *‑(N-Boc-azetidin-3-yl) | 393.3 | (400 MHz, CDCl₃): δ = 1.00(t, 3H), 1.35 (t, 3H), 1.50(s, 9H), 1.55(m, 2H), 1.90 (m, 2H), 3.00(q, 2H), 3.20(s, 1H), 4.35 (t, 2H), 4.60(t, 2H), 4.65(br s, 2H), 5.20(m, 1H), 8.40(s, 1H), 8.80(s, 1H), 10.80(s, 1H). |

Example 47

5-(5-Acetyl-2-butoxy-3-pridinyl)-2-[2-(dimethylamino)ethyl]-3-ethyl-2,6-dihydro-7H-pyrazolo[4,3-d]pyrimidin-7-one 1 N Sulfuric acid (1 mL) was added to a stirred solution of 5-(2-butoxy-5-ethynyl-3-pyridinyl)-2-[2-(dimethylamino)ethyl]-3-ethyl-2,6-dihydro-7H-pyrazolo[4,3-d]pyrimidin-7-one (Example 46) (280 mg, 0.69 mmol) in acetone (8 mL) at room temperature. Mercury sulfate (40 mg, 0.14 mmol) was added and the mixture heated at reflux for 5 h. The reaction mixture was cooled, diluted with methanol (10 mL), filtered and the filtrate washed with further methanol. The solvent was evaporated and the residue partitioned between ethyl acetate (100 mL) and saturated sodium bicarbonate solution (100 mL). The aqueous was washed with a further 100 mL of ethyl acetate and the combined organics dried (MgSO₄) and concentrated. Purification by flash column chromatography (elution with 95% dichloromethane/methanol) gave the product as a cream coloured solid (140 mg).

¹H NMR (300 MHz, CDCl₃): δ=1.00 (t, 3H), 1.40 (t, 3H), 1.50 (m, 2H), 1.90 (m, 2H), 2.60 (s, 3H), 2.90 (t, 2H), 3.05 (q, 2H), 4.40 (t, 2H), 4.70 (t, 2H), 8.80 (s, 1H), 9.20 (s, 1H), 10.60 (s, 1H). LRMS (TSP): 427.5 (MH⁺).

Examples 47a to 47c

The following compounds were made by the method of Example 47

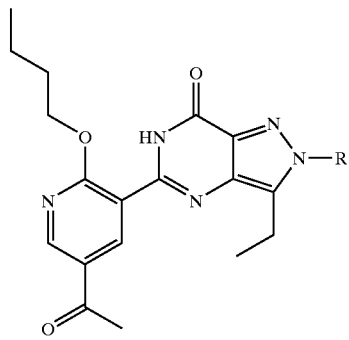

from the appropriate acetylene compounds.

| Ex. | R | LRMS (MH⁺) | ¹H NMR |
|---|---|---|---|
| 48 | *‑CH₂CH₂‑N(morpholine) | 469 | (400 MHz, CDCl₃): δ = 1.00(t, 3H), 1.40 (t, 3H), 1.50(m, 2H), 1.90(m, 2H), 2.50 (m, 4H), 2.65(s, 3H), 2.95(t, 2H), 3.10 (q, 2H), 3.65(m, 4H), 4.40(t, 2H), 4.65 (t, 2H), 8.80(s, 1H), 9.20(s, 1H), 10.60 (s, 1H). |
| 49* | *‑(piperidin-4-yl)NH | 440 | (400 MHz, CDCl₃): δ = 1.00(t, 3H), 1.40 (t, 3H), 1.50(m, 4H), 1.90(m, 4H), 2.35 (m, 2H), 2.60(s, 3H), 2.80(t, 2H), 3.10 (q, 2H), 3.30(d, 2H), 4.40(m, 1H), 4.45 (t, 2H), 8.80(s, 1H), 9.20(s, 1H), 10.60 (br s, 1H). |

-continued

| Ex. | R | LRMS (MH+) | ¹H NMR |
|---|---|---|---|
| 50* | [piperidine with N-C(=O)-O-tBu substituent] | 539.5 | (300 MHz, CDCl₃): δ = 1.00(t, 3H), 1.40 (t, 3H), 1.45(s, 9H), 1.50(m, 2H), 1.90 (m, 4H), 2.40(m, 2H), 2.65(s, 3H), 2.90(m, 2H), 3.10(q, 2H), 4.30(br s, 3H), 4.65(m, 2H), 8.80(s, 1H), 9.20(s, 1H), 10.60(s, 1H). |
| 50a** | [azetidine with N-H] | 411.6 | (300 MHz, CDCl₃): δ = 1.00(t, 3H), 1.35 (t, 3H), 1.50(m, 2H), 1.95(m, 2H), 2.60 (s, 3H), 3.00(q, 2H), 3.90(t, 2H), 4.55 (t, 2H), 4.70(t, 2H), 5.40(m, 1H), 8.80 (s, 1H), 9.20(s, 1H), 10.65(br s, 1H). |

*The acid mediated hydrolysis of the acetylene to the acetyl (as in Example 47) resulted in the formation of both the title compounds of Example 49 and Example 50 through hydrolysis of the tert-butylcarbamate functionality under the reaction conditions.
**The acid mediated hydrolysis of the acetylene to the acetyl (as in Example 47) was left for an extended period of time to facilitate complete hydrolysis of the tert-butylcarbamate functionality under the reaction conditions.

Example 51

5-(5-Acetyl-2-butoxy-3-pyridinyl)-3-ethyl-2-(1-methyl-4-piperidinyl)-2,6-dihydro-7H-pyrazolo[4,3-d]pyrimidin-7-one 5-(5-Acetyl-2-butoxy-3-pyridinyl)-3-ethyl-2-(4-piperidinyl)-2,6-dihydro-7H-pyrazolo[4,3-d]pyrimidin-7-one (Example 49) (100 mg, 0.23 mmol) was dissolved in dichloromethane (10 mL) and formaldehyde (27 mg, 0.01 mL of a 37–41% solution) was added. After 30 min stirring sodium triacetoxyborohydride (108 mg, 0.51 mmol) was added and stirring continued for 14 h. Further formaldehyde (0.01 mL of 37–41% solution) and sodium triacetoxyborohydride (108 mg, 0.51 mmol) were added and stirring continued for a further 4.5 h. Starting material still remained so further formaldehyde (0.01 mL of 37–41% solution) and sodium triacetoxyborohydride (108 mg, 0.51 mmol) were added and stirring continued for a further 18 h. The reaction mixture was diluted with dichloromethane, washed with sodium bicarbonate solution then brine, dried (MgSO₄) and concentrated. Purification by flash column chromatography (elution with 94:6:0.6 dichloromethane/methanol/0.88 ammonia) gave the product (41 mg) as a white solid.

¹H NMR (400 MHz, CDCl₃): δ=1.00 (t, 3H), 1.40 (t, 3H), 1.55 (m, 2H), 1.90 (m, 4H), 2.15 (t, 2H), 2.35 (s, 3H), 2.55 (m, 2H), 2.65 (s, 3H), 3.00 (m, 4H), 4.20 (m, 1H), 4.65 (t, 2H), 8.80 (s, 1H), 9.20 (s, 1H), 10.50 (s, 1H). LRMS (TSP): 453.4 (MH⁺).

Example 51a 5-(5-Acetyl-2-butoxy-3-pyridinyl)-3-ethyl-2-(1-methyl-3-azetidinyl)-2,6-dihydro-7H-pyrazolo[4,3-d]pyrimidin-7-one The title compound was made by the method of Example 51 using Example 50a as starting material.

¹H NMR (400 MHz, CDCl₃): δ=1.00 (t, 3H), 1.40 (t, 3H), 1.55 (m, 2H), 1.95 (m, 2H), 2.50 (s, 3H), 2.60 (s, 3H), 3.00 (q, 2H), 3.80 (t, 2H), 3.90 (t, 2H), 4.65 (t, 2H), 5.10 (m, 1H), 8.80 (s, 1H), 9.20 (s, 1H), 10.65 (s, 1H). LRMS (TSP): 425.6 (MH⁺).

Example 52

5-(2-Ethoxy-5-nitropyridin-3-yl)-2-methyl-2,6-dihydro-7H-pyrazolo[4,3-d]pyrimidin-7-one A mixture of the title compounds of Preparations 29 (3.85 g, 27.5 mmol) and 26 (8.26 g, 30.6 mmol) in 3-methyl-3-pentanol (80 mL) was heated under reflux for 2½ h, then cooled. The reaction mixture was partitioned between dichloromethane and hydrochloric acid (2N), and the resulting precipitate filtered, washed with water and diethyl ether, and dried. The filtrate was separated, and the organic layer washed with hydrochloric acid (2N), saturated aqueous sodium bicarbonate solution, brine, then dried (MgSO₄) and evaporated under reduced pressure. The residue was triturated with diethyl ether, and the resulting solid filtered and dried. The isolated solids were combined to provide the title compound (6.9 g, 79%).

¹H NMR (400 MHz, d₆-DMSO): δ=1.35 (t, 3H), 4.10 (s, 3H), 4.54 (q, 2H), 8.39 (s, 1H), 8.70 (d, 1H), 9.19 (d, 1H), 11.92 (s, 1H). LRMS 317 (MH)⁺. Found: C, 49.36; H, 3.82; N, 26.57. C₁₃H₁₂N₆O₄ requires C, 49.18; H, 3.77; N, 26.53%.

Example 53

3-Bromo-5-(2-ethoxy-5-nitropyridin-3-yl)-2-methyl-2,6-dihydro-7H-pyrazolo[4,3-d]pyrimidin-7-one A mixture of the title compound of Example 52 (6.9 g, 21.8 mmol), bromine (1.35 mL, 26.2 mmol), and sodium acetate (2.7 g, 32.7 mmol) in acetic acid (100 mL) was heated under reflux for 7 h, then allowed to cool. Additional bromine (0.35 mL, 6.8 mmol) was added and the reaction stirred at room temperature for a further 18 h. The reaction mixture was concentrated under reduced pressure and azeotroped with toluene. The residue was partitioned between dichloromethane and water and the resulting precipitate filtered off, washed with dichloromethane, water, then diethyl ether and dried.

The filtrate was separated, and the organic layer washed with aqueous saturated sodium bicarbonate solution, and brine, then dried (MgSO₄) and evaporated under reduced pressure to give a yellow solid. The isolated solids were combined, suspended in ethyl acetate, and stirred for 30 minutes. The resulting precipitate was filtered off, and dried to afford the title compound (7.66 g, 89%).

¹H NMR (400 MHz, d₆-DMSO): δ=1.35 (t, 3H), 4.10 (s, 3H), 4.54 (q, 2H), 8.70 (d, 1H), 9.20 (d, 1H), 12.16 (s, 1H). LRMS 394.6 (MH)⁺. Found: C, 39.51: H, 2.80; N, 21.27. C₁₃H₁₁BrN₆O₄ requires C, 39.63; H, 2.73; N, 21.36%.

Example 54

3-Bromo-5-(5-amino-2-ethoxy-pyridin-3-yl)-2-methyl-2,6-dihydro-7H-pyrazolo[4,3-d]pyrimidin-7-one Titanium trichloride (20.93 g, 140 mL of a 15% solution in hydrochloric acid) was added to a solution of 3-bromo-5-(2-ethoxy-5-nitropyridin-3-yl)-2-methyl-2,6-dihydro-7H-pyrazolo[4,3-d]pyrimidin-7-one (Example 53) (7.66 g, 19.4 mmol) in acetic acid (100 mL). After 2 h the acetic acid was evaporated and azeotroped with toluene. The residue was partitioned between sodium bicarbonate solution and dichloromethane and the titanium salts filtered to aid separation of the aqueous and organic phases. The aqueous layer was saturated with sodium chloride and re-extracted with dichloromethane. The organics were dried (MgSO$_4$) and concentrated to give a solid. Trituration with ethyl acetate gave 3 g of pure product.

$^1$H NMR (400 MHz, CDCl$_3$): δ=1.40 (t, 3H), 3.80 (br s, 2H), 4.00 (s, 3H), 4.40 (q, 2H), 7.65 (s, 1H), 8.10 (s, 1H), 11.15 (s, 1H). LRMS (TSP): 363.8, 366.8 (MH$^+$).

Example 55

3-Bromo-5-(2-ethoxy-5-iodo-3-pyridinyl)-2-methyl-2,6-dihydro-7H-pyrazolo[4,3-d]pyrimidin-7-one Butyl nitrite (282 mg, 2.74 mmol) was added dropwise to a stirred suspension of the title compound of Example 54 (200 mg, 0.55 mmol) in diiodomethane (2 mL) at room temperature. After 1 h the reaction was warmed for 2 h at 40–50° C. The mixture was cooled and purified directly by flash column chromatography (gradient elution from dichloromethane to 98% dichloromethane/5% methanol) to give the product as a brown solid (60 mg, 23%).

$^1$H NMR (400 MHz, CDCl$_3$): δ=1.50 (t, 3H), 4.15 (s, 3H), 4.60 (q, 2H), 8.40 (s, 1H), 9.00 (s, 1H), 10.90 (s, 1H). LRMS (TSP): 475.6 (MH$^+$).

Example 56 (Preparative Example)

3-Bromo-5-(2-ethoxy-5-trimethylsilyiethynyl-3-pyridinyl)-2-methyl-2,6-dihydro-7H-pyrazolo[4,3-d]pyrimidin-7-one The title compound was made by the method of Example 14 using the title compound of Example 55.

$^1$H NMR (300 MHz, CDCl$_3$): δ=0.25 (s, 9H), 1.55 (t, 3H), 4.20 (s, 3H), 4.65 (q, 2H), 8.40 (s, 1H), 8.85 (s, 1H), 10.95 (s, 1H). LRMS (TSP): 446.3 and 448.5 (MH$^+$).

Example 57

3-Bromo-5-(2-ethoxy-5-ethynyl-3-pyridinyl)-2-methyl-2,6-dihydro-7H-pyrazolo[4,3-d]pyrimidin-7-one The title compound was made by the method of Example 15 using the title compound of Example 56.

$^1$H NMR (400 MHz, CDCl$_3$): δ=1.50 (t, 3H), 3.20 (s, 1H), 4.10 (s, 3H), 4.65 (q, 2H), 8.35 (s, 1H), 8.80 (s, 1H), 10.90 (s, 1H). LRMS (ES): 373 (MH$^+$).

Example 58

5-(5-Acetyl-2-ethoxy-3-pyridinyl)-3-bromo-2-methyl-2,6-dihydro-7H-pyrazolo[4,3-d]pyrimidin-7-one A mixture of 3-bromo-5-(2-ethoxy-5-ethynyl-3-pyridinyl)-2-methyl-2,6-dihydro-7H-pyrazolo[4,3-d]pyrimidin-7-one (Example 57) (750 mg, 2 mmol), 1N H$_2$SO$_4$ (2 mL) and HgSO$_4$ (50 mg, 0.17 mmol) in acetone (25 mL) was stirred at reflux for 10 h then at room temperature for 14 h. Further H$_2$SO$_4$ (5 mL of 1 N) was added and refluxing was continued for a further 4 h. The mixture was cooled and the solvent evaporated and the residue partitioned between dichloromethane and water. After basifying with solid sodium bicarbonate a white precipitate formed which was filtered off before separating the phases. The organic layer was dried (MgSO$_4$), concentrated and combined with the solid previously filtered to give the title compound as a poorly soluble solid.

$^1$H NMR (400 MHz, d$_6$-DMSO): δ=1.30 (t, 3H), 2.60 (s, 3H), 4.10 (s, 3H), 4.40 (q, 2H), 8.40 (s, 1H), 8.90 (s, 1H), 12.00 (br s, 1H). LRMS (TSP): 393.7 (MH$^+$).

Example 59

5-(5-Acetyl-2-ethoxy-3-pyridinyl)-3-[6-(dimethylamino)-3-pyridinyl]-2-methyl-2,6-dihydro-7H-pyrazolo[4,3-d]pyrimidin-7-one Potassium carbonate (35 mg, 0.25 mmol), 6-(dimethylamino)pyridin-3-yl boronic acid dihydrochloride (42 mg, 0.25 mmol) and 5-(5-acetyl-2-ethoxy-3-pyridinyl)-3-bromo-2-methyl-2,6-dihydro-7H-pyrazolo[4,3-d]-pyrimidin-7-one (Example 58) (50 mg, 0.13 mmol) were suspended in dioxan/water (2 mL of a 4:1 mix) and the reaction mixture was immersed in a pre-heated oil bath (120° C.) for 5 min. The mixture was cooled and Pd(PPh$_3$)$_4$ (14 mg, 0.012 mmol) was added. The mixture was reheated to reflux for 2 h. More Pd(PPh$_3$)$_4$ (15 mg, 0.012 mmol) and 6-(dimethyl-amino)pyridin-3-yl boronic acid dihydrochloride (32 mg, 0.25 mmol) were added and reflux was continued for 14 h. The cooled reaction mixture was concentrated and the residue partitioned between dichloromethane and water and filtered through a plug of Celite®. The organic layer was washed with saturated sodium bicarbonate and brine, dried (MgSO$_4$), filtered and evaporated. The yellow residual solid was purified by flash column chromatography (gradient elution from dichloromethane/0.2% ammonia to 99% dichloromethane/methanol/0.5% ammonia) to give 30 mg of the title compound. Further purification by trituration with ether and recrystallisation from isopropyl alcohol to give 18 mg of pure product.

$^1$H NMR (400 MHz, CDCl$_3$): δ=1.60 (t, 3H), 2.60 (s, 3H), 3.20 (s, 6H), 4.20 (s, 3H), 4.80 (q, 2H), 6.70 (d, 1H), 7.80 (d, 1H), 8.40 (s, 1H), 8.80 (s, 1H), 9.20 (s, 1H), 10.75 (s, 1H). LRMS (TSP) 434.5 (MH$^+$).

Example 60

5-(5-Amino-2-ethoxy-3-pyridinyl)-2-methyl-3-propyl-2,6-dihydro-7H-pyrazolo[4,3-d]pyrimidin-7-one Potassium t-butoxide (15.5 g, 0.14 mol) was added to a stirred solution of the title compound from Preparation 23 (12 g, 35 mmol) in t-butanol (300 mL). The mixture was refluxed for 39 h and then cooled (reaction had not gone to completion). The solvent was removed in vacuo and the resulting thick mixture dissolved in water and neutralised to pH 5 with 2 N hydrochloric acid. The aqueous was extracted with dichloromethane (3 times) and the organics were dried (MgSO$_4$) and concentrated. Purification by flash column chromatography (ethyl acetate as eluant) gave 1.5 g of desired product and recovered starting material.

$^1$H NMR (300 MHz, CDCl$_3$): δ=1.00 (t, 3H), 1.50 (t, 3H), 1.80 (m, 2H), 3.00 (t, 2H), 3.60 (br s, 2H), 4.10 (s, 3H), 4.60 (q, 2H), 7.80 (s, 1H), 8.20 (s, 1H), 11.15 (s, 1H).

Example 61

N-[6-Ethoxy-5-(2-methyl-7-oxo-3-Propyl-6,7-dihydro-2H-pyrazolo[4,3-d]pyrimidin-5-yl)-3-pyridinyl]methanesulfonamide Methanesulfonyl chloride (0.056 mL, 7.24 mmol) was added to a stirred solution of 5-(5-amino-2-ethoxy-3-pyridinyl)-2-methyl-3-propyl-2,6-dihydro-7H-pyrazolo[4,3-d]pyrimidin-7-one (Example 60) (158 mg, 0.48 mmol) in pyridine (3 mL) at room temperature for 16 h. The mixture was partitioned between 3% sodium bicarbonate solution and ethyl acetate. The organic layer was washed with 0.5 N hydrochloric acid and water, dried (MgSO$_4$) and evaporated to give 0.1 g of a yellow solid. Trituration with dichloromethane (twice) gave the product as a yellow solid (50 mg).

$^1$H NMR (300 MHz, d$_6$-DMSO): δ=0.95 (t, 3H), 1.30 (t, 3H), 1.70 (m, 2H), 2.90 (t, 2H), 3.00 (s, 3H), 4.00 (s, 3H), 4.40 (q, 2H), 7.95 (s, 1H), 8.15 (s, 1H), 9.65 (br s, 1H), 11.60 (s, 1H). LRMS (TSP): 407.3 (MH$^+$).

Example 62

N-[6-Ethoxy-5-(2-methyl-7-oxo-3-propyl-6,7-dihydro-2H-pyrazolo[4,3-d]-pyrimidin-5-yl)-3-pyridinyl]nicotinamide Nicotinic acid (68 mg, 0.55 mmol) in dichloromethane (2 mL) was treated with oxalyl chloride (0.24 mL, 2.75 mmol) under a nitrogen atmosphere and 1 drop of N,N-dimethylformamide was added. After 2 h solvent was removed in vacuo azeotroping twice with dichloromethane to give a white solid. To this solid was added 5-(5-amino-2-ethoxy-3-pyridinyl)-2-methyl-3-propyl-2,6-dihydro-7H-pyrazolo[4,3-d]pyrimidin-7-one (Example 60) (150 mg, 0.46 mmol), dichloromethane (5 mL) and triethylamine (0.16 mL, 1.15 mmol) and the reaction mixture was stirred for 2 h. The mixture was poured into saturated sodium bicarbonate solution and extracted with ethyl acetate (twice). The combined organics were dried (MgSO$_4$) and concentrated to give a beige semi-solid. Flash column chromatography (gradient elution from 5% methanol:dichloromethane to 10% methanol:dichloromethane) gave 35 mg of the product as a beige solid.

$^1$H NMR (300 MHz, CDCl$_3$): δ=0.95 (t, 3H), 1.45 (t, 3H), 1.80 (m, 2H), 2.90 (t, 2H), 4.00 (s, 3H), 4.60 (q, 2H), 7.40 (m, 1H), 8.25 (d, 1H), 8.65 (m, 2H), 9.00 (s, 1H), 9.20 (s, 1H), 10.00 (s, 1H), 10.90 (s, 1H). TLC (10% methanol:dichloromethane)-R$_f$=0.42.

Example 63

5-(2-Propoxy-5-iodo-3-pyridinyl)-3-ethyl-7-oxo-6,7-dihydro-2H-pyrazolo-[4,3-d]pyrimidin-5-yl] nicotinate A solution of the title compound from Preparation 32 (1.0 g, 2.3 mmol) in propanol (10 mL) and ethyl acetate (0.5 mL) was treated with potassium tert-butoxide (253 mg, 2.3 mmol) and heated to reflux for 24 h. After evaporation to dryness, the reaction mixture was partitioned between ethyl acetate and water whereupon a white solid precipitated which was separated by filtration. The organic phase was separated, dried over Na$_2$SO$_4$, concentrated and combined with the above solid, and this then washed with ethyl acetate and recrystallised from hot methanol-dichloromethane to afford the title compound as a white solid (553 mg, 1.3 mmol).

$^1$H NMR (300 MHz, d$_6$-DMSO): δ=0.9 (t, 3H), 1.3 (t, 3H), 1.6–1.8 (m, 2H), 2.8–2.95 (2H, br m), 4.25 (t, 2H), 8.25 (s, 1H), 8.5 (s, 1H). LRMS (TSP) 426 (MH$^+$), 443 (MNH$_4^+$). Analysis: found C, 42.40; H, 3.69; N, 16.39. Calcd for C$_{15}$H$_{16}$IN$_5$O$_2$: C, 42.37; H, 3.796; N, 16.47%.

Examples 64 and 65 tert-Butyl [3-Ethyl-5-(5-iodo-2-propoxy-3-pyridinyl)-7-oxo-6,7-dihydro-1H-pyrazolo[4,3-d]pyrimidin-1-yl]acetate and tert-Butyl [3-Ethyl-5-(5-iodo-2-propoxy-3-pyridinyl)-7-oxo-6,7-dihydro-2H-pyrazolo[4,3-d]pyrimidin-2-yl]acetate A solution of title compound of Example 63 (450 mg, 1.1 mmol) in N,N-dimethylformamide (10 mL) was treated with cesium carbonate (345 mg, 1.1 mmol) and tert-butyl bromoacetate (156 μL, 1.1 mmol). After stirring at room temperature for 2 h, additional tert-butyl bromoacetate (50 μL, 0.3 mmol) was added and the reaction stirred for a further 0.5 h. The reaction mixture was diluted with water (75 mL) and extracted with ethyl acetate (4×25 mL). The combined organic extracts were washed with brine (25 mL), dried over Na$_2$SO$_4$ and concentrated, and the residue purified by flash column chromatography (dichloromethane:methanol: 0.88 ammonia (95:5:0.5) as eluant). The first isomer to be eluted off the column was the compound of Example 64—tert-butyl [3-ethyl-5-(5-iodo-2-propoxy-3-pyridinyl)-7-oxo-6,7-dihydro-1H-pyrazolo[4,3-d]pyrimidin-1-yl]acetate, which was crystallised from diisopropyl ether (83 mg, 0.15 mmol).

$^1$H NMR (300 MHz, CDCl$_3$): δ=1.1 (t, 3H), 1.4 (t, 3H), 1.5 (s, 9H), 1.9–2.05 (m, 2H), 3.05 (q, 2H), 4.5 (t, 2H), 5.25 (s, 2H), 8.45 (s, 1H), 9.05 (s, 1H), 11.0 (br s, 1H). LRMS (TSP) 541 (MH$^+$). Analysis: found C, 46.76; H, 4.83; N, 12.85. Calcd for C$_{21}$H$_{26}$IN$_5$O$_4$: C, 46.75; H, 4.86; N, 12.98%.

The second isomer (the compound of Example 65)—tert-butyl [3-ethyl-5-(5-iodo-2-propoxy-3-pyridinyl)-7-oxo-6,7-dihydro-2H-pyrazolo[4,3-d]-pyrimidin-2-yl]acetate was also crystallised from diisopropyl ether (147 mg, 0.27 mmol).

$^1$H NMR (300 MHz, CDCl$_3$): δ=1.05 (t, 3H), 1.4–1.6 (m, 12H), 1.95–2.05 (m, 2H), 3.0 (q, 2H), 4.6 (t, 2H), 5.0 (s, 2H), 8.4 (s, 1H), 8.95 (s, 1H), 10.75 (br s, 1H). LRMS (TSP) 541 (MH$^+$), 558 (MNH$_4^+$). Analysis: found C, 46.71; H, 4.83; N, 12.86. Calcd for C$_{21}$H$_{26}$N$_5$O$_4$I: C, 46.75; H, 4.86; N, 12.98%.

The isomers were distinguished by nOe studies.

Example 66

[3-Ethyl-5-(5-iodo-2-propoxy-3-pyridinyl)-7-oxo-6,7-dihydro-1H-pyrazolo[4,3-d]pyrimidin-1-yl]acetic Acid The title compound of Example 64 (50 mg, 0.1 mmol) was dissolved in trifluoroacetic acid (0.5 mL) and the solution stood at room temperature overnight. The trifluoroacetic acid was removed by evaporation and the resultant gum taken up in ethyl acetate (2 mL). A white solid crystallised out and was washed with further ethyl acetate to give the title compound (63% yield).

$^1$H NMR (400 MHz, F$_3$CCO$_2$D): δ=0.95 (t, 3H), 1.3 (t, 3H), 1.8–1.95 (m, 2H), 3.0 (q, 2H), 4.55 (t, 2H), 5.6 (s, 2H), 8.55 (s, 1H), 8.9 (s, 1H). LRMS (ES-positive ion) 484 (MH$^+$), 506 (MNa$^+$). (ES-negative ion) 438 (M-CO$_2$H), 482 (M-H).

Example 67

[3-Ethyl-5-(5-iodo-2-propoxy-3-pyridinyl)-7-oxo-6,7-dihydro-2H-pyrazolo[4,3-d]pyrimidin-2-yl]acetic Acid The title compound was prepared in 65% yield from tert-butyl [3-ethyl-5-(5-iodo-2-propoxy-3-pyridinyl)-7-oxo- 6,7-dihydro-2H-pyrazolo[4,3-d]-pyrimidin-2-yl]acetate (the compound of Example 65) using the method of Example 66 to yield a while solid.

$^1$H NMR (400 MHz, F$_3$CCO$_2$D): δ=0.95 (t, 3H), 1.3 (t, 3H), 1.8–1.95 (m, 2H), 3.05 (q, 2H), 4.5 (t, 2H), 5.4 (s, 2H), 8.5 (s, 1H), 8.85 (s, 1H). LRMS (ES-positive ion) 484 (MH$^+$), 506 (MNa$^+$). (ES-negative ion) 438 (M-CO$_2$H), 482 (M–H).

Example 68

[5-(5-Acetyl-2-propoxy-3-pyridinyl)-3-ethyl-7-oxo-6,7-dihydro-1H-pyrazolo[4,3-d]pyrimidin-1-yl] acetic Acid The product of Example 64 (100 mg, 0.19 mmol) was dissolved in acetonitrile (3 mL) at 30° C. and tri-orthotolylphosphine (10 mg, 0.03 mmol), palladium acetate (3.5 mg), triethylamine (44 μL, 0.32 mmol) and butyl vinyl ether (51 μL, 0.39 mmol) were added. The resultant mixture was heated to reflux for 10 h, allowed to cool to room temperature, hydrochloric acid (6 M, 1.5 mL) was added and the mixture allowed to stir at room temperature for 6 h. Water (5 mL) was added and the reaction mixture extracted with ethyl acetate (3×5 mL). Combined organic extracts were washed with saturated brine (5 mL), dried over Na$_2$SO$_4$, and concentrated to a yellow gum. Purification by column chromatography (dichloromethane:methanol:acetic acid (90:10:1) as eluant) gave a residue which was crystallised from ethyl acetate and further purified by column chromatography (dichloromethane:methanol acetic acid (90:10:1) as eluant) and finally crystallised from ethyl acetate to afford a white solid (18 mg, 0.04 mmol).

$^1$H NMR (300 MHz, d$_6$-DMSO): δ=0.95 (t, 3H), 1.3 (t, 3H), 1.7–1.85 (m, 2H), 2.6 (s, 3H), 2.85 (q, 2H), 4.4 (t, 2H), 5.25 (s, 2H), 8.05 (s, 1H), 8.95 (s, 1H), 12.3 (br s, 1H). LRMS (ES-negative ion) 354 (M-CO$_2$H), 398 (M–H).

Example 69

5-(2-Propoxy-5-iodo-3-pyridinyl)-1-methyl-3-propyl-1,6-dihydro-7H-pyrazolo[4,3-d]pyrimidin-7-one The title compound from Preparation 33 (1.0 g, 2.1 mmol) was dissolved in propanol (25 mL), potassium tert-butoxide (200 mg, 1.8 mmol) added, and the resultant mixture heated to reflux for 3.5 h. After removal of the propanol in vacuo, the residue was purified by column chromatography (dichloromethane:methanol (99:1) as eluant) to give the title compound as a white solid (0.83 g, 86%).

$^1$H NMR (300 MHz, CDCl$_3$): δ=1.05 (t, 3H), 1.15 (t, 3H), 1.8–2.05 (m, 4H), 2.95 (t, 2H), 4.25 (s, 3H), 4.55 (t, 2H), 8.45 (s, 1H), 9.05 (s, 1H), 10.9 (s, 1H). LRMS (ES-negative ion) 452 (M–H), (ES-positive ion) 454 (MH$^+$). Analysis: found C, 44.92; H, 4.36; N, 15.33. Calcd for C$_{17}$H$_{20}$IN$_5$O$_2$: C, 45.05; H, 4.45; N, 15.45%.

Example 70

5-(1-Methyl-7-oxo-3-propyl-6,7-dihydro-1-pyrazolo[4,3-d]pyrimidin-5-yl)-6-propoxynicotinonitrile The title compound was prepared from the title compound of Example 69 using the method of Example 35.

m.p. 174–6° C.

$^1$H NMR (300 MHz, CDCl$_3$): δ=1.05 (t, 3H), 1.2 (t, 3H), 1.8–2.1 (m, 4H), 2.95 (t, 2H), 4.25 (s, 3H), 4.65 (t, 2H), 8.55 (s, 1H), 9.1 (s, 1H), 10.8 (s, 1H). LRMS (TSP) 353 (MH$^+$).

Example 71

1-Methyl-5-[2-propoxy-5-(1H-tetrazol-5-yl)-3-pyridinyl]-3-propyl-1,6-dihydro-7H-pyrazolo[4,3-d] pyrimidin-7-one The title compound was prepared from the product of Example 70 using the method of Example 43.

$^1$H NMR (300 MHz, d$_6$-DMSO): δ=0.9–1.05 (m, 6H), 1.65–1.85 (m, 4H), 2.8 (t, 2H), 4.15 (s, 3H), 4.4 (t, 2H), 8.55 (s, 1H), 8.95 (s, 1H), 12.2 (s, 1H). LRMS (TSP) 396 (MH$^+$).

Example 72

Ethyl 3-[5-(1-Methyl-7-oxo-3-propyl-6,7-dihydro-1H-pyrazolo[4,3-d]-pyrimidin-5-yl)-6-propoxy-3-pyridinyl-2-propynoate A solution of ethyl propiolate (0.2 mL, 1.9 mmol) in tetrahydrofuran (5 mL) was cooled to -65° C. and sec-butyllithium (1.3 M in cyclohexane, 1.5 mL, 1.9 mmol) added maintaining temperature <-65° C. After 1 h, a solution of zinc chloride in tetrahydrofuran (0.5 M, 12 mL, 5.7 mmol) was added and the mixture allowed to warm to room temperature, stirred for a further 0.5 h, cooled in ice and the product of Example 69 (430 mg, 0.95 mmol) added in tetrahydrofuran (5 mL) together with dichlorobis (triphenylphosphine)palladium(II) (35 mg) in tetrahydrofuran (2 mL). The reaction mixture was heated to 50° C. for 2 h, additional dichlorobis (triphenylphosphine)palladium (II) (35 mg) added and the mixture heated for a further 3 h. After cooling, water (5 mL) and diethyl ether (5 mL) were added, the mixture filtered through Celite®, and the aqueous phase extracted with diethyl ether (3×15 mL). Combined organics were washed with brine (15 mL), dried over MgSO$_4$, concentrated to a residue and purified by column chromatography (ethyl acetate:pentane (1:4) as eluant). The title compound was formed as a pale yellow solid (128 mg, 0.3 mmol) after crystallisation from diisopropylether.

$^1$H NMR (300 MHz, CDCl$_3$): δ=1.05 (t, 3H), 1.15 (t, 3H), 1.4 (t, 3H), 1.8–2.1 (m, 4H), 2.9 (t, 2H), 4.25 (s, 3H), 4.35 (t, 2H), 4.6 (t, 2H), 8.5 (s, 1H), 8.95 (s, 1H), 10.9 (s, 1H). LRMS (TSP) 424 (MH$^+$). Analysis: found C, 61.84; H, 5.89; N, 16.33. Calcd for C$_{22}$H$_{25}$N$_5$O$_4$.0.25H$_2$O: C, 61.74; H, 6.01; N, 16.36%.

Example 73

5-[5-(3-Hydroxy-5-isoxazolyl)-2-propoxy-3-pyridinyl]-1-methyl-3-propyl-1,6-dihydro-7H-pyrazolo[4,3-d]pyrimidin-7-one A suspension of the title compound of Example 72 (110 mg, 0.3 mmol) in ethanol (10 mL) was added to hydroxylamine hydrochloride (54 mg, 0.8 mmol) in aqueous sodium hydroxide (0.26 M, 1 mL) and the resultant solution heated to 30° C. for 16 h. Ethanol was removed in vacuo and water (10 mL) added and the resulting solution acidified to pH 2 (conc. hydrochloric acid) prior to extraction with ethyl acetate (3×20 mL). The combined organic extracts were washed with brine (20 mL), dried over MgSO$_4$, concentrated and the residue purified by column chromatography (eluting with a gradient of ethyl acetate:pentane (20:80 to 100:0) and then ethyl acetate:methanol (90:10)) [OK?] and the desired product crystallised from methanol to give the title compound as a white solid (35 mg, 0.1 mmol).

m.p. 239–241° C.; $^1$H NMR (300 MHz, CDCl$_3$): δ=1.05 (t, 3H), 1.15 (t, 3H), 1.85–2.1 (m, 4H), 2.95 (t, 2H), 4.25 (s, 3H), 4.6 (t, 2H), 6.35 (s, 1H), 8.65 (s, 1H), 9.05 (s, 1H), 11.05 (s, 1H). LRMS (TSP) 411 (MH⁺). Analysis: found C, 58.41; H, 5.41; N, 20.31. Calcd for $C_{22}H_{22}N_6O_4$: C, 58.53; H, 5.40; N, 20.48%.

Example 74

5-(5-Amino-2-Propoxy-3-pyridinyl)-1-methyl-3-propyl-1,6-dihydro-7H-pyrazolo[4,3-d]pyrimidin-7-one and

Example 74a

Benzyl 5-(1-Methyl-7-oxo-3-propyl-6,7-dihydro-1H-pyrazolo[4,3-d]pyrimidin-5-yl)-6-propoxy-3-pyridinylcarbamate The title compound of Preparation 36 (3.0 g, 6.1 mmol) and potassium hexamethyidisilazide (1.97 g, 12.2 mmol) in tert-butanol (200 mL) were heated to 80° C. for 2 h, allowed to cool, and concentrated in vacuo. The residue was dissolved in ethyl acetate (150 mL) and washed with water (75 mL) and brine (50 mL), dried over MgSO₄, and purified by column chromatography (eluting with a gradient of ethyl acetate:pentane (20:80 to 50:50)). Two components were isolated. The more lipophilic ($R_f$=0.75 in 1:1 ethyl acetate:pentane) was benzyl 5-(1-methyl-7-oxo-3-propyl-6,7-dihydro-1H-pyrazolo[4,3-d]pyrimidin-5-yl)-6-propoxy-3-pyridinylcarbamate (777 mg, 1.6 mmol) and the more polar component ($R_f$=0.5 in 1:1 ethyl acetate:pentane) was the title compound (0.49 g, 1.4 mmol).

¹H NMR (300 MHz, d₆-DMSO): δ=1.05 (t, 3H), 1.1 (t, 3H), 1.85–2.0 (m, 4H), 2.9 (t, 2H), 3.6 (s, 2H), 4.25 (s, 3H), 4.45 (t, 2H), 7.75 (d, 1H), 8.2 (d, 1H), 11.3 (br s, 1H). LRMS (TSP) 343 (MH⁺).

Example 75

{[5-(1-Methyl-7-oxo-3-propyl-6,7-dihydro-1H-pyrazolo[4,3-d]pyrimidin-5-yl)-6-propoxy-3-pyridinyl]amino}acetic Acid A solution of sodium bromoacetate (48 mg, 0.33 mmol) in water (1 mL) was added to the title compound of Example 74 (100 mg, 0.3 mmol) and the mixture heated to reflux for 5 days. A further aliquot of sodium bromoacetate (48 mg, 0.33 mmol) was added and heating continued for a further day. After cooling, the reaction mixture was extracted with ethyl acetate (3×2.5 mL) and the combined extracts dried over MgSO₄, and purified by column chromatography (dichloromethane:methanol:acetic acid (390:10:1) as eluant) to afford, after trituration from diisopropylether, a yellow solid (16 mg, 0.04 mmol).

¹H NMR (300 MHz, CDCl₃): δ=1.0 (t, 3H), 1.1 (t, 3H), 1.8–2.0 (m, 4H), 2.9 (t, 2H), 4.05 (s, 2H), 4.25 (s, 3H), 4.45 (t, 2H), 7.65 (d, 1H), 8.2 (d, 1H), 11.25 (br s, 1H). LRMS (ES-negative ion) 399 (M–H). Analysis: found C, 56.61; H, 5.98;, N, 20.43. Calcd for $C_{19}H_{24}N_6O_4+0.2H_2O$: C, 56.48; H, 6.09; N, 20.80%.

Example 76

N-[5-(1-Methyl-7-oxo-3-propyl-6,7-dihydro-1H-pyrazolo[4,3-d]pyrimidin-5-yl)-6-propoxy-3-pyridinyl]-N-(methylsulfonyl)methanesulfonamide Methane sulfonyl chloride (0.02 mL, 0.3 mmol) was added to a solution of the title compound of Example 74 (100 mg, 0.3 mmol) and triethylamine (0.08 mL, 0.6 mmol) in dichloromethane (5 mL) and the reaction mixture stirred at room temperature for.6 h. After dilution with dichloromethane (5 mL), the reaction mixture was washed with water (5 mL), brine (5 mL), dried over MgSO₄, and concentrated to a residue. Purification by column chromatography (eluting with a gradient of ethyl acetate:pentane (30:70 to 50:50)) to give the title compound as a white solid (97 mg, 0. 2 mmol).

¹H NMR (300 MHz, CDCl₃): δ=1.0 (t, 3H), 1.1 (t, 3H), 1.8–1.95 (m, 2H), 2.0–2.2 (m, 2H), 2.9 (t, 2H), 3.5 (s, 6H), 4.25 (s, 3H), 4.6 (t, 2H), 8.25 (d, 1H), 8.75 (d, 1H), 10.9 (br s, 1H). LRMS (TSP) 499 (MH⁺). Analysis: found C, 45.58; H, 5.16; N, 16.67. Calcd for $C_{19}H_{26}N_6O_6S_2$: C, 45.77; H, 5.26; N, 16.86%.

Example 77

N-[5-(1-Methyl-7-oxo-3-propyl-6,7-dihydro-1H-pyrazolo[4,3-d]pyrimidin-5-yl)-6-propoxy-3-pyridinyl]methanesulfonamide The title compound of Example 76 (56 mg, 0.1 mmol) was dissolved in propanol (1.4 mL) and aq. KOH solution (1 M, 0.14 mL) and the mixture heated to 45° C. for 2.5 h. The reaction mixture was concentrated in vacuo and the residue diluted with water (2 mL) and acidified to pH 2–3 with conc. hydrochloric acid to afford a precipitate which was removed by filtration, washed with water and diethyl ether before drying to give the title compound as an off-white solid (26 mg, 0.06 mmol).

¹H NMR (400 MHz, CDCl₃): δ=0.95 (t, 3H), 1.1 (t, 3H), 1.8–1.95 (m, 2H), 1.9–2.0 (m, 2H), 2.9 (t, 2H), 3.05 (s, 3H), 4.25 (s, 3H), 4.5 (t, 2H), 6.25 (br s, 1H), 8.25 (d, 1H), 8.65 (d, 1H), 11 (br s, 1H). LRMS (ES-negative ion) 419 (M–H).

Example 78

Methyl 3-{[5-(1-methyl-7-oxo-3-propyl-6,7-dihydro-1H-pyrazolo[4,3-d]-pyrimidin-5-yl)-6-propoxy-3-pyridinyl]amino}-3-oxopropanoate Methyl malonyl chloride (31 μL, 0.3 mmol) was added dropwise to a stirred solution of the title compound of Example 74 (100 mg, 0.3 mmol) and triethylamine (0.08 mL, 0.6 mmol) in dichloromethane (5 mL). The reaction mixture stirred at room temperature for 24 h, diluted with dichloromethane (5 mL), washed with water (2×2.5 mL), dried over MgSO₄, and concentrated to an orange/brown solid. Purification by column chromatography (ethyl acetate as eluant) gave the title compound as a white solid (96 mg, 0.22 mmol).

¹H NMR (300 MHz, CDCl₃): δ=1.05 (t, 3H), 1.15 (t, 3H), 1.85–2.1 (m, 4H), 2.95 (t, 2H), 3.75 (s, 2H), 3.95 (s, 3H), 4.3 (s, 3H), 4.55 (t, 2H), 8.65 (s, 1H), 8.85 (s, 1H), 9.3 (br s, 1H), 11.15 (br s, 1H). LRMS (ES-positive ion) 443 (MH⁺). Analysis: found C, 56.88; H, 5.87; N, 18.74. Calcd for $C_{21}H_{26}N_6O_5$: C, 57.00; H, 5.92; N, 18.70%.

Example 79

N-[5-(1-Methyl-7-oxo-3-propyl-6,7-dihydro-1H-pyrazolo[4,3-d]pyrimidin-5-yl)-6-propoxy-3-pyridinyl]-3-oxo-β-alanine Sodium hydroxide (2 N, aq., 1 mL) was added to a solution of the title compound of Example 78 (79 mg, 0.18 mmol) in methanol (10 mL) and the resultant mixture stirred at room temperature for 19 h, concentrated in vacuo and the residue dissolved in water (20 mL). After washing with dichloromethane (20 mL), the aqueous phase was acidified to pH 2–3 with 2 M HCl and the resultant white precipitate removed by filtration and dried to afford the title compound (58 mg, 0.14 mmol).

m.p. 261–262° C.; $^1$H NMR (300 MHz, d$_6$-DMSO): δ=0.9–1.0 (m, 6H), 1.65–1.8 (m, 4H), 2.7–2.85 (m, 2H), 3.35 (s, 2H), 4.15 (s, 3H), 4.25–4.35 (m, 2H), 8.3 (s, 1H), 8.5 (s, 1H), 10.35 (br s, 1H); LRMS (ES-negative ion) 427 (M–H); Analysis: found C, 54.32; H, 5.47; N, 18.86. Calcd for $C_{20}H_{24}N_6O_5;0.75H_2O$: C, 54.35; H, 5.82; N, 19.02%.

Example 80

({[5-(1-Methyl-7-oxo-3-propyl-6,7-dihydro-1H-pyrazolo[4,3-d]pyrimidin-5-yl)-6-propoxy-3-pyridinyl]amino}sulfonyl)acetic Acid Chlorosulfonyl chloride (878 mg, 4.6 mmol) in acetonitrile (10 mL) was treated with water (0.08 mL, 4.6 mmol) stirred for 10 min at room temperature, concentrated in vacuo, and the residue dissolved in dichloromethane (10 mL). 1.17 mL of this solution was then added dropwise to a stirred solution of the title compound of Example 74 (200 mg, 0.6 mmol) and triethylamine (0.16 mL, 1.2 mmol) in dichloromethane (10 mL). After 14 h, the reaction mixture was extracted with aqueous sodium hydroxide (2 M, 2×10 mL) and the combined aqueous extracts acidified to pH 3 with conc. hydrochloric acid, and back-extracted with dichloromethane (3×10 mL). The combined organic extracts were dried over MgSO$_4$, and concentrated in vacuo, and the residues purified by column chromatography (eluting with a gradient of dichloromethane:methanol in (95:5 to 80:20) to give the title compound as a cream solid (132 mg, 0.4 mmol).

m.p. 267–270° C.; $^1$H NMR (300 MHz, d$_6$-DMSO): δ=0.9–1.0 (m, 6H), 1.65–1.8 (m, 4H), 2.85 (t, 2H), 3.5 (s, 2H), 4.15 (s, 3H), 4.3 (t, 2H), 8.3 (s, 1H), 8.5 (s, 1H), 10.5 (br s, 1H), 12.0 (br s, 1H); LRMS (ES-negative ion) 463 (M–H).

Example 81

1-Methyl-5-(5-{4-[(4-methylphenyl)sulfonyl]-1-piperazinyl}-2-propoxy-3-pyridinyl)-3-propyl-1,6-dihydro-7H-pyrazolo[4,3-d]pyrimidin-7-one N,N-Bis-(2-chloroethyl)-4-methylbenzenesulfonamide (86 mg, 0.3 mmol) was added to a stirred suspension of the title compound of Example 74 (100 mg, 0.3 mmol) in N,N-diisopropylethylamine (0.5 mL), and the mixture heated to reflux. Two further portions of N,N-bis-(2-chloroethyl)-4-methylbenzene-sulfonamide (each 86 mg, 0.3 mmol) were added after 3 and 6 h. After a total of 21 h, the reaction mixture was allowed to cool to room temperature, diluted with ethyl acetate (2.5 mL) and purified by column chromatography (preabsorbed, eluting with a gradient of ethyl acetate:pentane (20:80 to 30:70) to afford the title compound as a yellow solid (119 mg, 0.21 mol).

$^1$H NMR (300 MHz, CDCl$_3$): δ=1.05 (t, 3H), 1.1 (t, 3H), 1.85–2.0 (m, 4H), 2.45 (s, 3H), 2.9 (t, 2H), 3.25 (br s, 8H), 4.3 (s, 3H), 4.5 (t, 2H), 7.35 (d, 2H), 7.7 (d, 2H), 7.9 (d, 1H), 8.4 (d, 1H), 11.3 (br s, 1H). LRMS (ES-negative ion) 564 (M–H).

Example 82

Methyl {[5-(1-Methyl-7-oxo-3-propyl-6,7-dihydro-1H-pyrazolo[4,3-d]pyrimidin-5-yl)-6-propoxy-3-pyridinyl]amino}acetate The title compound of Example 74 (200 mg, 0.6 mmol) and methylbromoacetate (55 μL, 0.58 mmol) were dissolved in N,N-diisopropylamine (2 mL) and the mixture heated to reflux for 20 h. After cooling, the reaction mixture was pre-absorbed onto silica, and purified by column chromatography (ethyl acetate:pentane (50:50) as eluant) to give the title compound as an off-white solid (139 mg, 0.34 mmol).

m.p. 175° C.; $^1$H NMR (400 MHz, CDCl$_3$): δ=1.0 (t, 3H), 1.15 (t, 3H), 1.8–1.95 (m, 4H), 2.9 (t, 2H), 3.75 (s, 3H), 3.95 (d, 2H), 4.25 (s, 3H), 4.45 (t, 2H), 7.65 (d, 1H), 8.15 (d, 1H), 11.25 (br s, 1H); LRMS (ES-negative ion) 413 (M–H); Analysis: found C, 57.86; H, 6.32; N, 20.21. Calcd for $C_{20}H_{26}N_6O_4$: C, 57.96; H, 6.32; N, 20.28%.

Example 83

Methyl 2-{[5-(1-Methyl-7-oxo-3-propyl-6,7-dihydro-1H-pyrazolo[4,3-d]-pyrimidin-5-yl)-6-propoxy-3-pyridinyl]amino}propanoate The title compound of Example 74 (300 mg, 0.9 mmol) and methyl 2-bromopropionate (98 μL, 0.9 mmol) were dissolved in N,N-diisopropylethylamine (3 mL) and the resultant mixture stirred at room temperature for 14 h, after which additional methyl 2-bromopropionate (24 μL, 0.2 mmol) was added and the mixture heated to reflux for 6 h. The cooled reaction was concentrated in vacuo and the residue purified by column chromatography (pre-absorbed, ethyl acetate: pentane (3:10) as eluant) to afford the title compound as a white solid (258 mg, 0.6 mmol).

m.p. 185–7° C.; $^1$H NMR (300 MHz, CDCl$_3$): δ=1.05 (t, 3H), 1.15 (t, 3H), 1.55 (d, 3H), 1.85–2.0 (m, 4H), 2.9 (t, 2H), 3.75 (s, 3H), 4.1 (t, 1H), 4.3 (s, 3H), 4.45 (t, 2H), 7.7 (d, 1H), 8.15 (d, 1H), 11.4 (br s, 1H). LRMS (ES-negative ion) 427 (M–H). Analysis: found C, 58.77; H, 6.62; N, 19.13. Calcd for $C_{21}H_{28}N_6O_4;0.1EtOAc$: C, 58.78; H, 6.64; N, 19.22%.

Example 84

N-[5-(1-Methyl-7-oxo-3-propyl-6,7-dihydro-1H-pyrazolo[4,3-d]pyrimidin-5-yl)-6-propoxy-3-pyridinyl]alanine The title compound of Example 83 in methanol (5 mL) was treated with a solution of sodium hydroxide (64 mg, 1.6 mmol) in water (2 mL) and the reaction mixture stirred at room temperature for 14 h. After concentration of the reaction mixture in vacuo, water (5 mL) was added and the solution acidified with conc. hydrochloric acid (5 drops) to afford a white precipitate, which was removed by filtration, and dried in vacuo to give the title compound as an off-white solid (180 mg, 0.43 mmol).

$^1$H NMR (300 MHz, CDCl$_3$): δ=1.05 (t, 3H), 1.1 (t, 3H), 1.6 (d, 3H), 1.8–2.0 (m, 4H), 2.9 (t, 2H), 4.2 (t, 1H), 4.25 (s, 3H), 4.45 (t, 2H), 7.7 (d, 1H), 8.15 (d, 1H), 11.3 (br s, 1H). LRMS (ES-negative ion) 413 (M–H), 827 (M$_2$–H). Analysis: found C, 57.12; H, 6.23; N, 19.92. Calcd for $C_{20}H_{26}N_6O_4;0.3H_2O$: C, 57.21; H, 6.39; N, 20.02%.

Example 85

2-[2-(Dimethylamino)ethyl]-5-(2-ethoxy-5-iodo-3-pyridinyl)-3-ethyl-2,6-dihydro-7H-pyrazolo[4,3-d]pyrimidin-7-one The title compound of Preparation 39 (2.1 g, 4.1 mmol) was dissolved in tert-butanol (40 mL), the solution degassed, treated with potassium hexamethyldisilazide (2.66 g, 16.4 mmol) and heated to 60° C. for 24 h. The resultant mixture was concentrated, and the residue taken up in water (200 mL) and extracted with dichloromethane (3×100 mL) and the combined organics dried over MgSO$_4$, concentrated and crystallised from ethyl acetate to afford the title compound as a white solid (1.15 g, 2.4 mmol).

$^1$H NMR (400 MHz, CDCl$_3$): δ=1.4 (t, 3H), 1.5 (t, 3H), 2.3 (t, 6H), 2.9 (t, 2H), 3.0 (q, 2H), 4.4 (t, 2H), 4.6 (q, 2H), 8.4 (s, 1H), 9.0 (s, 1H); LRMS (TSP) 483 (MH$^+$).

Example 86

5-{2-[2-(Dimethylamino)ethyl]-3-ethyl-7-oxo-6,7-dihydro-2H-pyrazolo-[4,3-d]pyrimidin-5-yl}-6-ethoxynicotinic Acid The title compound of Example 85 (1.27 g, 2.6 mmol) in methanol (100 mL) was treated with DMSO (5 mL), triethylamine (2.6 mL, 18.4 mmol), 1,3-bis(diphenylphosphino)propane (434 mg, 1 mmol) and palladium(II) acetate (414 mg, 1.8 mmol), and the resultant mixture heated to 75° C. under 482.6 kPa (70 psi) of CO for 14 h. After filtration through Arbocel®, the reaction mixture was partitioned between dichloromethane (150 mL) and water (150 mL), and the organic phase separated, dried over MgSO$_4$, and concentrated to an orange oil. Purification by column chromatography (eluting with a gradient of dichloromethane:methanol as eluant (100:0 to 90:10) gave methyl 5-{2-[2-(dimethylamino)-ethyl]-3-ethyl-7-oxo-6,7-dihydro-2H-pyrazolo[4,3-d]pyrimidin-5-yl}-6-ethoxynicotinate as a slightly impure pale orange solid (1.18 g).

$^1$H NMR (400 MHz, CDCl$_3$): 1.4 (t, 3H), 1.45 (t, 3H), 2.3 (s, 6H), 2.9 (t, 2H), 3.05 (q, 2H), 3.95 (s, 3H), 4.4 (t, 2H), 4.7 (q, 2H), 8.9 (s, 1H), 0.25 (s, 1H); LRMS (TSP) 415 (MH$^+$).

The crude methyl ester (1.18 g) was taken up in dioxan (20 mL), treated with aq. sodium hydroxide (2 M, 3.4 mL) and the resultant solution stirred at room temperature for 14 h after which the dioxan was removed in vacuo, and the remaining aqueous solution washed with toluene (150 mL), acidified with conc. hydrochloric acid to pH 2, and concentrated to a solid. Trituration with hot ethanol (70 mL) afforded the title compound as a white solid (710 mg, 1.8 mmol).

$^1$H NMR (400 MHz, d$_6$-DMSO): δ=1.3 (t, 3H), 1.35 (t, 3H), 2.8 (s, 6H), 3.1 (q, 2H), 3.6–3.7 (m, 2H), 4.4 (q, 2H), 4.75 (t, 2H), 8.4 (s, 1H), 8.8 (s, 1H), 10.5 (br s, 1H), 11.9 (s, 1H). LRMS (TSP) 401 (MH$^+$).

Example 87

5-{2-[2-(Dimethylamino)ethyl]-3-ethyl-7-oxo-6,7-dihydro-2H-pyrazolo[4,3-d]pyrimidin-5-yl}-6-ethoxy-N-methoxy-N-methylnicotinamide The title compound of Example 86 (710 mg, 1.8 mmol) was dissolved in dichloromethane (150 mL), 1-hydroxybenzotriazole hydrate (263 mg, 1.95 mmol), N,N-diisopropylethylamine (1.26 mL, 7 mmol) and 1-(3-dimethylaminopropyl)-3-ethylcarbodiimide hydrochloride (374 mg, 1.95 mmol) were added followed by N,O-dimethylhydroxylamine hydrochloride (173 mg, 1.8 mmol), and the resultant mixture stirred at room temperature for 14 h. Saturated aq. sodium hydrogen carbonate (80 mL) and dichloromethane (50 mL) were added, the organic phase removed and the aqueous phase extracted with dichloromethane (2×50 mL). The combined organic phases were dried over MgSO$_4$, concentrated and purified by column chromatography (dichloromethane to 10% methanol in dichloromethane as eluant) to afford the title compound as a yellow oil (590 mg, 1.3 mmol).

$^1$H NMR (400 MHz, CDCl$_3$): δ=1.4 (t, 3H), 1.55 (t, 2H), 2.3 (s, 6H), 2.85–2.95 (m, 2H), 3.0 (q, 2H), 3.4 (s, 3H), 3.6 (s, 3H), 4.35–4.45 (m, 2H), 4.7 (q, 2H), 8.7 (s, 1H), 9.2 (s, 1H). LRMS (TSP) 444 (MH$^+$).

Example 88

5-[2-(Cyclobutyloxy)-5-nitro-3-pyridinyl]-1-methyl-3-propyl-1,6-dihydro-7H-pyrazolo[4,3-d]pyrimidin-7-one The title compound of preparation 45 (1.0 g, 2.66 mmol), and potassium hexamethyldisilazide (1.72 g, 10.63 mmol) suspended in cyclobutanol (5 ml) and ethyl acetate (0.5 ml) was heated to reflux for 14 h. After cooling, the solvent was removed in vacuo and the residue taken up in water (20 ml) and extracted with methylene chloride (3×50 ml). Combined organic extracts were washed with brine (50 ml), dried over MgSO$_4$ and concentrated to a yellow solid (800 mg). Purification by column chromatography (elution with 3:7 ethyl acetate:pentane) gave the title compound (295 mg, 0.76 mmol).

m.p. 212–4° C. 1H NMR (300 MHz, CDCl$_3$): δ=1.05 (t, 3H), 1.75–2.1 (m, 4H), 2.3–2.4 (m, 2H), 2.5–2.7 (m, 2H), 2.95 (t, 2H), 4.3 (s, 3H), 5.5–5.6 (m, 1H), 9.1 (s, 1H), 9.5 (s, 1H), 10.8 (br s, 1H). LRMS (TSP) 385 (MH$^+$). Analysis: Found C, 56.03; H, 5.28; N, 21.63. Calcd for C$_{18}$H$_{20}$N$_6$O$_4$: C, 56.24; H, 5.24; N, 21.86%.

Example 89

N-[6-(Cyclobutyloxy)-5-(1-methyl-7-oxo-3-propyl-6,7-dihydro-1H-pyrazolo[4,3-d]pyrimidin-5-yl)-3-pyridinyl]acetamide and Example 90

5-[5-Amino-2-(cyclobutyloxy)-3-pyridinyl]-1-methyl-3-propyl-1,6-dihydro-7H-pyrazolo[4,3-d]pyrimidin-7-one The title compound from example 88 (266 mg, 0.69 mmol) was dissolved in glacial acetic acid (10 ml) and the vessel charged with 5% Pd on carbon (20 mg) and stirred under hydrogen (60 psi) for 14 h. The catalyst was removed by filtration (Arbocel*) and the residue concentrated in vacuo. The residue was taken up in water (5 ml), basified to pH 8 (5% NaHCO$_3$ solution) and extracted with methylene chloride (3×20 ml). Combined organic extracts were washed with brine (20 ml), dried over MgSO$_4$, reduced in vacuo and purified by column chromatography (first with 98:2 methylene chloride:methanol as eluant, then 30:70:1 ethyl acetate:pentane:0.88 ammonia). 5-[5-amino-2-(cyclobutyloxy)-3-pyridinyl]-1-methyl-3-propyl-1,6-dihydro-7H-pyrazolo[4,3-d]pyrimidin-7-one was obtained (70 mg, 0.19 mmol) together with N-[6-(cyclobutyloxy)-5-(1-methyl-7-oxo-3-propyl-6,7-dihydro-1H-pyrazolo[4,3-d]pyrimidin-5-yl)-3-pyridinyl]acetamide (34 mg, 0.09 mmol). 5-[5-Amino-2-(cyclobutyloxy)-3-pyridinyl]-1-methyl-3-propyl-1,6-dihydro-7H-pyrazolo[4,3-d]pyrimidin-7-one:

m.p. 185–185.5° C. 1H NMR (300 MHz, CDCl$_3$): δ=1.05 (t, 3H), 1.65–2.0 (m, 4H), 2.2–2.35 (m, 2H), 2.5–2.6 (m, 2H), 2.9 (t, 2H), 3.6 (s, 2H), 4.25 (s, 3H), 5.3–5.4 (m, 1H), 7.75 (s, 1H), 8.2 (1H, s), 11.3 (br s, 1H). LRMS (TSP) 355 (MH$^+$). Analysis: Found C, 60.73; H, 6.37; N, 22.89. Calcd for C$_{18}$H$_{22}$N$_6$O$_2$.0.1H$_2$O: C, 60.85; H, 6.33; N, 23.14%. N-[6-(Cyclobutyloxy)-5-(1-methyl-7-oxo-3-propyl-6,7-dihydro-1H-pyrazolo[4,3-d]pyrimidin-5-yl)-3-pyridinyl]acetamide:

m.p. 279–281° C. 1H NMR (300 MHz, CDCl$_3$): δ=1.0 (t, 3H), 1.65–1.9 (m, 4H), 2.2 (s, 3H), 2.25–2.3 (m, 2H), 2.5–2.6 (m, 2H), 2.85 (t, 2H), 4.2 (s, 3H), 5.35–5.4 (m, 1H), 7.2 (s, 1H), 8.55 (s, 1H), 8.65 (s, 1H), 11.0 (br s, 1H). LRMS (TSP) 397 (MH$^+$).

Example 91

N'-[6-(Propoxy)-5-(1-methyl-7-oxo-3-propyl-6,7-dihydro-1H-pyrazolo[4,3-d]pyrimidin-5-yl)-3-pyridinyl]-N,N-dimethylurea Dimethylcarbamoyl chloride (0.03 ml, 0.32 mmol) was added to a solution of the title compound of example 74 (100 mg, 0.29 mmol), 4-dimethylaminopyridine (2 mg), and triethylamine (0.08 ml, 0.58 mmol) in methylene chloride (5 ml). The resultant mixture was stirred at room temperature for 10 days, concentrated in vacuo and the residue purified by column chromatography (elution with ethyl acetate) to afford the title compound as a white solid (105 mg, 0.25 mmol).

m.p. 219–220° C. 1H NMR (300 MHz, CDCl$_3$): δ=1.02 (t, 3H), 1.13 (t, 3H), 1.8–1.9 (m, 2H), 1.9–2.0 (m, 2H), 2.90 (t, 2H), 3.06 (s, 6H), 4.26 (s, 3H), 4.52 (t, 2H), 6.26 (br s, 1H), 8.48 (d, 1H), 8.58 (d, 1H), 11.2 (br s, 1H). LRMS (TSP) 414 (MH$^+$). Analysis: Found C, 57.96; H, 6.58; N, 23.65. Calcd for C$_{20}$H$_{27}$N$_7$O$_3$: C, 58.10; H, 6.58; N, 23.71%.

Example 92

N-[6-(Propoxy)-5-(1-methyl-7-oxo-3-propyl-6,7-dihydro-1H-pyrazolo[4,3-d]pyrimidin-5-yl)-3-pyridinyl]acetamide Acetic anhydride (30 μL, 0.35 mmol) was added to a solution of the title compound of example 74 (100 mg, 0.29 mmol) in THF (1 ml) and the resultant solution stirred at room temperature for 2 h. Saturated sodium carbonate (10 ml) and ethyl acetate (10 ml) were added, and the aqueous phase separated and extracted with ethyl acetate (2×10 ml). Combined organics were washed with water (20 ml) and brine (20 ml), dried over MgSO$_4$ and condensed to the title compound as a white solid (101 mg, 0.26 mmol).

m.p. 252–3° C. 1H NMR (300 MHz, CDCl$_3$): δ=1.02 (t, 3H), 1.13 (t, 3H), 1.80–2.0 (m, 4H), 2.23 (s, 3H), 2.90 (t, 2H), 4.26 (s, 3H), 4.52 (t, 2H), 7.13 (br s, 1H), 8.61 (s, 1H), 8.71 (s, 1H), 11.15 (br s, 1H). LRMS (TSP) 385 (MH$^+$). Analysis: Found C, 59.08; H, 6.26; N, 21.45. Calcd for C$_{19}$H$_{24}$N$_6$O$_3$.0.1H$_2$O: C, 59.09; H, 6.32; N, 21.76%.

Example 93

5-[5-(Dimethylamino)-2-propoxy-3-pyridinyl]-1-methyl-3-propyl-1,6-dihydro-7H-pyrazolo[4,3-d]pyrimidin-7-one The title compound of example 74 (100 mg, 0.29 mmol) was added to 37% aqueous formaldehyde solution (0.13 ml, 1.74 mmol) and formic acid (0.21 ml, 5.6 mmol), and the resultant mixture heated to 90° C. for 24 h. After allowing to cool, the reaction mixture was diluted with water (20 ml), neutralised with NaOH (2M) and extracted with ethyl acetate (2×20 ml). The combined extracts were washed with water (20 ml), dried over MgSO$_4$ and concentrated to a residue which was purified by column chromatography (eluting with 1:4 ethyl acetate: pentane) to give the title compound as a yellow solid (24 mg, 0.06 mmol).

m.p. 162–162.5° C. 1H NMR (300 MHz, CDCl$_3$): δ=1.03 (t, 3H), 1.13 (t, 3H), 1.80–2.0 (m, 4H), 2.90 (t, 2H), 2.97 (s, 6H), 4.26 (s, 3H), 4.45 (t, 2H), 5.29 (s, 1H), 7.81 (s, 1H), 8.29 (s, 1H). LRMS (TSP) 371 (MH$^+$). Analysis: Found C, 61.46; H, 7.08; N, 22.62. Calcd for C$_{19}$H$_{26}$N$_6$O$_2$: C, 61.60; H, 7.08; N, 22.59%.

Example 94

Propyl 5-(1-Methyl-7-oxo-3-propyl-6,7-dihydro-1H-pyrazolo[4,3-d]pyrimidin-5-yl)-6-propoxy-3-pyridinylcarbamate The title compound of preparation 36 (114 mg, 0.23 mmol) in propanol (15 ml) was treated with potassium bis(trimethylsilylamide) (148 mg, 0.92 mmol) and the resultant mixture heated to 80° C. for 4.5 h, allowed to cool and concentrated in vacuo. The residue was partioned between water (20 ml) and ethyl acetate (20 ml), and the aqueous phase separated and extracted with ethyl acetate (2×20 ml). The combined organics were washed with water (20 ml), brine (20 ml) and dried (MgSO$_4$) before concentrating to an off-white solid. Purification by column chromatography (eluting with 3:10 ethyl acetate: pentane) gave the title compound as a white solid (60 mg, 0.14 mmol).

m.p. 210–211° C. 1H NMR (300 MHz, CDCl$_3$): δ=1.00 (t, 3H), 1.03 (t, 3H), 1.13 (t, 3H), 1.65–2.0 (m, 6H), 2.90 (t, 2H), 4.16 (t, 2H), 4.26 (s, 3H), 4.52 (t, 2H), 6.5 (br s, 1H), 7.26 (d, 1H), 8.69 (d, 1H), 11.2 (br s, 1H). LRMS (TSP) 429 (MH$^+$). Analysis: Found C, 58.88; H, 6.63; N, 19.61. Calcd for C$_{21}$H$_{28}$N$_6$O$_4$: C, 58.86; H, 6.59; N, 19.61%.

Example 95

3-Ethyl-5-(5-iodo-2-propoxy-3-pyridinyl)-1-[2-(4-morpholinyl)ethyl]-1,6-dihydro-7H-pyrazolo[4,3-d]pyrimidin-7-one The title compound of preparation 48 (15.78 g, 28.4 mmol) was dissolved in n-propanol (200 ml), ethyl acetate (6 ml) and potassium t-butoxide (3.2 g, 28.4 mmol) were added and the resultant mixture heated to reflux for 6 h. Additional potassium t-butoxide (1.6 g, 14.2 mmol) was added and the mixture heated for a further 2 h, after which the solvent was removed in vacuo. The residue was partioned between water (50 ml) and methylene chloride (100 ml) and the organic phase separated. The aqueous phase was extracted with dichloromethane (2×100 ml) and the combined organics dried over MgSO$_4$ and reduced to a yellow solid (17 g). Purification by column chromatography (elution with ethyl acetate) gave the title compound (13.3 g, 24.1 mmol) together with recovered starting material (2.31 g, 4.2 mmol).

m.p. 175–177° C. 1H NMR (300 MHz, CDCl$_3$): δ=1.1 (t, 3H), 1.4 (t, 3H), 1.9–2.05 (m, 2H), 2.45–2.55 (m, 4H), 2.85 (t, 2H), 3.0 (q, 2H), 3.6–3.65 (m, 4H), 4.5 (t, 2H), 4.7 (t, 2H), 8.4 (s, 1H), 9.0 (s, 1H), 10.95 (br s, 1H). LRMS (TSP) 540 (MH$^+$). Analysis: found C, 46.79; H, 5.01; N, 15.44. Calcd for C$_{21}$H$_{27}$N$_6$O$_3$I: C, 46.85; H, 5.05; N, 15.61%.

Example 96

5-(2-Butoxy-5-iodo-3-pyridinyl)-3-ethyl-1-[2-(4-morpholinyl)ethyl]-1,6-dihydro-7H-pyrazolo[4,3-d]pyrimidin-7-one The title compound of preparation 49 (1.25 g, 2.3 mmol) in degassed n-butanol (12 ml) was treated with potassium hexamethyldisilazide (2.18 g, 10.9 mmol) and the reaction mixture heated to reflux for 60 h, After removal of the solvent in vacuo, the residue was partioned between water and methylene chloride, the pH adjusted to 7 (2N HCl) and the aqueous phase separated, and extracted with methylene chloride. Combined organic extracts were washed with brine, dried over $MgSO_4$, and concentrated to a residue which after trituration with pentane, afforded the title compound (0.84 g, 1.5 mmol).

1H NMR (400 MHz, $CDCl_3$): δ=1.02 (t, 3H), 1.4 (t, 3H), 1.5–1.6 (m, 2H), 1.85–1.95 (m, 2H), 2.5–2.6 (m, 4H), 2.85 (t, 2H), 2.97 (q, 2H), 3.6–3.6 (m, 4H), 4.55 (t, 2H), 4.75 (t, 2H), 8.45 (d, 1H), 9.05 (d, 1H), 10.95 (br s, 1H).

Example 97

4-{[5-(2-Ethoxy-5-iodo-3-pyridinyl)-3-ethyl-7-oxo-6,7-dihydro-2H-pyrazolo[4,3-d]pyrimidin-2-yl]methyl}benzonitrile The title compound was prepared from the title compound of preparation 50 in ethanol using the method of example 95.

1H NMR (400 MHz, $CDCl_3$): δ=1.25 (t, 3H), 1.5 (t, 3H), 2.95 (q, 2H), 4.6 (q, 2H), 5.6 (s, 2H), 7.25 (d, 2H), 7.60 (d, 2H), 8.40 (d, 1H), 8.95 (d, 1H), 10.8 (br s, 1H). LRMS 527 ($MH^+$), 549 ($MNa^+$).

Example 98

5-(2-Propoxy-5-iodo-3-pyridinyl)-3-ethyl-2-(2-pyridinylmethyl)-2,6-dihydro-7H-pyrazolo[4,3-d]pyrimidin-7-one The title compound was prepared from the product of preparation 51 using the method of example 95.

m.p. 228.9–233.8° C. 1H NMR (400 MHz, $CDCl_3$): δ=1.05 (t, 3H), 1.25 (t, 3H), 1.90 (m, 2H), 3.00 (q, 2H), 4.50 (t, 2H), 5.65 (s, 2H), 7.05 (d, 1H), 7.20 (m, 1H), 7.60 (t, 1H), 8.40 (s, 1H), 8.55 (d, 1H), 8.95 (s, 1H), 10.70 (s, 1H); LRMS (ES-positive ion) 517 ($MH^+$); Anal. Found C, 48.73; H, 3.89; N, 16.14. Calcd for $C_{21}H_{21}O_2N_6I$: C, 48.85; H, 4.10; N, 16.28.

Example 99 tert-Butyl 3-[3-Ethyl-5-(5-iodo-2-propoxy-3-pyridinyl)-7-oxo-6,7-dihydro-2H-pyrazolo[4,3-d]pyrimidin-2-yl]-1-azetidinecarboxylate The title compound was prepared from the product of preparation 52 using the method of example 95.

1H NMR (400 MHz, $CDCl_3$): δ=1.05 (t, 3H), 1.30 (t, 3H), 1.43 (s, 9H), 1.87–1.96 (m, 2H), 3.00 (q, 2H), 4.34 (t, 2H), 4.49 (t, 2H), 4.60 (br s, 2H), 5.20 (t, 1H), 8.41 (d, 1H), 8.94 (s, 1H), 10.75 (br s, 1H); LRMS (TSP-positive ion) 598.1 ($MNH_4^+$); Anal. Found C, 47.54; H, 5.02; N, 14.09; Calcd for $C_{23}H_{29}O_4N_6I$: C, 47.60; H, 5.04; N, 14.48.

Example 100 tert-Butyl 4-[3-Ethyl-5-(5-iodo-2-propoxy-3-pyridinyl)-7-oxo-6,7-dihydro-2H-pyrazolo[4,3-d]pyrimidin-2-yl]-1-piperidinecarboxylate The title compound was prepared from the product of preparation 53 using the method of example 95.

1H NMR (400 MHz, $CDCl_3$): δ=1.10 (t, 3H), 1.40 (t, 3H), 1.45 (s, 9H), 1.92 (m, 4H), 2.40 (m, 2H), 2.90 (m, 2H), 3.08 (q, 2H), 4.38 (m, 3H), 4.50 (t, 2H), 8.40 (s, 1H), 8.98 (s, 1H), 10.69 (s, 1H). LRMS (TSP-positive ion) 609.7 ($MH^+$), 509.0 ($MH^+$-BOC).

Example 101

3-Ethyl-1-[2-(4-morpholinyl)ethyl]-5-{2-propoxy-5-[(trimethylsilyl)ethynyl]-3-pyridinyl}-1,6-dihydro-7H-pyrazolo[4,3-d]pyrimidin-7-one Prepared by the method of example 14 from the title compound of example 95.

m.p. 132–134° C. 1H NMR (300 MHz, $CDCl_3$): δ=0.25 (s, 9H), 1.1 (t, 3H), 1.4 (t, 3H), 1.95–2.05 (m, 2H), 2.45–2.5 (m, 4H), 2.85 (t, 2H), 3.0 (q, 2H), 3.55–3.65 (m, 4H), 4.55 (t, 2H), 4.7 (t, 2H), 8.35 (s, 1H), 8.8 (s, 1H), 11 (br s, 1H). LRMS (ES-negative ion) 507 (M–H)⁻. (ES-positive ion) 509 ($MH^+$). Analysis: found C, 61.18; H, 7.12; N, 16.53. Calcd for $C_{26}H_{36}N_6O_3Si$: C, 61.39; H, 7.13; N, 16.52%.

Example 102

5-{2-Butoxy-5-[(trimethylsilyl)ethynyl]-3-pyridinyl}-3-ethyl-1-[2-(4-morpholinyl)ethyl]-1,6-dihydro-7H-pyrazolo[4,3-d]pyrimidin-7-one The title compound was prepared by the method of example 14 from the title compound of example 96 in 69% yield (550 mg).

1H NMR (400 MHz, $CDCl_3$): δ=0.38 (s, 9H), 1.02 (t, 3H), 1.42 (t, 3H), 1.5–1.6 (m, 2H), 1.85–1.98 (m, 2H), 2.46–2.56 (m, 4H), 2.85 (t, 2H), 3.0 (q, 2H), 3.55–3.65 (m, 4H), 4.6 (t, 2H), 4.7 (t, 2H), 8.38 (s, 1H), 8.85 (s, 1H), 10.98 (s, 1H). LRMS (TSP) 524 ($MH^+$).

Example 103

4-[(5-{2-Ethoxy-5-(trimethylsilyl)ethynyl]-3-pyridinyl}-3-ethyl-7-oxo-6,7-dihydro-2H-pyrazolo[4,3-d]pyrimidin-2-yl)methyl]benzonitrile The title compound was prepared by the method of example 14 from the product of example 97.

1H NMR (300 MHz, $CDCl_3$): δ=0.27 (s, 9H), 1.30 (t, 3H), 1.54 (t, 3H), 2.95 (q, 2H), 4.68 (q, 2H), 5.61 (s, 2H), 7.30 (d, 2H), 7.65 (d, 2H), 8.38 (d, 1H), 8.76 (d, 1H), 10.83 (s, 1H).

Example 104

3-Ethyl-5-{2-propoxy-5-[(trimethylsilyl)ethynyl]-3-pyridinyl}-2-(2-pyridinylmethyl)-2,6-dihydro-7H-pyrazolo[4,3-d]pyrimidin-7-one Prepared from the title compound of example 98 by the method of example 14.

1H NMR (400 MHz, $CDCl_3$): δ=0.20 (s, 9H), 1.00 (t, 3H), 1.25 (t, 3H), 1.44 (m, 2H), 3.00 (q, 2H), 4.50 (t, 2H), 5.60 (s, 2H), 7.00 (d, 1H), 7.20 (m, 1H), 7.60 (dd, 1H) 8.30 (s, 1H), 8.55 (d, 1H), 8.75 (s, 1H), 10.70 (s, 1H); LRMS (TSP-positive ion) 487.5 ($MH^+$).

Example 105 tert-Butyl 3-(3-Ethyl-7-oxo-5-{2-propoxy-5-[(trimethylsilyl)ethynyl]-3-pyridinyl}-6,7-dihydro-2H-pyrazolo[4,3-d]pyrimidin-2-yl)-1-azetidinecarboxylate Prepared from the title compound of example 99 by the method of example 14.

1H NMR (400 MHz, MeOD): δ=0.25 (s, 9H), 1.05 (t, 3H), 1.31 (t, 3H), 1.44 (s, 9H), 1.87–1.96 (m, 2H), 3.00 (q, 2H), 4.33 (t, 2H), 4.52 (t, 2H), 4.54–4.80 (m, 2H), 5.18–5.25 (m, 1H), 8.32 (d, 1H), 8.74 (d, 1H); LRMS (TSP-positive ion) 569 ($MNH_4^+$), 452.0 ($MH^+$); Anal. Found C, 60.82; H, 6.90; N, 15.15; Calcd for $C_{28}H_{38}O_4N_6Si$: C, 61.07; H, 6.95; N, 15.26.

Example 106 tert-Butyl 4-(3-Ethyl-7-oxo-5-{2-propoxy-5-[(trimethylsilyl)ethynyl]-3-pyridinyl}-6,7-dihydro-2H-pyrazolo[4,3-d]pyrimidin-2-yl)-1-piperidinecarboxylate Prepared from the title compound of example 100 by the method of Example 14.

1H NMR (400 MHz, $CDCl_3$): δ=0.28 (s, 9H), 1.05 (t, 3H), 1.40 (t, 3H), 1.48 (s, 9H), 1.92 (m, 4H), 2.40 (m, 2H), 2.90

(m, 2H), 3.05 (q, 2H), 4.38 (m, 3H), 4.55 (t, 2H), 8.35 (s, 1H), 8.75 (s, 1H), 10.70 (s, 1H); LRMS (TSP-positive ion) 580 (MH$^+$), 479 (MH$^+$-BOC); Anal. Found C, 61.86; H, 7.24; N, 14.30; Calcd for $C_{30}H_{42}O_4N_6Si.0.2H_2O$, C, 61.87; H, 7.34; N, 14.43.

Example 107

3-Ethyl-5-(5-ethynyl-2-propoxy-3-pyridinyl)-1-[2-(4-morpholinyl)ethyl]-1,6-dihydro-7H-pyrazolo[4,3-d]pyrimidin-7-one Prepared by the method of example 15 from the title compound of example 101.

m.p. 137–139° C. 1H NMR (300 MHz, CDCl$_3$): δ=1.15 (t, 3H), 1.4 (t, 3H), 1.95–2.05 (m, 2H), 2.45–2.5 (m, 4H), 2.9 (t, 2H), 3.0 (q, 2H), 3.1 (s, 1H), 3.45–3.65 (m, 4H), 4.55 (t, 2H), 4.7 (t, 2H), 8.4 (s, 1H), 8.9 (s, 1H), 11 (br s, 1H). LRMS (ES-negative ion) 435 (M–H)$^-$. (ES-positive ion) 437 (MH$^+$). Analysis: found C, 62.75; H, 6.47; N, 18.79. Calcd for $C_{23}H_{28}N_6O_4.0.2H_2O$: C, 63.79; H, 6.47; N, 19.25%.

Example 108

5-(2-Butoxy-5-ethynyl-3-pyridinyl)-3-ethyl-1-[2-(4-morpholinyl)ethyl]-1,6-dihydro-7H-pyrazolo[4,3-d]pyrimidin-7-one The title compound was prepared by the method of example 15 from the title compound of example 102 in 88% yield (543 mg).

1H NMR (400 MHz, CDCl$_3$): δ=1.0 (t, 3H), 1.4 (t, 3H), 1.5–1.6 (m, 2H), 1.9 (tt, 2H), 2.5–2.55 (m, 4H), 2.85 (t, 2H), 2.95–3.05 (m, 2H), 3.6–3.65 (4H, m), 4.6 (t, 2H), 4.7 (t, 2H), 8.0 (s, 1H), 8.4 (s, 1H), 8.85 (s, 1H), 10.95 (br s, 1H). LRMS (TSP) 451 (MH$^+$).

Example 109

4-{[5-(2-Ethoxy-5-ethynyl-3-pyridinyl)-3-ethyl-7-oxo-6,7-dihydro-2H-pyrazolo[4,3-d]pyrimidin-2-yl]methyl}benzonitrile The title compound was prepared by the method of example 15 from example 103 in 79% (147 mg).

1H NMR (300 MHz, CDCl$_3$): δ=1.28 (t, 3H), 1.55 (t, 3H), 2.93 (q, 2H), 3.18 (s, 1H), 4.68 (q, 2H), 5.61 (s, 2H), 7.31 (d, 2H), 7.63 (d, 2H), 8.40 (d, 1H), 8.82 (d, 1H), 10.83 (s, 1H).

Example 110

3-Ethoxy-5-(5-ethynyl-2-propyl-3-pyridinyl)-2(2-pyridinylmethyl)-2,6-dihydro-2H-pyrazolo[4,3-d]pyrimidin-7-one The title compound was prepared from the product of example 104 by the method of example 15.

m.p. 189° C.; 1H NMR (400 MHz, CDCl$_3$): δ=1.05 (t, 3H), 1.25 (t, 3H), 1.95 (q, 2H), 3.05 (q, 2H), 3.20 (s, 1H), 4.60 (t, 2H), 5.65 (s, 2H), 7.10 (d, 1H), 7.20 (d, 1H), 7.60 (dd, 1H), 8.40 (s, 1H), 8.60 (d, 1H), 8.80 (s, 1H), 10.80 (s, 1H); LRMS (TSP-positive ion) 415 (MH$^+$); Anal. Found C, 65.05; H, 5.46; N, 19.16. Calcd for $C_{23}H_{22}O_2N_6.0.7H_2O$: C, 64.68; H, 5.52; N, 19.68.

Example 111 tert-Butyl 3-[3-Ethyl-5-(5-ethynyl-2-propoxy-3-pyridinyl)-7-oxo-6,7-dihydro-2H-pyrazolo[4,3-d]pyrimidin-2-yl]-1-azetidinecarboxylate Prepared from the title compound of example 105 by the method of example 15.

1H NMR (400 MHz, CDCl$_3$): δ=1.05 (t, 3H), 1.30 (t, 3H), 1.43 (s, 9H), 1.88–2.00 (m, 2H), 3.00 (q, 2H), 3.19 (s, 1H), 4.35 (app t, 2H), 4.52 (app t, 2H), 4.60–4.80 (br s, 2H), 5.22 (t, 1H), 8.39 (s, 1H), 8.80 (s, 1H), 10.75 (br s, 1H); LRMS (TSP-positive ion) 496 (MNH$_4^+$).

Example 112 tert-Butyl 4-[3-Ethyl-5-(5-ethynyl-2-propoxy-3-pyridinyl)-7-oxo-6,7-dihydro-2H-pyrazolo[4,3-d]pyrimidin-2-yl]-1-piperidinecarboxylate Prepared from the title compound of example 106 by the method of example 15.

m.p. 221° C.; 1H NMR (400 MHz, CDCl$_3$): δ=1.03 (t, 3H), 1.40 (t, 3H), 1.45 (s, 9H), 1.92 (m, 4H), 2.40 (m, 2H), 2.90 (m, 2H), 3.05 (q, 2H), 3.19 (s, 1H), 4.38 (m, 3H), 4.57 (t, 2H), 8.39 (s, 1H), 8.82 (s, 1H), 10.70 (s, 1H); LRMS (TSP-positive ion) 507 (MH$^+$), 524 (MNH$_4^+$).

Example 113

5-(5-Acetyl-2-propoxy-3-pyridinyl)-3-ethyl-1-[2-(4-morpholinyl)ethyl]-1,6-dihydro-7H-pyrazolo[4,3-d]pyrimidin-7-one Prepared by the method of example 16 from the product of example 107.

m.p. 140–143° C. 1H NMR (300 MHz, CDCl$_3$): δ=1.15 (t, 3H), 1.4 (t, 3H), 1.95–2.05 (m, 2H), 2.5–2.55 (m, 4H), 2.7 (s, 3H), 2.85–2.95 (m, 2H), 3.0 (q, 2H), 3.6–3.65 (m, 4H), 4.65 (t, 2H), 4.75 (t, 2H), 8.85 (s, 1H), 9.3 (s, 1H), 10.9 (br s, 1H). LRMS (ES-negative ion) 453 (M–H)$^-$. (ES-positive ion) 455 (MH$^+$). Analysis: found C, 60.43; H, 6.66; N, 18.22. Calcd for $C_{23}H_{30}N_6O_4.0.15H_2O$: C, 60.43; H, 6.68; N, 18.38%.

Example 114

5-(5-Acetyl-2-butoxy-3-pyridinyl)-3-ethyl-1-[2-(4-morpholinyl)ethyl]-1,6-dihydro-7H-pyrazolo[4,3-d]pyrimidin-7-one The title compound was prepared by the method of example 16 from the title compound of example 108 in 73% yield (0.32 mmol).

1H NMR (400 MHz, CDCl$_3$): δ=1.02 (t, 3H), 1.42 (t, 3H), 1.5–1.63 (m, 2H), 1.9–2.0 (m, 2H), 2.45–2.58 (m, 4H), 2.65 (s, 3H), 2.87 (t, 2H), 3.0 (q, 2H), 3.55–3.68 (m, 4H), 4.62–4.75 (m, 4H), 8.85 (s, 1H), 9.3 (s, 1H), 10.88 (br s, 1H). LRMS (EI-positive ion) 469 (MH$^+$).

Example 115

4-{[5-(5-Acetyl-2-ethoxy-3-pyridinyl)-3-ethyl-7-oxo-6,7-dihydro-2H-pyrazolo[4,3-d]pyrimidin-2-yl]methyl}benzonitrile Using the method of example 16, the title compound was prepared from the title compound of example 109 in 65% yield (110 mg).

1H NMR (300 MHz, CDCl$_3$): δ=1.25 (t, 3H), 1.55 (t, 3H), 2.65 (s, 3H), 2.95 (q, 2H), 4.75 (q, 2H), 5.6 (s, 2H), 7.3 (d, 2H), 7.65 (d, 2H), 8.85 (d, 1H), 9.25 (d, 1H), 10.7 (br s, 1H). LRMS (TSP) 443 (MH$^+$), 465 (MNa$^+$).

Example 116

5-(5-Acetyl-2-propoxy-3-pyridinyl)-3-ethyl-2-(2-pyridinylmethyl)-2,6-dihydro-7H-pyrazolo[4,3-d]pyrimidin-7-one Prepared from the title compound of example 110 by the method of example 16.

1H NMR (400 MHz, CDCl$_3$): δ=1.10 (t, 3H), 1.30 (t, 3H), 1.95 (m, 2H), 2.60 (s, 3H), 3.00 (q, 2H), 4.60 (t, 2H), 5.70

(s, 2H), 7.10 (d, 1H), 7.20 (d, 1H), 7.65 (t, 1H), 8.60 (d, 1H), 8.85 (s, 1H), 9.25 (s, 1H), 10.70 (s, 1H); LRMS (TSP-positive ion) 433.4 (MH$^+$); Anal. Found C, 58.21; H, 5.52; N, 17.18. Calcd for $C_{23}H_{24}O_3N_6 \cdot 0.5H_2O \cdot 0.5DCM$: C, 58.32; H, 5.42; N, 17.37.

Example 117

5-(5-Acetyl-2-propoxy-3-pyridinyl)-2-(3-azetidinyl)-3-ethyl-2,6-dihydro-7H-pyrazolo[4,3-d]pyrimidin-7-one The title compound of example 111 (1.44 g, 3.0 mmol) in acetone (50 ml) and sulphuric acid (1N, 3 ml) was treated with mercuric sulphate (268 mg, 9.0 mmol) and heated to reflux for 6 h. The reaction mixture was concentrated to 20 ml in vacuo, poured into sodium bicarbonate (sat. aq., 20 ml) and extracted into methylene chloride (6×20 ml). Combined organics were washed with brine (20 ml), dried over $MgSO_4$, and concentrated to a brown oil which was taken up in 40% trifluoroacetic acid in methylene chloride (50 ml) and water (1 ml) and stirred for 1 h at room temperature. After evaporation in vacuo, the residue was purified by column chromatography (eluting with 95:5:1 methylene chloride:methanol:0.88 ammonia) to afford the title compound as a white hydroscopic foam (1.65 g).

m.p. 128.5–130.0° C.; 1H NMR (400 MHz, MeOD): δ=1.00 (t, 3H), 1.30 (t, 3H), 1.79–1.90 (m, 2H), 2.60 (s, 3H), 3.00–3.10 (q, 2H), 4.50 (t, 2H), 4.60–4.70 (m, 4H), 5.65–5.78 (m, 1H), 8.65 (s, 1H), 8.90 (s, 1H); LRMS (TSP-positive ion) 397 (MH$^+$).

Example 118

5-(5-Acetyl-2-propoxy-3-pyridinyl)-3-ethyl-2-(4-piperidinyl)-2,6-dihydro-7H-pyrazolo[4,3-d]pyrimidin-7-one The title compound was prepared by the method of example 117, using the title compound of example 112.

1H NMR (400 MHz, CDCl$_3$): δ=1.10 (t, 3H), 1.40 (t, 3H), 1.90–1.99 (m, 4H), 2.30–2.40 (m, 2H), 2.65 (s, 3H), 2.80 (t, 2H), 3.08 (q, 2H), 3.32 (app d, 2H), 4.35–4.40 (m, 1H), 4.62 (app t, 2H), 8.85 (s, 1H), 9.25 (s, 1H); LRMS (TSP-positive ion) 425 (MH$^+$); Anal. Found C, 51.36; H, 5.91; N, 15.18; Calcd for $C_{22}H_{28}O_3N_6 \cdot 1.45DCM$, C, 51.43; H, 5.69; N, 15.35.

Example 119

5-(5-Acetyl-2-propoxy-3-pyridinyl)-3-ethyl-2-(1-ethyl-3-azetidinyl)-2,6-dihydro-7H-pyrazolo[4,3-d]pyrimidin-7-one Sodium cyanoborohydride (92 mg, 1.47 mmol) was added to a stirring solution of title compound from example 117 (500 mg, 0.98 mmol) and sodium acetate (161 mg, 1.96 mmol) in methanol (10 ml) under nitrogen at room temperature. After 1 h the mixture was poured into NaHCO$_3$ (sat. aq., 20 ml), and extracted with dichloromethane (3×15 ml). The combined organic layers were dried (MgSO$_4$) and concentrated in vacuo. The crude product was purified by flash column chromatography (95:5:0.5–80:20:1 ethyl acetate:methanol:0.88 NH$_3$ as eluent) to yield the title compound as a white solid (140 mg, 0.33 mmol). 1H NMR (400 MHz, CDCl$_3$): δ=0.97 (t, 3H), 1.03 (t, 3H), 1.30 (t, 3H), 2.82–2.97 (m, 2H), 2.58–2.65 (m, 5H), 2.98 (q, 2H), 3.68 (t, 2H), 3.85 (dd, 2H), 4.58 (dd, 2H), 5.05–5.17 (m, 1H), 8.79 (s, 1H), 9.18 (s, 1H), 10.62 (br s, 1H). LRMS (TSP-positive ion) 426 (MH$^+$).

Example 120

5-(5-Acetyl-2-propoxy-3-pyridinyl)-3-ethyl-2-(1-methyl-3-azetidinyl)-2,6-dihydro-7H-pyrazolo[4,3-d]pyrimidin-7-one The title compound was prepared by the method of example 51 using the title compound of example 117.

m.p. 175.9–177.0° C.; 1H NMR (400 MHz, CDCl$_3$): δ=1.11 (t, 3H), 1.36 (t, 3H), 1.97 (app. q, 2H), 2.50 (s, 3H), 2.65 (s, 3H), 3.02 (q, 2H), 3.79 (t, 2H), 3.92 (dd, 2H), 4.64 (dd, 2H), 5.09–5.19 (m, 1H), 8.85 (d, 1H), 9.23 (d, 1H), 10.65 (br s, 1H); LRMS (TSP-positive ion) 411.6 (MH$^+$); Anal. Found C, 59.70; H, 6.46; N, 19.81; Calcd for $C_{21}H_{26}O_3N_6 \cdot 0.7H_2O$: C, 59.62; H, 6.53; N, 19.86.

Example 121

2-(1-Acetyl-3-azetidinyl)-5-(5-acetyl-2-propoxy-3-pyridinyl)-3-ethyl-2,6-dihydro-7H-pyrazolo[4,3-d]pyrimidin-7-one The title compound of example 117 (100 mg, 0.25 mmol) was dissolved in methylene chloride (15 ml). Pyridine (20 ?l, 0.25 mmol) and acetic anhydride (24 ?l, 0.25 mmol) were added and the mixture stirred at room temperature for 1 h, poured into water (20 ml), the organic phase separated and the aqueous phase extracted into methylene chloride (2×20 ml). Combined organics were washed with HCl (1N, 10 ml), dried over MgSO$_4$, condensed in vacuo, and purified by column chromatography (90:10:1 methylene chloride:methanol:ammonia as eluent) to afford the title compound as a white solid (48 mg, 0.11 mmol).

m.p. 229.3–230.1° C.; 1H NMR (400 MHz, CDCl$_3$): δ=1.1 (t, 3H), 1.38 (t, 3H), 1.90–2.08 (m, 5H), 2.62 (s, 3H), 3.02 (q, 2H), 4.46 (d, 2H), 4.56 (dd, 1H), 4.60 (dd, 2H), 5.00–5.10 (m, 1H), 5.26–5.40 (m, 1H), 8.82 (s, 1H), 9.22 (s, 1H), 10.70 (br s, 1H); LRMS (TSP-positive ion) 439 (MH$^+$), 456 (MNH$_4^+$); Anal. Found C, 56.56; H, 5.82; N, 17.46; Calcd for $C_{22}H_{26}O_4N_6 \cdot 0.45CH_2Cl_2$: C, 56.56; H, 5.69; N, 17.63.

Example 122

2-(1-acetyl-4-piperidinyl)-5-(5-acetyl-2-propoxy-3-pyridinyl)-3-ethyl-2,6-dihydro-7H-pyrazolo[4,3-d]pyrimidin-7-one The title compound was prepared by the method of example 121 from the title compound of example 118.

m.p. 213–214° C. 1H NMR (400 MHz, CDCl$_3$): δ=1.19 (t, 3H), 1.40 (t, 3H), 1.90–2.02 (m, 4H), 2.17 (s, 3H), 2.25–2.38 (m, 1H), 2.50–2.60 (m, 1H), 2.65 (s, 3H), 2.70–2.80 (m, 1H), 3.08 (q, 2H), 3.21–3.30 (m, 1H), 4.01–4.10 (m, 1H), 4.45–4.52 (m, 1H), 4.60 (t, 2H), 4.78–4.85 (m, 1H), 8.84 (s, 1H), 9.22 (s, 1H), 10.64 (s, 1H); LRMS (TSP-positive ion) 467 (MH$^+$), 484 (MNH$_4^+$), 489 (MNa$^+$); Anal. Found C, 59.67; H, 6.37; N, 17.15; Calcd for $C_{24}H_{30}O_4N_6 \cdot 0.4H_2O \cdot 0.15CH_2Cl_2$, C, 59.62; H, 6.44; N, 17.27.

Example 123

5-(5-Acetyl-2-propoxy-3-pyridinyl)-2-(1-sec-butyl-3-azetidinyl)-3-ethyl-2,6-dihydro-7H-pyrazolo[4,3-d]pyrimidin-7-one The title compound was prepared by the method of example 51 using the title compound of example 117 and but-2-one.

m.p. 176.5–177.7° C.; 1H NMR (400 MHz, CDCl$_3$): δ=0.85 (t, 3H), 0.93 (d, 3H), 1.06 (t, 3H), 1.11–1.18 (m, 1H), 1.32 (t, 3H), 1.46–1.55 (m, 1H), 1.89–1.98 (m, 2H), 2.36–2.41 (m, 1H), 2.61 (s, 3H), 2.99 (q, 2H), 3.67–3.74 (m, 2H), 3.85 (t, 2H), 4.59 (t, 2H), 5.06–5.13 (m, 1H), 8.81 (s, 1H), 9.19 (s, 1H), 10.60 (br s, 1H); LRMS (TSP-positive ion) 453 (MH$^+$); Anal. Found C, 60.03; H, 6.93; N, 17.14; Calcd for $C_{24}H_{32}O_3N_6 \cdot 0.4H_2O \cdot 0.3CH_2Cl_2$: C, 60.15; H, 6.94; N, 17.32.

Example 124

5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one The title compound was prepared by the method of example 51 using the title compound of example 117 and acetone.

m.p. 162.8–163.6° C.; 1H NMR (400 MHz, MeOD): δ=1.00 (app. d, 9H), 1.30 (t, 3H), 1.84 (app. q, 2H), 2.60 (s, 3H), 2.62–2.72 (m, 1H), 3.00–3.10 (q, 2H), 3.75 (t, 2H), 3.90 (t, 2H), 4.50 (t, 2H), 5.25 (t, 1H), 8.70 (s, 1H), 8.90 (s, 1H); LRMS (TSP-positive ion) 439 (MH$^+$); Anal. Found C, 61.92; H, 6.84; N, 18.70; Calcd for $C_{23}H_{30}O_3N_6 \cdot 0.1CH_2Cl_2$: C, 62.07; H, 6.81; N, 18.80.

Example 125

5-(5-Acetyl-2-propoxy-3-pyridinyl)-3-ethyl-2-(1-methyl-4-piperidinyl)-2,6-dihydro-7H-pyrazolo[4,3-d]pyrimidin-7-one The title compound was prepared by the method of example 51 using the title compound of example 118.

m.p. 219.0–220.0° C.; 1H NMR (400 MHz, CDCl$_3$): δ=1.05 (t, 3H), 1.38 (t, 3H), 2.85–2.95 (m, 4H), 2.05–2.15 (m, 2H), 2.30 (s, 3H), 2.50 (q, 2H), 2.62 (s, 3H), 3.00–3.05 (m, 4H), 4.15–4.25 (m, 1H), 4.59 (t, 2H), 8.80 (s, 1H), 9.20 (s, 1H), 10.55 (s, 1H); LRMS (TSP-positive ion) 439 (MH$^+$); Anal. Found C, 61.68; H, 6.72; N, 18.61; Calcd for $C_{23}H_{30}O_3N_6 \cdot 0.2H_2O \cdot 0.1DCM$, C, 61.57; H, 6.84; N, 18.65.

Example 126

5-(5-Acetyl-2-propoxy-3-pyridinyl)-3-ethyl-2-(1-ethyl-4-piperidinyl)-2,6-dihydro-7H-pyrazolo[4,3-d]pyrimidin-7-one The title compound was prepared by the method of example 51 using the title compound of example 118 and acetaldehyde.

1H NMR (400 MHz, CDCl$_3$): δ=1.05–1.15 (m, 6H), 1.39 (t, 3H), 1.90–2.00 (m, 5H), 2.07–2.22 (m, 1H), 2.42–2.58 (m, 4H), 2.62 (s, 3H), 3.00–3.10 (m, 3H), 3.10–3.20 (m, 1H), 4.20–4.32 (m, 1H), 4.60–4.65 (m, 2H), 8.84 (s, 1H), 9.22 (s, 1H), 10.58 (s, 1H); LRMS (TSP-positive ion) 453 (MH$^+$); Anal. Found C, 62.13; H, 7.05; N, 17.65; Calcd for $C_{24}H_{32}O_3N_6 \cdot 0.2H_2O \cdot 0.1CH_2Cl_2 \cdot 0.1CH_3OH$, C, 62.13; H, 7.11; N, 17.96.

Example 127

2-[5-(5-Acetyl-2-butoxy-3-pyridinyl)-2-(cyclopropylmethyl)-3-ethyl-2,6-dihydro-7H-pyrazolo[4,3-d]pyrimidin-7-one The title compound from preparation 56 (240 mg, 0.60 mmol) and cesium carbonate (587 mg, 1.80 mmol) were dissolved in n-butanol (12 ml), and the mixture was refluxed for 5 h under nitrogen. The n-butanol was removed in vacuo, and the residue partitioned between dichloromethane (30 ml) and water (30 ml). The organic layer was separated, and the aqueous extracted with dichloromethane (2×30 ml). The combined organics were dried (MgSO$_4$) and concentrated in vacuo. The crude product was purified by flash column chromatography (99:1 methylene chloride:methanol as eluent), and then recrystallised from dichloromethane/diisopropylether to yield the title compound as a cream solid (48 mg, 0.12 mmol).

m.p. 184–185° C.; 1H NMR (400 MHz, CDCl$_3$): δ=0.45 (d, 2H), 0.60 (d, 2H), 0.98 (t, 3H), 1.38 (m, 1H), 1.40 (t, 3H), 1.52 (m, 2H), 1.90 (m, 2H), 2.62 (s, 3H), 3.03 (q, 2H), 4.18 (d, 2H), 4.64 (t, 2H), 8.81 (s, 1H), 9.11 (s, 1H), 10.58 (br s, 1H). LRMS (TSP-positive) 410 (MH$^+$); Anal. Found C, 64.28; H, 6.66; N, 17.03. Calcd for $C_{22}H_{27}O_3N_5$: C, 64.53; H, 6.65; N, 17.10.

Example 128

2-[5-(5-Acetyl-2-ethoxy-3-pyridinyl)-2-((cyclopropyl)methyl)-3-ethyl-2,6-dihydro-7H-pyrazolo[4,3-d]pyrimidin-7-one The title compound from preparation 56 (250 mg, 0.63 mmol) and cesium carbonate (612 mg, 1.88 mmol) were dissolved in ethanol (15 ml) in the presence of powdered molecular sieves, and the mixture was refluxed for 16 h under nitrogen. Further cesium carbonate (103 mg, 0.32 mmol) and powdered molecular sieves were then added, and the mixture transferred into a bomb and heated for 6 h at 100° C. The mixture was then diluted with ethyl acetate (50 ml), filtered to remove the molecular sieves and concentrated in vacuo. The residues was partitioned between dichloromethane (50 ml) and water (50 ml), the organic layer separated, and the aqueous layer extracted further with dichloromethane (2×30 ml). The combined organic layers were dried (MgSO$_4$), and concentrated in vacuo. The crude product was purified by flash column chromatography (99:1 methylene chloride:methanol; then 1:1 ethyl acetate:pentane as eluents), to yield the title compound as a cream solid (45 mg, 0.12 mmol).

m.p. 200–201° C.; 1H NMR (400 MHz, CDCl$_3$): δ=0.45 (d, 2H), 0.60 (m, 2H), 1.39 (m, 1H), 1.42 (t, 3H), 1.52 (t, 3H), 2.61 (s, 3H), 3.03 (q, 2H), 4.18 (d, 2H), 4.71 (q, 2H), 8.81 (s, 1H), 9.22 (s, 1H), 10.59 (br s, 1H). LRMS (ES-positive) 382 (MH$^+$); Anal. Found C, 59.89; H, 5.80; N, 17.01. Calcd for $C_{20}H_{23}O_3N_5 \cdot 0.3CH_2Cl_2$: C, 59.92; H, 5.85; N, 17.21.

Example 129 tert-Butyl 4-[5-(5-Acetyl-2-butoxy-3-pyridinyl)-3-ethyl-7-oxo-6,7-dihydro-2H-pyrazolo[4,3-d]pyrimidin-2-yl]-1-piperidinecarboxylate The title compound from preparation 62 (3.70 g, 7.00 mmol) and cesium carbonate (6.84 g, 21.0 mmol) were dissolved in n-butanol (60 ml) in the presence of powdered molecular sieves and refluxed under nitrogen for 2 h. After removal of the solvent in vacuo, the mixture was partitioned between ethyl acetate (100 ml) and water (50 ml). The organic layer was separated, and the aqueous layer was extracted with ethyl acetate (2×50 ml). Combined organic layers were dried (MgSO$_4$), concentrated in vacuo, and the crude product purified by flash column chromatography (99:1 methylene chloride:methanol as eluant). Addition of diethyl ether gave the title compound as a white powder (1.55 g, 2.88 mmol).

m.p. 194–195° C.; 1H NMR (400 MHz, CDCl$_3$): δ=1.00 (t, 3H), 1.42 (t, 3H), 1.49 (s, 9H), 1.52 (m, 2H), 1.92 (m,

4H), 2.40 (m, 2H), 2.63 (s, 3H), 2.90 (m, 2H), 3.07 (q, 2H), 4.38 (m, 2H), 4.40 (m, 1H), 4.66 (t, 2H), 8.84 (s, 1H), 9.22 (s, 1H), 10.60 (br s, 1H); LRMS (TSP-positive) 539 (MH$^+$), 439 (MH$^+$-BOC); Anal. Found C, 62.15; H, 7.17; N, 15.53. Calcd for $C_{28}H_{38}O_5N_6$: C, 62.44; H, 7.11; N, 15.60.

Example 130

5-(5-Acetyl-2-butoxy-3-pyridinyl)-3-ethyl-2-(4-piperidinyl)-2,6-dihydro-7H-pyrazolo[4,3-d]pyrimidin-7-one Trifluoroacetic acid (7 ml, 40%vol) was added to a solution of the title compound of example 129 in dry Methylene chloride (10 ml), and the mixture was stirred at room temperature under nitrogen for 45 mins. The mixture was concentrated in vacuo and the residue partitioned between NaHCO$_3$ (sat. aq., 50 ml) and Methylene chloride (100 ml). The organic layer was separated (emulsion) and washed with water (50 ml). Organic layer was removed, and the aqueous extracted with Methylene chloride (2×50 ml). The combined organics were dried (MgSO$_4$), and concentrated in vacuo. The crude product was purified by column chromatography (95:5:0.5 methylene chloride:methanol:0.88 NH$_3$ as eluent) to yield the title compound (containing trace impurity; carried through crude to next step).

1H NMR (400 MHz, CDCl$_3$): δ=0.98 (t, 3H), 1.39 (t, 3H), 1.50 (m, 2H), 1.90 (m, 2H), 1.92 (m, 2H), 2.15 (m, 2H), 2.61 (s, 3H), 2.81 (m, 2H), 3.03 (q, 2H), 3.32 (m, 2H), 4.39 (m, 1H), 4.62 (t, 2H), 8.80 (s, 1H), 9.19 (s, 1H); LRMS (TSP-positive) 439 (MH$^+$).

Example 131

5-(5-Acetyl-2-butoxy-3-pyridinyl)-2-(1-acetyl-4-piperidinyl)-3-ethyl-2,6-dihydro-7H-pyrazolo[4,3-d]pyrimidin-7-one The title compound was prepared following the method of example 121 from the title compound of example 130.

m.p. 156–157° C.; 1H NMR (400 MHz, CDCl$_3$): δ=0.98 (t, 3H), 1.40 (t, 3H), 1.50 (m, 2H), 1.89 (m, 2H), 1.98 (t, 2H), 2.11 (s, 3H), 2.29 (m, 1H), 2.52 (m, 1H), 2.61 (s, 3H), 2.73 (t, 1H), 3.06 (q, 2H), 3.23 (m, 1H), 4.02 (m, 1H), 4.46 (m, 1H), 4.62 (t, 2H), 4.79 (m, 1H), 8.80 (s, 1H), 9.20 (s, 1H), 10.57 (br s, 1H). LRMS (TSP-positive) 481 (MH$^+$); Anal. Found C, 60.21; H, 6.58; N, 16.68. Calcd for $C_{25}H_{32}O_4N_6.0.3H_2O.0.2CH_2Cl_2$: C, 60.18; H, 6.61; N, 16.71.

Example 132

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one The title compound from example 119 (120 mg, 0.28 mmol) and cesium carbonate (274 mg, 0.84 mmol) were dissolved in n-butanol (4 ml), and heated at 90° C. under nitrogen with molecular sieves for 96 h. The mixture was then partitioned between water (10 ml) and dichloromethane (10 ml). The organic layer was separated, and the aqueous layer extracted further with dichloromethane (3×15 ml). The combined organic layers were dried (MgSO$_4$), and concentrated in vacuo. The crude product was purified by flash column chromatography (95:5:0.5–90:10:1 ethyl acetate:methanol:0.88 NH$_3$ as eluents), to yield the title compound as a colourless glass (77 mg, 0.18 mmol).

m.p. 91.6–93.7° C.; 1H NMR (400 MHz, CDCl$_3$): δ=1.00–1.05 (m, 6H), 1.38 (t, 3H), 1.50–1.62 (m, 2H), 1.90–2.00 (m, 2H), 2.63 (s, 3H), 2.63–2.70 (m, 2H), 3.02 (q, 2H), 3.75 (t, 2H), 3.90 (t, 2H), 4.68 (t, 2H), 5.10–5.20 (m, 1H), 8.84 (s, 1H), 9.23 (s, 1H), 10.63 (br s, 1H). LRMS (TSP-positive ion) 439 (MH$^+$); Anal. Found C, 60.73; H, 7.06; N, 18.03; Calcd for $C_{23}H_{30}O_3N_6.0.2MeOH.0.1$ DIPE: C, 60.88; H, 7.26; N, 17.90.

Example 133

5-(5-Acetyl-2-butoxy-3-pyridinyl)-3-ethyl-2-(2-pyridinylmethyl)-2,6-dihydro-7H-pyrazolo[4,3-d]pyrimidin-7-one The title compound was prepared from the product of example 116 by the method of example 132.

1H NMR (400 MHz, CDCl$_3$): δ=1.00 (t, 3H), 1.35 (t, 3H), 1.50–1.60 (m, 2H), 1.90–2.00 (m, 2H), 2.60 (s, 3H), 3.05 (q, 2H), 4.60 (t, 2H), 5.65 (s, 2H), 7.10 (d, 1H), 7.20 (m, 1H), 7.60 (dd, 1H), 8.60 (d, 1H), 8.85 (s, 1H), 9.25 (s, 1H), 11.65 (s, 1H); LRMS (TSP-positive ion) 447 (MH$^+$); Anal. Found C, 63.73; H, 5.91; N, 18.02. Calcd for $C_{24}H_{26}O_3N_6.0.25H_2O.0.1EtOAc$: C, 63.74; H, 5.98; N, 18.28.

Example 134

5-(5-Acetyl-2-isobutoxy-3-pyridinyl)-3-ethyl-2-(2-pyridinylmethyl)-2,6-dihydro-7H-pyrazolo[4,3-d]pyrimidin-7-one The title compound was prepared from the product of example 116 by the method of example 132.

1H NMR (400 MHz, CDCl$_3$): δ=1.10 (d, 6H), 1.30 (t, 3H), 2.30 (m, 1H), 2.60 (s, 3H), 3.00 (q, 2H), 4.45 (d, 2H), 5.65 (s, 2H), 7.10 (d, 1H), 7.25 (m, 1H), 7.60 (dd, 1H), 8.60 (d, 1H), 8.80 (s, 1H), 9.20 (s, 1H), 10.70 (s, 1H); LRMS (TSP-positive ion) 447 (MH$^+$); Anal. Found C, 62.47; H, 5.87; N, 16.70. Calcd for $C_{24}H_{26}O_3N_6.0.5H_2O.0.5EtOAc$: C, 62.51; H, 6.25; N, 16.82.

Example 135

5-(5-Acetyl-2-isobutoxy-3-pyridinyl)-3-ethyl-2-(1-methyl-4-piperidinyl)-2,6-dihydro-7H-pyrazolo[4,3-d]pyrimidin-7-one The title compound was prepared from the product of example 125 following the method of example 132.

m.p. 195.0–196.0° C.; 1H NMR (300 MHz, CDCl$_3$): δ=1.08 (d, 6H), 1.38 (t, 3H), 1.88 (d, 2H), 2.10 (t, 2H), 2.20–2.30 (m, 1H), 2.30 (s, 3H), 2.50 (q, 2H), 2.62 (s, 3H), 2.88–3.05 (m, 4H), 4.17–4.23 (m, 1H), 4.41 (d, 2H), 8.80 (s, 1H), 9.19 (s, 1H), 10.52 (s, 1H); LRMS (TSP-positive ion) 453 (MH$^+$); Anal. Found C, 63.15; H, 7.24; N, 17.90; Calcd for $C_{24}H_{32}O_3N_6.0.3H_2O.0.1DIPE$, C, 63.11; H, 7.32; N, 17.95.

Example 136

5-(5-Acetyl-2-isobutoxy-3-pyridinyl)-3-ethyl-2-(1-methyl-3-azetidinyl)-2,6-dihydro-7H-pyrazolo[4,3-d]pyrimidin-7-one The title compound was prepared by the method of example 132 from the title compound of example 120.

1H NMR (400 MHz, CDCl$_3$): δ=1.10 (d, 6H), 1.39 (t, 3H), 2.22–2.37 (m, 1H), 2.50 (s, 3H), 2.62 (s, 3H), 3.05 (q,

2H), 3.89 (t, 2H), 3.95 (t, 2H), 4.45 (d, 2H), 5.14 (m, 1H), 8.83 (s, 1H), 9.22 (s, 1H), 10.62 (br s, 1H); LRMS (TSP-positive ion) 425.5 (MH$^+$).

Example 137

2-(1-Acetyl-4-piperidinyl)-5-[2-butoxy-5-(1-hydroxyethyl)-3-pyridinyl]-3-ethyl-2,6-dihydro-7H-pyrazolo[4,3-d]pyrimidin-7-one Sodium borohydride (6 mg, 0.15 mmol) was added to a suspension of the title compound from example 131 (140 mg, 0.3 mmol) in dry methanol (3 ml) at 0° C. under nitrogen. After 30 min the solvent was removed in vacuo, and the residue partitioned between ethyl acetate (20 ml) and water (20 ml). The organic layer was separated, and the aqueous layer was extracted further with ethyl acetate (2×20 ml). Combined organic layers were washed with brine (20 ml), dried (MgSO$_4$) and concentrated in vacuo. The crude product was purified by flash column chromatography (98:2 to 95:5 methylene chloride:methanol as eluent) to yield the title compound as a white foam (120 mg, 0.25 mmol).

1H NMR (300 MHz, CDCl$_3$): δ=1.00 (t, 3H), 1.40 (t, 3H), 1.54 (m, 2H), 1.60 (d, 3H), 1.91 (m, 2H), 2.01 (t, 2H), 2.13 (m, 1H), 2.17 (s, 3H), 2.32 (m, 1H), 2.59 (m, 1H), 2.78 (t, 1H), 3.08 (q, 2H), 3.28 (t, 1H), 4.08 (m, 1H), 4.50 (m, 1H), 4.58 (t, 2H), 4.83 (m, 1H), 5.03 (m, 1H), 8.27 (s, 1H), 8.86 (s, 1H), 10.84 (br s, 1H). LRMS (TSP-positive) 483.8 (MH$^+$).

Example 138

5-(5-Acetyl-2-ethoxy-3-pyridinyl)-3-ethyl-1-[(1-methyl-1H-imidazol-2-yl)methyl]-1,6-dihydro-7H-pyrazolo[4,3-d]pyrimidin-7-one The title compound was prepared by the method of example 128 from the title compound of preparation 63.

mpt. 217.9–218.7° C. 1H NMR (400 MHz, CDCl$_3$): δ=1.18 (t, 3H), 1.58 (t, 3H), 2.61 (s, 3H), 2.95 (q, 2H), 3.75 (s, 3H), 4.70 (q, 2H), 5.83 (s, 2H), 6.80 (s, 1H), 6.98 (s, 1H), 8.81 (s, 1H), 9.25 (s, 1H), 10.88 (br s, 1H); LRMS (TSP-positive) 422 (MH$^+$); Anal. Found C, 59.50; H, 5.46; N, 23.11. Calcd for C$_{21}$H$_{23}$O$_3$N$_7$: C, 59.85; H, 5.50; N, 23.26.

Example 139

5-(2-Butoxy-5-tetrahydro-2-furanyl-3-pyridinyl)-3-ethyl-2-(2-methoxyethyl)-2,6-dihydro-7H-pyrazolo[4,3-d]pyrimidin-7-one A solution of the title compound from example 12 (50 mg, 0.11 mmol) in ethanol (10 ml) was charged with 10% Pd on carbon (15 mg) and stirred at room temperature for 6 h under 60 psi of hydrogen. After removal of the catalyst by filtration, the reaction mixture was concentrated in vacuo and purified by column chromatography (eluting with methylene chloride to 98:2 methylene chloride:methanol) to afford the title compound as a white solid after precipitation from diethyl ether (15 mg, 0.03 mmol).

1H NMR (300 MHz, CDCl$_3$): δ=1.0 (t, 3H), 1.4 (t, 3H), 1.45–1.6 (m, 2H), 1.8–1.95 (m, 3H), 2.0–2.1 (m, 2H), 2.3–2.4 (m, 1H), 3.15 (q, 2H), 3.25 (s, 3H), 3.9 (t, 2H), 3.9–4.0 (m, 1H), 4.1–4.2 (m, 1H), 4.45 (t, 2H), 4.55 (t, 2H), 4.95 (app t, 1H), 8.25 (d, 1H), 8.65 (d, 1H), 10.8 (br s, 1H). LRMS (TSP) 442 (MH$^+$), 464 (MNa$^+$).

Example 140

5-[5-Acetyl-2-(2-methoxyethoxy)-3-pyridinyl]-3-[6-(dimethylamino)-3-pyridinyl]-2-methyl-2,6-dihydro-7H-pyrazolo[4,3-d]pyrimidin-7-one The title compound was prepared from the product of example 59 via the method of example 132 using 2-methoxyethanol in 28% yield (25 mg).

1H NMR (400 MHz, CDCl$_3$): δ=2.6 (s, 3H), 3.2 (s, 6H), 3.58 (s, 3H), 3.87 (t, 2H), 4.18 (s, 3H), 4.8 (t, 2H), 6.7 (d, 1H), 7.8 (d, 1H), 8.45 (s, 1H), 8.83 (s, 1H), 9.15 (s, 1H), 10.9 (br s, 1H). LRMS (TSP) 464 (MH$^+$).

Example 141

5-(5-Iodo-2-isobutoxy-3-pyridinyl)-2-methyl-3-propyl-2,6-dihydro-7H-pyrazolo[4,3-d]pyrimidin-7-one The title compound was prepared from the product of preparation 64 using the method of example 1 and isobutanol as solvent.

1H NMR (300 MHz, CDCl$_3$): δ=1.0 (3H, t), 1.1 (6H, d), 1.75–1.9 (2H, m), 2.2–2.35 (1H, m), 3.0 (2H, t), 4.1 (3H, s), 4.35 (2H, d), 8.4 (1H, s), 8.95 (1H, s). Analysis: Found C, 46.1; H, 4.70; N, 14.85. Calcd for C$_{18}$H$_{22}$N$_5$O$_2$I: C, 46.26; H, 4.75; N, 14.99%.

Example 142

5-[2-Isobutoxy-5-(methylsulfinyl)-3-pyridinyl]-2-methyl-3-propyl-2,6-7H-pyrazolo[4,3-d]pyrimidin-7-one The title compound of example 141 (500 mg, 1.07 mmol) and thiourea (90 mg, 1.18 mmol) were suspended in N,N-dimethylformamide (3 ml), degassed at 70° C., and treated with bis(triethylphosphine)nickel(II) chloride (20 mg, 0.05 mmol). Sodium cyanoborohydride (80 μl of 1M solution in THF, 0.08 mmol) was added, and the resultant black reaction mixture heated for ¾ h before further bis(triethylphosphine) nickel(II) chloride (60 mg, 0.16 mmol) and sodium cyanoborohydride (160 μl of 1M solution in THF, 0.16 mmol) were added and the reaction mixture heated for a further 6 h. The green reaction mixture was allowed to cool to room temperature and calcium oxide (90 mg, 1.6 mmol) added. After 1 h, methyl iodide (150 ?l, 2.4 mmol) was added and the mixture stirred for a further 1 h. The reaction mixture was diluted with ethyl acetate (20 ml) and citric acid (10% aq, 20 ml), the organic phase separated and washed with further citric acid (2×20 ml), brine (20 ml) and dried (MgSO$_4$) to afford crude 5-[2-isobutoxy-5-(methylsulfanyl)-3-pyridinyl]-2-methyl-3-propyl-2,6-dihydro-7H-pyrazolo[4,3-d]pyrimidin-7-one.

The crude sulphide (284 mg, assume 0.73 mmol) was dissolved in ice-cold methylene chloride (4 ml) and isopropyl alcohol (1 ml), treated with 3-chloroperbenzoic acid (230 mg of 55% active, 0.73 mmol) and allowed to stir at 0° C. for 1 h after which the solvent was removed in vacuo. The residue taken up in ethyl acetate (20 ml), washed with sodium carbonate (10% aq, 2×5 ml), brine (5 ml) and dried (MgSO$_4$) before condensing to a solid which was purified by column chromatography (ethyl acetate:pentane 1:1 to ethyl acetate, then ethyl acetate:methanol 99:1) to afford an analytical sample of the title compound (50 mg, 0.13 mmol) together with impure sulphoxide (66 mg, 0.16 mmol).

1H NMR (300 MHz, CDCl$_3$): δ=1.0 (3H, t), 1.1 (6H, d), 1.75–1.85 (2H, m), 2.25–2.35 (1H, m), 2.8 (3H, s), 3.0 (2H, t), 4.1 (3H, s), 4.4 (2H, d), 8.5 (1H, s), 9.0 (1H, s), 10.7 (1H, br s). LRMS (TSP) 404 (MH$^+$), 426 (MNa$^+$).

Example 143

5-[2-Isobutoxy-5-(methylsulfonyl)-3-pyridinyl]-2-methyl-3-propyl-2,6-dihydro-7-H-pyrazolo[4,3-d]pyrimidin-7-one The title compound of example 142 (36 mg, 0.09 mmol) in ice-cold methyl chloride (3 ml) was treated with 3-chloroperbenzoic acid (36 mg, 50% pure, 0.09 mmol) and stirred for 2 h with ice-cooling. The reaction mixture was diluted with methylene chloride (20 ml) washed with sodium carbonate (10% aq., 2×20 ml), brine (20 ml), dried (MgSO$_4$) and concentrated to afford the title compound as a white solid (37 mg, 0.09 mmol).

1H NMR (300 MHz, CDCl$_3$): δ=1.0 (3H, t), 1.1 (6H, d), 1.75–1.9 (2H, m), 2.25–2.4 (1H, m), 3.0 (2H, t), 3.2 (3H, s), 4.1 (3H, s), 4.5 (2H, d), 8.8 (1H, d), 9.2 (1H, d), 10.6 (1H, br s). LRMS (TSP) 420 (MH$^+$).

Biological Actvity

Compound of the invention were found to have in vitro activities as inhibitors cGMP PDE5 with IC$_{50}$ values of less than about 100 nM.

The following Table illustrates the in vitro activities for a range of compounds of the invention as inhibitors of cGMP PDE5.

| Example | IC$_{50}$ (nM) |
|---|---|
| 5 | 8.5 |
| 16 | 6.55 |
| 34 | 30.7 |
| 48 | 2.45 |
| 49 | 18 |
| 59 | 1.41 |
| 64 | 7 |
| 65 | 4 |
| 71 | 1 |
| 72 | 0.3 |
| 73 | 5 |
| 75 | 5 |
| 76 | 3 |
| 77 | 0.9 |
| 78 | 0.3 |
| 79 | 1.6 |
| 80 | 0.9 |
| 81 | 2 |
| 82 | 4 |
| 83 | 2 |
| 84 | 7.5 |

What is claimed is:

1. A compound of general formula I:

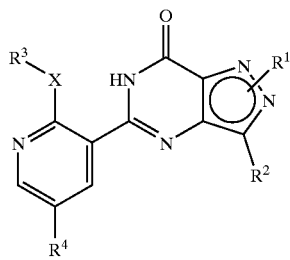

or a pharmaceutically or veterinarily acceptable salt thereof, wherein

X represents O or NR$^5$

R$^1$ represents H, lower alkyl, Het, alkylHet, aryl or alkylaryl (which latter five groups are all optionally substituted with one or more substituents selected from halo, cyano, nitro, lower alkyl, halo(loweralkyl), OR$^6$, OC(O)R$^7$, C(O)R$^8$, C(O)OR$^9$, C(O)NR$^{10}$R$^{11}$, NR$^{12}$R$^{13}$ and SO$_2$NR$^{14}$R$^{15}$)

R$^2$ represents H, halo, cyano, nitro, OR$^6$, OC(O)R$^7$, C(O)R$^8$, C(O)OR$^9$, C(O)NR$^{10}$R$^{11}$, NR$^{12}$R$^{13}$, SO$_2$NR$^{14}$R$^{15}$, lower alkyl, Het, alkylHet, aryl or alkylaryl (which latter five groups are all optionally substituted with one or more substituents selected from halo, cyano, nitro, lower alkyl, halo(loweralkyl), OR$^6$, OC(O)R$^7$, C(O)R$^8$, C(O)OR$^9$, C(O)NR$^{10}$R$^{11}$, NR$^{12}$R$^{13}$ and SO$_2$NR$^{14}$R$^{15}$)

R$^3$ represents H, lower alkyl, alkylHet or alkylaryl (which latter three groups are all optionally substituted with one or more substituents selected from halo, cyano, nitro, lower alkyl, halo(loweralkyl), OR$^6$, OC(O)R$^7$, C(O)R$^8$, C(O)OR$^9$, C(O)NR$^{10}$R$^{11}$, NR$^{12}$R$^{13}$ and SO$_2$NR$^{14}$R$^{15}$)

R$^4$ represents H, halo, cyano, nitro, halo(loweralkyl), OR$^6$, OC(O)R$^7$, C(O)R$^8$, C(O)OR$^9$, C(O)NR$^{10}$R$^{11}$, NR$^{12}$R$^{13}$, NR$^{16}$Y(O)R$^{17}$, N[Y(O)R$^{17}$]$_2$, SOR$^{18}$, SO$_2$R$^{19}$, C(O)AZ, lower alkyl, lower alkenyl, lower alkynyl, Het, alkylHet, aryl, alkylaryl (which latter seven groups are all optionally substituted with one or more substituents selected from halo, cyano, nitro, lower alkyl, halo(loweralkyl), OR$^6$, OC(O)R$^7$, C(O)R$^8$, C(O)OR$^9$, C(O)NR$^{10}$R$^{11}$, NR$^{12}$R$^{13}$ and SO$_2$NR$^{14}$R$^{15}$)

Y represents C or S(O)

A represents lower alkylene

Z represents OR$^6$, halo, Het or aryl (which latter two groups are both optionally substituted with one or more substituents selected from halo, cyano, nitro, lower alkyl, halo(loweralkyl), OR$^6$, OC(O)R$^7$, C(O)R$^8$, C(O)OR$^9$, C(O)NR$^{10}$R$^{11}$, NR$^{12}$R$^{13}$ and SO$_2$NR$^{14}$R$^{15}$)

R$^{10}$ and R$^{11}$ independently represent H or lower alkyl (which latter group is optionally substituted with one or more substituents selected from halo, cyano, nitro, lower alkyl, halo(loweralkyl), OR$^6$, OC(O)R$^7$, C(O)R$^8$, C(O)OR$^9$, C(O)NR$^{10a}$R$^{11a}$, NR$^{12}$R$^{13}$, SO$_2$NR$^{14}$R$^{15}$ and NR$^{20}$S(O)$_2$R$^{21}$ or Het or aryl optionally substituted with one or more of said latter thirteen groups) or one of R$^{10}$ and R$^{11}$ may be lower alkoxy, amino or Het, which latter two groups are both optionally substituted with lower alkyl R$^{10a}$ and R$^{11a}$ independently represent R$^{10}$ and R$^{11}$ as defined above, except that they do not represent groups that include lower alkyl, Het or aryl, when these three groups are substituted (as appropriate) by one or more substituents that include one or more C(O)NR$^{10a}$R$^{11a}$ and/or NR$^{12}$R$^{13}$ groups R$^{12}$ and R$^{13}$ independently represent H or lower alkyl (which latter group is optionally substituted with one or more substituents selected from OR$^6$, C(O)OR$^9$, C(O)NR$^{22}$R$^{23}$ and NR$^{24}$R$^{25}$), one of R$^{12}$ or R$^{13}$ may be C(O)-lower alkyl or C(O)Het (in which Het is optionally substituted with lower alkyl), or R$^{12}$ and R$^{13}$ together represent C$_{3-7}$ alkylene (which alkylene group is optionally unsaturated, optionally substituted by one or more lower alkyl groups and/or optionally interrupted by O or NR$^{26}$)

R$^{14}$ and R$^{15}$ independently represent H or lower alkyl or R$^{14}$ and R$^{15}$, together with the nitrogen atom to which they are bound, form a heterocyclic ring R$^{16}$ and R$^{17}$ independently represent H or lower alkyl (which latter group is optionally substituted with one or more substituents selected from OR$^6$, C(O)OR$^9$, C(O)NR$^{22}$R$^{23}$ and NR$^{24}$R$^{25}$) or one of R$^{16}$ and R$^{17}$ may be Het or aryl, which latter two groups are both optionally substituted with lower alkyl R$^5$, R$^6$, R$^7$, R$^8$, R$^9$, R$^{18}$, R$^{19}$, R$^{20}$, R$^{22}$, R$^{23}$, R$^{24}$ and R$^{25}$ independently represent H or lower alkyl

107

R$^{18}$ and R$^{19}$ independently represent lower alkyl

R$^{21}$ represents lower alkyl or aryl

R$^{26}$ represents H, lower alkyl, aryl, C(O)R$^{27}$ or S(O)$_2$R$^{28}$

R$^{27}$ represents H, lower alkyl or aryl

R$^{28}$ represents lower alkyl or aryl

Het represents an optionally substituted four- to twelve-membered heterocyclic group, which group contains one or more heteroatoms selected from nitrogen, oxygen and/or sulfur with the provisos:
  (i) that R$^4$ is not NH$_2$ when: R$^1$ is C$_{1-3}$ alkyl optionally substituted with phenyl, Het or a N-linked heterocyclic group selected from piperidinyl and morpholinyl; wherein said phenyl group is optionally substituted by one or more substituents selected from C$_{1-4}$ alkoxy; halo; CN; CF$_3$, OCF$_3$ or C$_{1-4}$ alkyl wherein said C$_{1-4}$ alkyl group is optionally substituted by C$_{1-4}$ haloalkyl or C$_{1-4}$ haloalkoxy either of which is substituted by one or more halo atoms; and R$^2$ is C$_{1-6}$ alkyl;
  (ii) that R$^4$ is not NH$_2$ or NO$_2$ when: X is O; and R$^2$ is H, halo, optionally substituted lower alkyl, OR$^6$, C(O)NR$^{10}$R$^{11}$, C(O)OR$^9$, NR$^{12}$R$^{13}$, NHC(O)-lower alkyl, cyano, aryl, alkylaryl, Het or alkylHet (which latter four groups are optionally substituted); and
  (iii) that R$^4$ is not H when: X is O; and R$^2$ is H, optionally substituted lower alkyl, OR$^6$, C(O)NR$^{10}$R$^{11}$, C(O)OR$^9$, NR$^{12}$R$^{13}$, NHC(O)-lower alkyl, cyano, aryl, alkylaryl, Het or alkylHet (which latter four groups are optionally substituted).

2. Compound as claimed in claim 1, wherein R$^1$ represents optionally substituted lower alkyl.

3. Compound as claimed in claim 2, wherein R$^1$ is lower alkyl, lower alkoxy-terminated lower alkyl, NR$^{12}$R$^{13}$-terminated lower alkyl, or N-morpholino-terminated lower alkyl.

4. Compound as claimed in claim 1, wherein R$^1$ represents a 4-piperidinyl group, optionally substituted at the nitrogen atom of the piperidinyl group with lower alkyl or C(O)OR$^9$.

5. Compound as claimed in claim 1, wherein R$^2$ represents C(O)NR$^{10}$R$^{11}$, NR$^{12}$R$^{13}$, lower alkyl optionally interrupted by one or more of O, S or N, optionally substituted at N by lower alkyl or acyl, or optionally substituted aryl or Het.

6. Compound as claimed in claim 5, wherein R$^2$ represents C(O)NR$^{10}$R$^{11}$, NR$^{12}$R$^{13}$, C$_{1-4}$ alkyl optionally interrupted by O or N, optionally substituted at N by lower alkyl, optionally substituted phenyl, or optionally substituted pyridin-2-yl, pyridin-3-yl, pyrimidin-5-yl, pyrazin-2-yl, pyrazol-4-yl, oxadiazol-2-yl, furan-2-yl, furan-3-yl, tetrahydrofuran-2-yl and imidazo[1,2-a]pyridin-6-yl.

7. Compound as claimed in claim 1, wherein R$^3$ represents lower alkyl.

8. Compound as claimed in claim 1, wherein X is O.

9. Compound as claimed in claim 1, wherein R$^4$ represents halo, optionally substituted Het, optionally substituted aryl, C(O)R$^8$, C(O)AZ, C(O)OR$^9$, C(O)NR$^{10}$R$^{11}$, NR$^{12}$R$^{13}$ or NR$^{16}$Y(O)R$^{17}$.

10. Compound as claimed in claim 9, wherein R$^4$ is COCH$_3$ or NHB, wherein B represents H, SO$_2$CH$_3$ or C(O)Het.

11. Compound as claimed in claim 1, wherein R$^4$ represents iodo, lower alkyl, lower alkynyl (which latter two groups are substituted by C(O)OR$^9$ (wherein R$^9$ represents H or C$_{1-6}$ alkyl)), N(H)Y(O)R$^{17}$, N[Y(O)R$^{17}$]$_2$, optionally substituted Het or NR$^{12}$R$^{13}$ (wherein R$^{12}$ and R$^{13}$ together represent C$_{3-5}$ alkylene interrupted by O or N—S(O)$_2$-(aryl)).

108

12. Compound as claimed in claim 11, wherein R$^4$ represents N(H)Y(O)R$^{17}$ (wherein R$^{17}$ represents C$_{1-4}$ alkyl optionally substituted by C(O)OH or C(O)O-lower alkyl) or lower alkynyl terminated by C(O)O—C$_{1-4}$ alkyl.

13. Compound as claimed in claim 1, which is:

5-(2-Butoxy-5-iodo-3-pyridinyl)-3-ethyl-2-(2-methoxyethyl)-2,6-dihydro-7H-pyrazolo[4,3-d]pyrimidin-7-one;

5-(2-Butoxy-5-iodo-3-pyridinyl)-3-ethyl-1-(2-methoxyethyl)-1,6-dihydro-7H-pyrazolo[4,3-d]pyrimidin-7-one;

5-(5-Iodo-2-isobutoxy-3-pyridinyl)-2-methyl-3-propyl-2,6-dihydro-7H-pyrazolo[4,3-d]pyrimidin-7-one;

5-(2-Butoxy-5-iodo-3-pyridinyl)-2-[2-(4-morpholinyl)ethyl]-3-ethyl-2,6-dihydro-7H-pyrazolo[4,3-d]pyrimidin-7-one;

tert-Butyl 4-[5-(2-butoxy-5-iodo-3-pyridinyl)-3-ethyl-7-oxo-6,7-dihydro-2H-pyrazolo[4,3-d]pyrimidin-2-yl]-1-piperidinecarboxylate;

tert-Butyl 3-[5-(2-butoxy-5-iodo-3-pyridinyl)-3-ethyl-7-oxo-6,7-dihydro-2H-pyrazolo[4,3-d]pyrimidin-2-yl]-1-azetidinecarboxylate;

5-(2-Propoxy-5-iodo-3-pyridinyl)-3-ethyl-7-oxo-6,7-dihydro-2H-pyrazolo-[4,3-d]pyrimidin-5-yl] nicotinate;

tert-Butyl [3-ethyl-5-(5-iodo-2-propoxy-3-pyridinyl)-7-oxo-6,7-dihydro-1H-pyrazolo(4,3-d]pyrimidin-1-yl] acetate;

tert-Butyl [3-ethyl-5-(5-iodo-2-propoxy-3-pyridinyl)-7-oxo-6,7-dihydro-2H-pyrazolo[4,3-d]pyrimidin-2-yl] acetate;

[3-Ethyl-5-(5-iodo-2-propoxy-3-pyridinyl)-7-oxo-6,7-dihydro-1H-pyrazolo[4,3-d]pyrimidin-1-yl]acetic acid;

[3-Ethyl-5-(5-iodo-2-propoxy-3-pyridinyl)-7-oxo-6,7-dihydro-2H-pyrazolo[4,3-d]pyrimidin-2-yl]acetic acid;

5-(2-Propoxy-5-iodo-3-pyridinyl)-1-methyl-3-propyl-1,6-dihydro-7H-pyrazolo[4,3-d]pyrimidin-7-one;

2-[2-(Dimethylamino)ethyl]-5-(2-ethoxy-5-iodo-3-pyridinyl)-3-ethyl-2,6-dihydro-7H-pyrazolo[4,3-d]pyrimidin-7-one;

6-Butoxy-5-[3-ethyl-2-(2-methoxyethyl)-7-oxo-6,7-dihydro-2H-pyrazolo[4,3-d]pyrimidin-5-yl]-N-methoxy-N-methylnicotinamide;

5-(5-Acetyl-2-butoxy-3-pyridinyl)-3-ethyl-2-(2-methoxyethyl)-2,6-dihydro-7H-pyrazolo[4,3-d]pyrimidin-7-one;

5-[5-Acetyl-2-(2-methoxy-1-methylethoxy)-3-pyridinyl]-3-ethyl-2-(2-methoxyethyl)-2,6-dihydro-7H-pyrazolo[4,3-d]pyrimidin-7-one;

5-(5-Acetyl-2-butoxy-3-pyridinyl)-3-ethyl-1-(2-methoxyethyl)-1,6-dihydro-7H-pyrazolo[4,3-d]pyrimidin-7-one;

6-Isobutoxy-N,N-dimethyl-5-(2-methyl-7-oxo-3-propyl-6,7-dihydro-2H-pyrazolo[4,3-d]pyrimidin-5-yl)nicotinamide;

5-(5-Glycoloyl-2-isobutoxy-3-pyridinyl)-2-methyl-3-propyl-2,6-dihydro-7H-pyrazolo[4,3-d]pyrimidin-7-one;

5-(5-Acetyl-2-butoxy-3-pyridinyl)-2-[2-(dimethylamino)ethyl]-3-ethyl-2,6-dihydro-7H-pyrazolo[4,3-d]pyrimidin-7-one;

5-(5-Acetyl-2-butoxy-3-pyridinyl)-2-[2-(4-morpholinyl)ethyl]-3-ethyl-2,6-dihydro-7H-pyrazolo[4,3-d]pyrimidin-7-one;

5-(5-Acetyl-2-butoxy-3-pyridinyl)-2-[2-(4-piperidinyl)ethyl]-3-ethyl-2,6-dihydro-7H-pyrazolo[4,3-d]pyrimidin-7-one;

tert-Butyl 4-[2-(5-(5-acetyl-2-butoxy-3-pyridinyl)-3-ethyl-7-oxo-6,7-dihydro-2H-pyrazolo[4,3-d]pyrimidin-2-yl)ethyl]-1-piperidinecarboxylate;

5-(5-Acetyl-2-butoxy-3-pyridinyl)-3-ethyl-2-(1-methyl-4-piperidinyl)-2,6-dihydro-7H-pyrazolo[4,3-d]pyrimidin-7-one;

[5-(5-Acetyl-2-propoxy-3-pyridinyl)-3-ethyl-7-oxo-6,7-dihydro-1H-pyrazolo[4,3-d]pyrimidin-1-yl]acetic acid;

5-(1-Methyl-7-oxo-3-propyl-6,7-dihydro-1H-pyrazolo[4,3-d]pyrimidin-5-yl)-6-propoxynicotinonitrile;

1-Methyl-5-[2-propoxy-5-(1H-tetrazol-5-yl)-3-pyridinyl]-3-propyl-1,6-dihydro-7H-pyrazolo[4,3-d]pyrimidin-7-one;

5-[5-(3-Hydroxy-5-isoxazolyl)-2-propoxy-3-pyridinyl]-1-methyl-3-propyl-1,6-dihydro-7H-pyrazolo[4,3-d]pyrimidin-7-one;

5-(5-Amino-2-propoxy-3-pyridinyl)-1-methyl-3-propyl-1,6-dihydro-7H-pyrazolo[4,3-d]pyrimidin-7-one;

{[5-(1-Methyl-7-oxo-3-propyl-6,7-dihydro-1H-pyrazolo[4,3-d]pyrimidin-5-yl)-6-propoxy-3-pyridinyl]amino}acetic acid;

N-[5-(1-Methyl-7-oxo-3-propyl-6,7-dihydro-1H-pyrazolo[4,3-d]pyrimidin-5-yl)-6-propoxy-3-pyridinyl]methanesulfonamide;

N-[5-(1-Methyl-7-oxo-3-propyl-6,7-dihydro-1H-pyrazolo[4,3-d]pyrimidin-5-yl)-6-propoxy-3-pyridinyl]-3-oxo-β-alanine;

({[5-(1-Methyl-7-oxo-3-propyl-6,7-dihydro-1H-pyrazolo[4,3-d]pyrimidin-5-yl)-6-propoxy-3-pyridinyl]amino}sulfonyl)acetic acid;

N-[5-(1-Methyl-7-oxo-3-propyl-6,7-dihydro-1H-pyrazolo[4,3-d]pyrimidin-5-yl)-6-propoxy-3-pyridinyl]alanine;

5-{2-[2-(Dimethylamino)ethyl]-3-ethyl-7-oxo-6,7-dihydro-2H-pyrazolo-[4,3-d]pyrimidin-5-yl}-6-ethoxynicotinic acid; or 5-{2-[2-(Dimethylamino)ethyl]-3-ethyl-7-oxo-6,7-dihydro-2H-pyrazolo-[4,3-d]pyrimidin-5-yl}-6-ethoxy-N-methoxy-N-methylnicotinamide.

14. A process for the preparation of a compound of formula I, as defined in claim 1, which comprises:

(a) cyclisation of a corresponding compound of formula II:

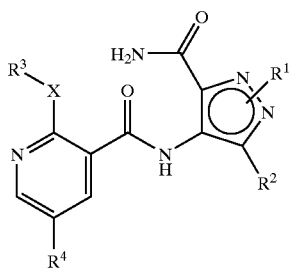

wherein $R^1$, $R^2$, $R^3$, $R^4$ and X are as defined in claim 1;

(b) for compounds of formula I in which $R^1$ represents lower alkyl, Het, aryl, Het, aryl, alkylHet or alkylaryl (which latter five groups are all optionally substituted as defined hereinbefore in respect of $R^1$), alkylation of a corresponding compound of formula I, in which $R^1$ represents H;

(d) conversion of one $R^3$ group to another by alkoxide exchange or amino exchange for alkoxide;

(e) reaction of corresponding compounds of formulae VIII:

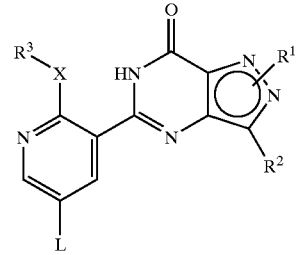

wherein L is a leaving group and $R^1$, $R^2$, $R^3$ and X are as previously defined for compounds of formula I, with a compound containing a group $R^{4a}$ which is capable of exchanging for L;

(f) deprotection of a protected derivative of a compound of formula I;

(g) for compounds of formula I, in which $R^2$ represents $C(O)NR^{10}R^{11}$, and $R^{10}$ and $R^{11}$ are as defined previously for compounds of formula I, reaction of corresponding compounds of formula I, in which $R^2$ represents C(O)OH (or a carboxylic acid derivative thereof) with a compound of formula $HNR^{10}R^{11}$, in which $R^{10}$ and $R^{11}$ are as previously defined for compounds of formula I;

(h) for compounds of formula I, in which $R^2$ represents $C(O)OR^9$, cyclisation of corresponding compounds of formula VI:

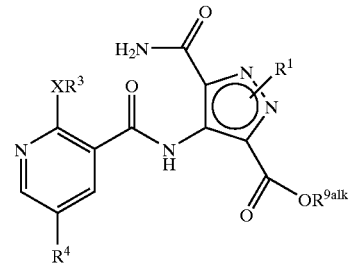

wherein $R^1$, $R^3$, $R^4$ and X are as defined previously for compounds of formula I, and $R^{9alk}$ represents an optionally substituted lower alkyl group, as defined hereinbefore, followed by removal of the alkyl group $R^{9alk}$ (if required) by hydrolysis and/or (if required) exchange with a further optionally substituted alkyl group;

(i) for compounds of formula I, in which $R^2$ represents optionally substituted lower alkyl (which alkyl group is branched and unsaturated at the carbon atom that is attached to the rest of the molecule), $NR^{12}R^{13}$, cyano, aryl or Het (which Het group is either aromatic or unsaturated at the carbon atom that is attached to the rest of the molecule), by cross-coupling of corresponding compounds of formula XXIV:

111

XXIV

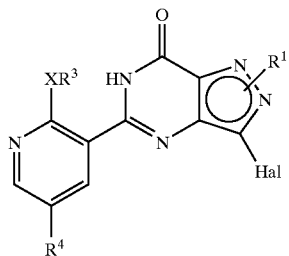

wherein Hal represents Cl, Br or I, and $R^1$, $R^3$, $R^4$ and X are as defined in claim 1, using a compound of formula $$R^{2a}M$$

wherein $R^{2a}$ represents optionally substituted lower alkyl (which alkyl group is branched and unsaturated at the carbon atom that is attached to M), $NR^{12}R^{13}$, cyano, aryl or Het (which Het group is either aromatic or unsaturated at the carbon atom that is attached to M), $R^{12}$ and $R^{13}$ are as defined in claim 1 and M represents a trialkylstannane, dialkylborane, dialkoxyborane, dihydroxyborane, lithium, halomagnesium, halozinc, copper, or halomercury group, which group is suitable for cross-coupling reactions; or (j) for compounds of formulae IA and IB (IA)

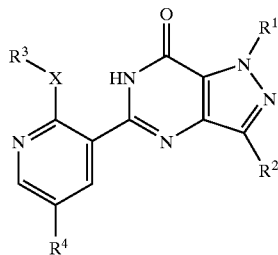

(IB)

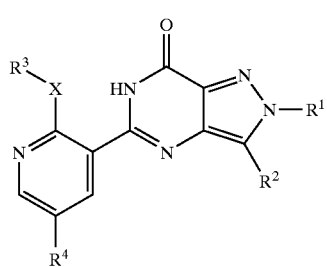

in which $R^2$ represents lower alkoxycarbonyl or lower alkynyl, by a cross-coupling reaction between corresponding compounds of formula XXIV, respectively, as defined above, and a reagent or reagents capable of delivering the lower acyl, lower alkoxycarbonyl or lower alkynyl group.

112

15. A compound of formula IIA, or of formula IIB

IIA

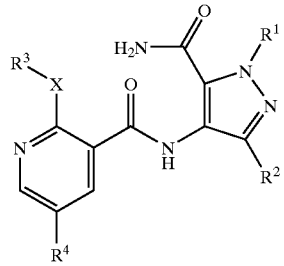

IIB

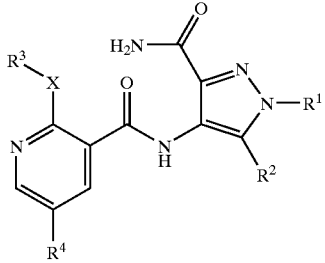

wherein,

X represents O or $NR^5$ $R^1$ represents H, lower alkyl, Het, alkylHet, aryl or alkylaryl (which latter five groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^2$ represents H, halo, cyano, nitro, $OR^6$, $OC(O)R^7$, $C(O)R^8$, $C(O)OR^9$, $C(O)NR^{10}R^{11}$, $NR^{12}R^{13}$, $SO_2NR^{14}R^{15}$, lower alkyl, Het, alkylHet, aryl or alkylaryl (which latter five groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^3$ represents H, lower alkyl, alkylHet or alkylaryl (which latter three groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^4$ represents H, halo, cyano, nitro, halo(loweralkyl), $OR^6$, $OC(O)R^7$, $C(O)R^8$, $C(O)OR^9$, $C(O)NR^{10}R^{11}$, $NR^{12}R^{13}$, $NR^{16}Y(O)R^{17}$, $N[Y(O)R^{17}]_2$, $SOR^{18}$, $SO_2R^{19}$, $C(O)AZ$, lower alkyl, lower alkenyl, lower alkynyl, Het, alkylHet, aryl, alkylaryl (which latter seven groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

Y represents C or S(O)

A represents lower alkylene

Z represents $OR^6$, halo, Het or aryl (which latter two groups are both optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^{10}$ and $R^{11}$ independently represent H or lower alkyl (which latter group is optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10a}R^{11a}$, $NR^{12}R^{13}$, $SO_2NR^{14}R^{15}$ and $NR^{20}S(O)_2R^{21}$ or Het or aryl optionally substituted with one or more of said latter thirteen groups) or one of $R^{10}$ and $R^{11}$ may be lower alkoxy, amino or Het, which latter two groups are both optionally substituted with lower alkyl $R^{10a}$ and $R^{11a}$ independently represent $R^{10}$ and $R^{11}$ as defined above, except that they do not represent groups that include lower alkyl, Het or aryl, when these three groups are substituted (as appropriate) by one or more substituents that include one or more $C(O)NR^{10a}R^{11a}$ and/or $NR^{12}R^{13}$ groups $R^{12}$ and $R^{13}$ independently represent H or lower alkyl (which latter group is optionally substituted with one or more substituents selected from $OR^6$, $C(O)OR^9$, $C(O)NR^{22}R^{23}$ and $NR^{24}R^{25}$), one of $R^{12}$ or $R^{13}$ may be $C(O)$-lower alkyl or $C(O)$Het (in which Het is optionally substituted with lower alkyl), or $R^{12}$ and $R^{13}$ together represent $C_{3-7}$ alkylene (which alkylene group is optionally unsaturated, optionally substituted by one or more lower alkyl groups and/or optionally interrupted by O or $NR^{26}$)

$R^{14}$ and $R^{15}$ independently represent H or lower alkyl or $R^{14}$ and $R^{15}$, together with the nitrogen atom to which they are bound, form a heterocyclic ring $R^{16}$ and $R^{17}$ independently represent H or lower alkyl (which latter group is optionally substituted with one or more substituents selected from $OR^6$, $C(O)OR^9$, $C(O)NR^{22}R^{23}$ and $NR^{24}R^{25}$) or one of $R^{16}$ and $R^{17}$ may be Het or aryl, which latter two groups are both optionally substituted with lower alkyl $R^5$, $R^6$, $R^7$, $R^8$, $R^9$, $R^{18}$, $R^{19}$, $R^{20}$, $R^{22}$, $R^{23}$, $R^{24}$ and $R^{25}$ independently represent H or lower alkyl $R^{18}$ and $R^{19}$ independently represent lower alkyl $R^{21}$ represents lower alkyl or aryl $R^{26}$ represents H, lower alkyl, aryl, $C(O)R^{27}$ or $S(O)_2R^{28}$ $R^{27}$ represents H, lower alkyl or aryl $R^{28}$ represents lower alkyl or aryl Het represents an optionally substituted four- to twelve-membered heterocyclic group, which group contains one or more heteroatoms selected from nitrogen, oxygen and/or sulfur with the provisos:

(i) that $R^4$ is not $NH_2$ when: $R^1$ is $C_{1-3}$ alkyl optionally substituted with phenyl, Het or a N-linked heterocyclic group selected from piperidinyl and morpholinyl; wherein said phenyl group is optionally substituted by one or more substituents selected from $C_{1-4}$ alkoxy; halo; CN; $CF_3$, $OCF_3$ or $C_{1-4}$ alkyl wherein said $C_{1-4}$ alkyl group is optionally substituted by $C_{1-4}$ haloalkyl or $C_{1-4}$ haloalkoxy either of which is substituted by one or more halo atoms; and $R^2$ is $C_{1-6}$ alkyl;

(ii) that $R^4$ is not $NH_2$ or $NO_2$ when: X is O; and $R^2$ is H, halo, optionally substituted lower alkyl, $OR^6$, $C(O)NR^{10}R^{11}$, $C(O)OR^9$, $NR^{12}R^{13}$, $NHC(O)$-lower alkyl, cyano, aryl, alkylaryl, Het or alkylHet (which latter four groups are optionally substituted); and (iii) that $R^4$ is not H when: X is O; and $R^2$ is H, optionally substituted lower alkyl, $OR^6$, $C(O)NR^{10}R^{11}$, $C(O)OR^9$, $NR^{12}R^{13}$, $NHC(O)$-lower alkyl, cyano, aryl, alkylaryl, Het or alkylHet (which latter four groups are optionally substituted).

16. A compound of general formula I:

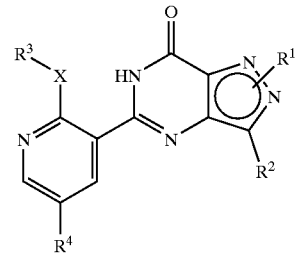

or a pharmaceutically or veterinarily acceptable salt thereof, wherein

X represents O or $NR^5$ $R^1$ represents H, lower alkyl, Het, alkylHet, aryl or alkylaryl (which latter five groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^2$ represents H, halo, cyano, nitro, $OR^6$, $OC(O)R^7$, $C(O)R^8$, $C(O)OR^9$, $C(O)NR^{10}R^{11}$, $NR^{12}R^{13}$, $SO_2NR^{14}R^{15}$, lower alkyl, Het, alkylHet, aryl or alkylaryl (which latter five groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^3$ represents H, lower alkyl, alkylHet or alkylaryl (which latter three groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^4$ represents H, halo, cyano, nitro, halo(loweralkyl), $OR^6$, $OC(O)R^7$, $C(O)R^8$, $C(O)OR^9$, $C(O)NR^{10}R^{11}$, $NR^{12}R^{13}$, $NR^{16}Y(O)R^{17}$, $N[Y(O)R^{17}]_2$, $SOR^{18}$, $SO_2R^{19}$, $C(O)AZ$, lower alkyl, lower alkenyl, lower alkynyl, Het, alkylHet, aryl, alkylaryl (which latter seven groups are all optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

Y represents C or S(O)

A represents lower alkylene

Z represents $OR^6$, halo, Het or aryl (which latter two groups are both optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^{10}$ and $R^{11}$ independently represent H or lower alkyl (which latter group is optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10a}R^{11a}$, $NR^{12}R^{13}$, $SO_2NR^{14}R^{15}$ and $NR^{20}S(O)_2R^{21}$ or Het or aryl optionally substituted with one or more of said latter thirteen groups) or one of $R^{10}$ and $R^{11}$ may be lower alkoxy, amino or Het, which latter two groups are both optionally substituted with lower alkyl $R^{10a}$ and $R^{11a}$ independently represent $R^{10}$ and $R^{11}$ as defined above, except that they do not represent groups that include lower alkyl, Het or aryl, when these three groups are substituted (as appropriate) by one or more substituents that include one or more $C(O)NR^{10a}R^{11a}$ and/or $NR^{12}R^{13}$ groups $R^{12}$ and $R^{13}$ independently represent H or lower alkyl (which latter group is optionally substituted with one or more substituents selected from $OR^6$, $C(O)OR^9$, $C(O)NR^{22}R^{23}$ and $NR^{24}R^{25}$), one of $R^{12}$ or $R^{13}$ may be $C(O)$-lower alkyl or $C(O)$Het (in which Het is optionally substituted with lower alkyl), or $R^{12}$ and $R^{13}$ together represent $C_{3-7}$ alkylene (which alkylene group is optionally unsaturated, optionally substituted by one or more lower alkyl groups and/or optionally interrupted by O or $NR^{26}$)

$R^{14}$ and $R^{15}$ independently represent H or lower alkyl or $R^{14}$ and $R^{15}$, together with the nitrogen atom to which they are bound, form a heterocyclic ring $R^{16}$ and $R^{17}$ independently represent H or lower alkyl (which latter group is optionally substituted with one or more substituents selected from $OR^6$, $C(O)OR^9$, $C(O)NR^{22}R^{23}$ and $NR^{24}R^{25}$) or one of $R^{16}$ and $R^{17}$ may be Het or aryl, which latter two groups are both optionally substituted with lower alkyl $R^5$, $R^6$, $R^7$, $R^8$, $R^9$, $R^{18}$, $R^{19}$, $R^{20}$, $R^{22}$, $R^{23}$, $R^{24}$ and $R^{25}$ independently represent H or lower alkyl $R^{18}$ and $R^{19}$ independently represent lower alkyl $R^{21}$ represents lower alkyl or aryl $R^{26}$ represents H, lower alkyl, aryl, $C(O)R^{27}$ or $S(O)_2R^{28}$ $R^{27}$ represents H, lower alkyl or aryl $R^{28}$ represents lower alkyl or aryl Het represents an optionally substituted four- to twelve-membered heterocyclic group, which group contains one or more heteroatoms selected from nitrogen, oxygen and/or sulfur in admixture with a pharmaceutically or veterinarily acceptable adjuvant, diluent or carrier.

17. A formulation as claimed in claim 16, which is a pharmaceutical formulation.

18. A formulation as claimed in claim 16, which is a veterinary formulation.

* * * * *